(12) United States Patent
Amsallem et al.

(10) Patent No.: US 12,390,171 B1
(45) Date of Patent: Aug. 19, 2025

(54) WEARABLE DEVICES FOR PROVIDING A QUALITATIVE AND ACTIONABLE DESCRIPTOR OF A USER'S PHYSIOLOGICAL STATE, AND METHODS OF USE THEREOF

(71) Applicant: Meta Platforms Technologies, LLC, Menlo Park, CA (US)

(72) Inventors: Myriam Amsallem, San Francisco, CA (US); Brian Keith Cabral, San Jose, CA (US); Isaac Robert Galatzer-Levy, New York, NY (US); Aleksandra Pang, Orinda, CA (US); Michael John Toksvig, Palo Alto, CA (US); Freddy Abnousi, Menlo Park, CA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 335 days.

(21) Appl. No.: 17/866,445

(22) Filed: Jul. 15, 2022

Related U.S. Application Data

(60) Provisional application No. 63/222,817, filed on Jul. 16, 2021.

(51) Int. Cl.
| | | |
|---|---|---|
| A61B 5/00 | (2006.01) | |
| A61B 5/0205 | (2006.01) | |
| A61B 5/11 | (2006.01) | |
| A61B 5/16 | (2006.01) | |

(52) U.S. Cl.
CPC ............ *A61B 5/743* (2013.01); *A61B 5/0205* (2013.01); *A61B 5/1118* (2013.01); *A61B 5/165* (2013.01); *A61B 5/4806* (2013.01); *A61B 5/681* (2013.01); *A61B 5/7246* (2013.01); *A61B 5/7475* (2013.01)

(58) Field of Classification Search
CPC ................................ A61B 5/743; A61B 5/681
See application file for complete search history.

(56) References Cited

U.S. PATENT DOCUMENTS

| | | | |
|---|---|---|---|
| 10,638,965 B2 | 5/2020 | Flax et al. | |
| 11,205,518 B1 * | 12/2021 | Hitt | ...................... A61B 5/1034 |
| 2013/0053656 A1 | 2/2013 | Mollicone et al. | |

(Continued)

*Primary Examiner* — Tammie K Marlen
(74) *Attorney, Agent, or Firm* — Morgan, Lewis & Bockius LLP

(57) ABSTRACT

Systems and methods are provided for presenting a qualitative descriptor of a user's physiological state at a wrist-wearable device. The method includes monitoring, via one or more sensors, values for a plurality of physiological parameters for a user wearing the wrist-wearable device. The method includes comparing the values for the plurality of physiological parameters to baseline values for the physiological parameters. The baseline values are determined based on values for the plurality of physiological parameters that were measured over a predetermined period of time. The method includes, based on the comparison, determining a qualitative descriptor of the user's physiological state from among a set of three or more predefined qualitative descriptors. The method includes presenting, on a display that is in communication with the wrist-wearable device, the qualitative descriptor of the user's physiological state without displaying a numeric score representing the user's physiological state.

20 Claims, 29 Drawing Sheets

(56) References Cited

U.S. PATENT DOCUMENTS

| | | | |
|---|---|---|---|
| 2013/0106684 A1* | 5/2013 | Weast | G04G 17/06 |
| | | | 345/156 |
| 2019/0110755 A1 | 4/2019 | Capodilupo et al. | |
| 2019/0206424 A1 | 7/2019 | Feast et al. | |
| 2019/0216392 A1 | 7/2019 | Bower et al. | |
| 2022/0110547 A1* | 4/2022 | Kinnunen | A61B 5/02416 |

* cited by examiner

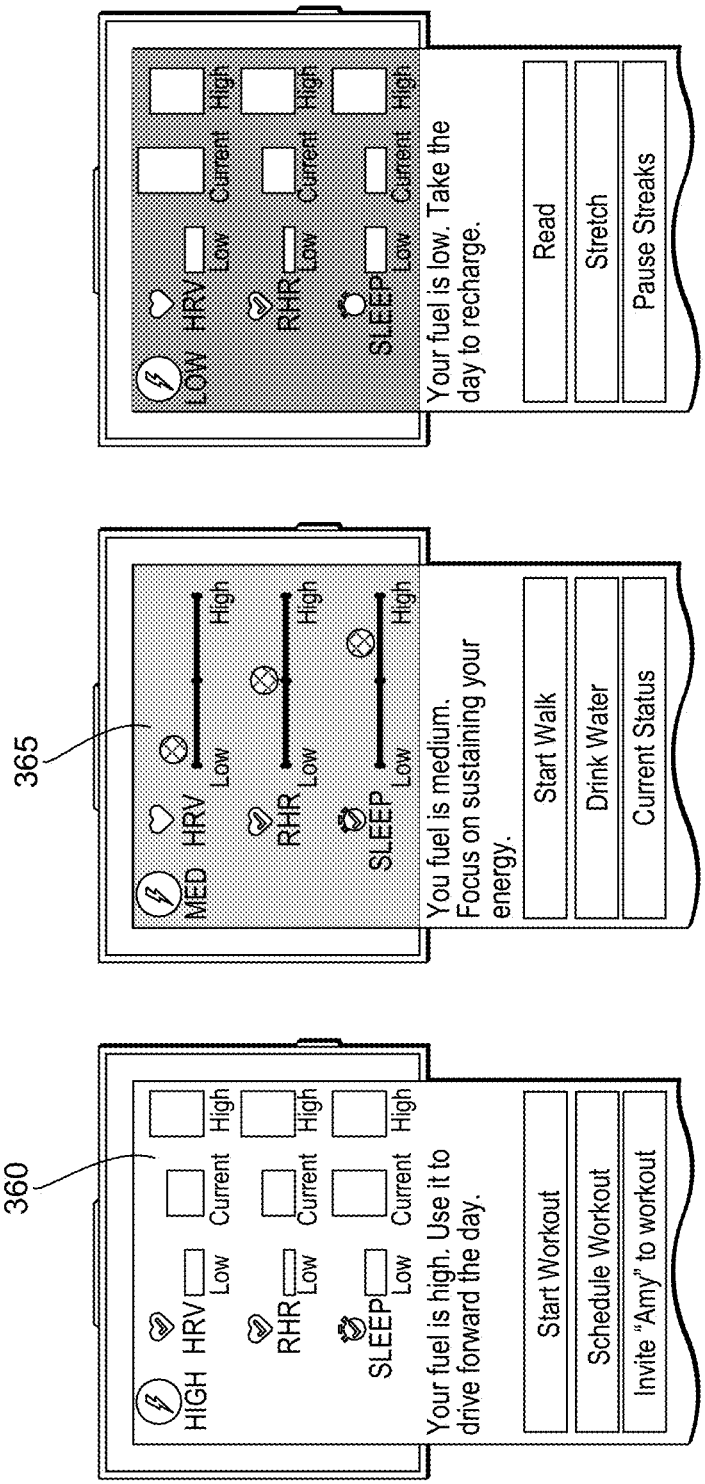

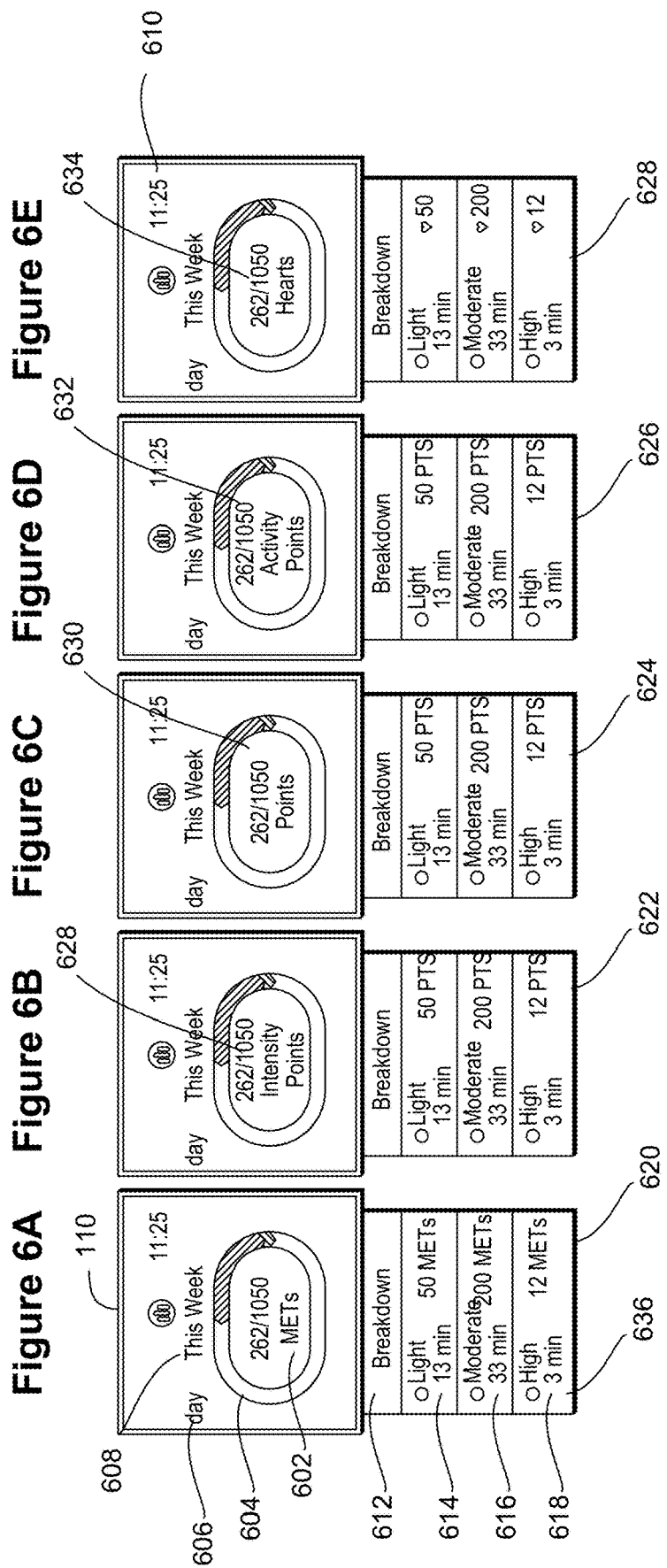

800

810
Monitor via one or more sensors that are in communication with the wrist-wearable device, values for a plurality of physiological parameters for a user wearing the wrist-wearable device.

812
Each sensor of the one or more sensors is physically coupled with the wrist-wearable device.

814
The display is in communication with the wrist-wearable device.

816
The plurality of physiological parameters includes three or more of heart rate, heart rate variability, duration of deep sleep, blood oxygen levels, blood pressure, stress level, energy level, and activity level.

818
Compare the values for the plurality of physiological parameters to baseline values for the physiological parameters, the baseline values being determined based on values for the plurality of physiological parameters that were measured over a predetermined period of time.

819
The baseline values are determined based on values for the plurality of physiological parameters that were measured over a predetermined period of time while the user was in a state of deep sleep.

820
The comparing is conducted using a machine-learning model that was trained using the baseline values for the physiological parameters.

822
The machine-learning model was also trained using (i) subjective indications of the user's physiological state, and (ii) objective indications of a cognitive or motor function of the user, the cognitive or motor function of the user having a first known variance with respect to one or more physiological parameters of the plurality of physiological parameters and the subjective indications having a second known variance with respect to one or more physiological parameters of the plurality of physiological parameters.

824
Based on the comparing, determine a qualitative descriptor of the user's physiological state from among a set of three or more predefined qualitative descriptors.

↓

826
Present on a display that is in communication with the wrist-wearable device, the qualitative descriptor of the user's physiological state without displaying a numeric score representing the user's physiological state.

828
In accordance with a determination that the qualitative descriptor for the user's physiological state corresponds to a low energy state, display on the display a user interface object that allows the user to adjust a physical activity goal by a certain amount.

830
The certain amount is provided by the user or is automatically, without human intervention, determined by the wrist-wearable device.

832
Determine an activity for the user to perform in the physical world that is predicted to be suitable for the user based on the qualitative descriptor of the user's physiological state.

834-a
The qualitative descriptor of the user's physiological state is displayed in a first portion of a user interface on the display, and the method further includes detecting a user input within the first portion of the user interface, and

834-b
In response to detecting the user input within the first portion of the user interface, displaying an additional portion of the user interface that includes a user interface object that, when selected, causes the wrist-wearable device to begin monitoring the user's performance of the activity.

836
The user interface object is a first user interface object, and the displaying the user interface object also includes displaying a second user interface object that, when selected, causes the wrist-wearable device to schedule a future performance of the activity.

838
Displaying the additional portion of the user interface also includes presenting on the display an explanation as to why the activity has been selected as appropriate for the user.

840
In accordance with a determination that the qualitative descriptor for the user's physiological state indicates that the user has a low energy level, the determine an activity for the user to perform in the physical world includes determining at least two activities for the user to perform in the physical world, and the additional portion of the user interface includes respective user interface elements associated with each of the at least two activities for the user to perform in the physical world.

842
Displaying the additional portion of the user interface also includes displaying another user interface element that, when selected, pauses streaks representing performance of physical activities by the user.

After monitoring the user's performance of the activity:
844-a
Monitor via the one or more sensors that are in communication with the wrist-wearable device, new values for the plurality of physiological parameters for the user wearing the wrist-wearable device.
844-b
Compare the new values for the plurality of physiological parameters to the baseline values for the physiological parameters.
844-c
Based on the comparing of the new values to the baseline values, determine a new qualitative descriptor of the user's physiological state from among the set of three or more predefined qualitative descriptors.
844-d
Present on the display that is in communication with the wrist-wearable device, the new qualitative descriptor of the user's physiological state without displaying a numeric score representing the user's physiological state.

846
Determine an activity for the user to perform in the physical world that is predicted to be suitable for the user based on the qualitative descriptor of the user's physiological state also includes determining at least one other user with whom the user should perform the physical activity, and providing a recommendation on the display that the user should perform the physical activity with the at least one other user.

848
The qualitative descriptor is presented on the display along with a background color associated with the qualitative descriptor, and each respective predefined qualitative descriptor in the set of three or more predefined qualitative descriptors is associated with a different background color.

850
Presenting the qualitative descriptor on the display also includes presenting information to the user regarding the values for the plurality of physiological parameters to provide the user with information as to how the qualitative descriptor was determined.

852-a
While presenting information to the user regarding the values for the plurality of physiological parameters, detect another user input within a second portion of the user interface.

852-b
In response to detecting the user input within the second portion of the user interface, display a third portion of the user interface that includes displaying ranges of values for at least one physiological parameter of the plurality of physiological parameters within the additional portion of the user interface.

854
Before determining the qualitative descriptor, provide a description of how qualitative descriptors of the user's physiological state will be determined by the wrist-wearable device and an explanation of research behind the use of qualitative descriptors of the user's physiological state.

856
Before determining the qualitative descriptor, provide a description about values for physiological parameters that will be collected in conjunction with determinations of qualitative descriptors of the user's physiological state by the wrist-wearable device.

Figure 8E

WEARABLE DEVICES FOR PROVIDING A QUALITATIVE AND ACTIONABLE DESCRIPTOR OF A USER'S PHYSIOLOGICAL STATE, AND METHODS OF USE THEREOF

CROSS-REFERENCE TO RELATED APPLICATIONS

This application claims priority to U.S. Prov. App. No. 63/222,817, filed on Jul. 16, 2021, titled "Wearable Devices for Providing a Qualitative and Actionable Descriptor of a User's Physiological State, And Methods of Use Thereof," which is incorporated herein by reference.

TECHNICAL FIELD

The present disclosure relates generally to wearable devices and methods for presenting a qualitative descriptor of a user's physiological state and more particularly to wrist-wearable devices configured to monitor values for physiological parameters of a user using sensors of a wrist-wearable device to determine and then provide a qualitative descriptor of the user's physiological state based on a comparison of the values for the physiological parameters with baseline values for each respective physiological parameter.

BACKGROUND

Computing devices such as smart watches, phones, and tablets can be used to monitor and present users with health information (e.g., heart rate, sleeping patterns) in real time. Although these computing devices provide health information to users, that information is often confusing and/or overwhelming, leaving the user with uncertainty as to what actions they need to be taking based on the health information. Therefore, a need exists for providing users with actionable health information that users can easily and quickly understand to inform their day-to-day activity choices and goals.

SUMMARY

The wrist-wearable devices and methods described herein address the above-mentioned drawbacks by presenting a qualitative descriptor (e.g., a non-numeric descriptor of the user's physiological state, such as high/medium/low) of a user's physiological state at a wrist-wearable device. The wrist-wearable devices and methods described herein use one or more sensors to monitor values for each physiological parameter of a plurality of physiological parameters (e.g., heart rate, heart rate variability, duration of deep sleep, blood oxygen levels, blood pressure, stress level, energy level, activity level, or other physiological parameters) for a user wearing the wrist-wearable device to then determine a current physiological state of the user. In particular, the wrist-wearable devices and methods described herein compare measured or sensed values for the physiological parameters to baseline values for the physiological parameters and, based on the comparisons, the devices determine (or select) a qualitative descriptor from a set of three or more predefined qualitative descriptors. The wrist-wearable devices and methods described herein further present, via a display of the wrist-wearable devices, the determined qualitative descriptor to the user. The qualitative descriptor can be presented without displaying a numeric score representing the user's physiological state. The qualitative descriptor can provide users with easy-to-follow and actionable information relating to overall health and can also provide appropriate activity recommendations based on the determined qualitative descriptor.

In some embodiments, the qualitative descriptor is a metric that integrates physiological metrics (based on, for example, heart rate and sleep) to empower users to approach their day with intentionality. The qualitative descriptor can also represent a user's fuel (an analogue for stamina, which is also referred to herein as energy) levels. More specifically, in some embodiments the qualitative descriptors described represent approachable, actionable, and contextualized health information for actionable use with everyday life. Further, the qualitative descriptor can be used to provide users with one or more self-care recommendations as discussed below. In some embodiments, the qualitative descriptor is based on a combination of at least three health biometrics (i.e., resting heart rate, heart rate variability and sleep data) in a plurality of combinations, including (without limitation to) linear combinations, non-linear combinations, and different weights, that can be attributed to each of the health biometric inputs. The health biometric inputs are also referred to as values for physiological parameters in the description that follows below.

Further, the wrist-wearable devices described herein improve users' daily activities and productivity by providing a compact, hands-free computing system including a display that can be worn throughout the day without inconveniencing the users or restricting their movements (and thus making it easier to interact with their physical and artificial environments in tandem (as a complement to everyday life)). For example, the wrist-wearable devices and methods described herein, in one embodiment, provide improved techniques for providing updated qualitative descriptors to the user about physiological changes that the user experiences throughout the day or while performing one or more activities without inconveniencing or hampering daily life (e.g., working out, walking, meditating, sleeping, working). The use of the qualitative descriptors described herein can be updated throughout the day to help guide users to achieve their overall fitness and health goals, including by adjusting activity goals by accounting for changes in a user's physiological state that can occur throughout the day.

(A1) In accordance with some embodiments, a method of presenting a qualitative descriptor of a user's physiological state at a wrist-wearable device is provided. The method includes monitoring, via one or more sensors that are in communication with the wrist-wearable device, values for a plurality of physiological parameters for a user wearing the wrist-wearable device. The method further includes comparing the values for the plurality of physiological parameters to baseline values for the physiological parameters. The baseline values are determined based on values for the plurality of physiological parameters that were measured over a predetermined period of time. Based on the comparison, the method includes determining a qualitative descriptor of the user's physiological state from among a set of three or more predefined qualitative descriptors. The method includes presenting on a display that is in communication with the wrist-wearable device the qualitative descriptor of the user's physiological state without displaying a numeric score representing the user's physiological state.

(A1.5) In some embodiments of (A1), the baseline values are determined based on values for the plurality of physiological parameters that were measured over a predetermined period of time while the user was in a state of deep sleep (e.g., the stage of sleep that a user typically would need to feel refreshed upon waking up, such as rapid eye movement (REM) sleep).

(A2) In some embodiments of any of (A1)-(A1.5), the method further includes determining an activity for the user to perform in the physical world that is predicted to be suitable for the user based on the qualitative descriptor of the user's physiological state.

(A3) In some embodiments of any of (A1)-(A2), the qualitative descriptor of the user's physiological state is displayed in a first portion of a user interface on the display and the method further includes detecting a user input within the first portion of the user interface. The method includes, in response to detecting the user input within the first portion of the user interface, displaying an additional portion of the user interface that includes a user interface object that, when selected, causes the wrist-wearable device to begin monitoring the user's performance of the activity.

(A4) In some embodiments of any of (A1)-(A3), the method further includes, after monitoring the user's performance of the activity, monitoring, via the one or more sensors that are in communication with the wrist-wearable device, new values for the plurality of physiological parameters for the user wearing the wrist-wearable device. The method includes comparing the new values for the plurality of physical parameters to the baseline values for the physiological parameters. The method further includes determining a new qualitative descriptor of the user's physiological state from among the set of three or more predefined qualitative descriptors based on the comparison. The method further includes, presenting on the display that is in communication with the wrist-wearable device, the new qualitative descriptor of the user's physiological state without displaying a numeric score representing the user's physiological state.

(A5) In some embodiments of any of (A3)-(A4), the user interface object is a first user interface object, and the displaying the user interface object also includes displaying a second user interface object that, when selected, causes the wrist-wearable device to schedule a future performance of the activity.

(A6) In some embodiments of any of (A3)-(A5), the displaying the additional portion of the user interface also includes presenting on the display an explanation as to why the activity has been selected as appropriate for the user.

(A7) In some embodiments of any of (A3)-(A6), the method further includes, in accordance with a determination that the qualitative descriptor for the user's physiological state indicates that the user has a low energy level, the determining an activity for the user to perform in the physical world includes determining at least two activities for the user to perform in the physical world, and the additional portion of the user interface includes respective user interface elements associated with each of the at least two activities for the user to perform in the physical world.

(A8) In some embodiments of any of (A3)-(A7), the displaying the additional portion of the user interface also includes displaying another user interface element that, when selected, pauses streaks representing performance of physical activities by the user.

(A9) In some embodiments of any of (A2)-(A8), the determining the activity for the user to perform in the physical world that is predicted to be suitable for the user based on the qualitative descriptor of the user's physiological state also includes determining at least one other user (e.g., a second user associated with a second wrist-wearable device that is configured to determine and present qualitative descriptors of the second user's physiological state) with whom the user should perform the physical activity, and providing a recommendation on the display that the user should perform the physical activity with the at least one other user.

(A10) In some embodiments of any of (A1)-(A9), the qualitative descriptor is presented on the display along with a background color associated with the qualitative descriptor, and each respective predefined qualitative descriptor in the set of three or more predefined qualitative descriptors is associated with a different background color.

(A11) In some embodiments of any of (A1)-(A10), presenting the qualitative descriptor on the display also includes presenting information to the user regarding the values for the plurality of physiological parameters to provide the user with information as to how the qualitative descriptor was determined.

(A12) In some embodiments of any of (A3)-(A11), the qualitative descriptor of the user's physiological state is displayed in a first portion of a user interface on the display, and the method further includes detecting a user input within the first portion of the user interface. The method includes, in response to detecting the user input within the first portion of the user interface, displaying the additional portion of the user interface, including displaying a range of values for at least one physiological parameter of the plurality of physiological parameters within the additional portion of the user interface.

(A13) In some embodiments of any of (A1)-(A12), the comparing the values for the plurality of physiological parameters to the baseline values for the physiological parameters is conducted using a machine-learning model that was trained using the baseline values for the physiological parameters.

(A14) In some embodiments of (A13), the machine-learning model was also trained using (i) subjective indications of the user's physiological state (ways to obtain these subjective indications are described below, including posing questions to the user to assess that user's physiological state at various points in time) and (ii) objective indications of a cognitive or motor function of the user (ways to obtain these objective indications are described below, including having the user complete tests assessing cognitive or motor functions at various points in time). The cognitive or motor function of the user can have a first known variance with respect to one or more physiological parameters of the plurality of physiological parameters and the subjective indications can have a second known variance with respect to one or more physiological parameters of the plurality of physiological parameters. Advance knowledge of these known variances can allow the wrist-wearable devices described herein to make further adjustments to the determined qualitative descriptions.

(A15) In some embodiments of any of (A1)-(A14), the method further includes, in accordance with a determination that the qualitative descriptor for the user's physiological state corresponds to a low energy state, displaying on the display a user interface object that allows the user to adjust a physical activity goal by a certain amount.

(A16) In some embodiments of (A15), the certain amount is provided by the user or is automatically, without human intervention, determined by the wrist-wearable device (e.g., based on a pattern of activities performed by the user when the user is in a low energy state).

(A17) In some embodiments of any of (A1)-(A16), each sensor of the one or more sensors is physically coupled with the wrist-wearable device.

(A18) In some embodiments of any of (A1)-(A17), the display is physically coupled with the wrist-wearable device. In other words, the wrist-wearable devices described herein both (i) make determinations of the qualitative descriptor of the user's physiological state and (ii) present that qualitative descriptor on the wrist-wearable device's own display.

(A19) In some embodiments of any of (A1)-(A18), the method further includes, before determining the qualitative descriptor, providing a description of how qualitative descriptors of the user's physiological state will be determined by the wrist-wearable device and an explanation of the research behind the use of qualitative descriptors of the user's physiological state.

(A20) In some embodiments of any of (A1)-(A19), the method further includes, before determining the qualitative descriptor, providing a description of values for physiological parameters that will be collected in conjunction with determinations of qualitative descriptors of the user's physiological state by the wrist-wearable device (e.g., showing how detected heart rate or sleep patterns compare to expected results).

(A21) In some embodiments of any of (A1)-(A20), the plurality of physiological parameters includes three or more of heart rate, heart rate variability, duration of deep sleep, blood oxygen levels, and blood pressure.

(B1) In accordance with some embodiments, a wrist-wearable device for providing a qualitative descriptor of a user's physiological state is provided. The wrist-wearable device is configured to perform or cause performance of the method of any of (A1)-(A21).

(C1) In accordance with some embodiments, a non-transitory, computer-readable storage medium is provided. The non-transitory, computer-readable storage medium includes instructions that when executed by a wrist-wearable device cause the wrist-wearable device to perform or cause performance of the method of any of (A1)-(A21).

(D1) In accordance with some embodiments, a system for providing a qualitative descriptor of a user's physiological state is provided. The system includes one or more sensors. The one or more sensors are configured to monitor values for a plurality of physiological parameters for a user wearing the one or more sensors. The system includes one or more processors in communication with the one or more sensors. The one or more processors are configured to compare the values for the plurality of physiological parameters to baseline values for the physiological parameters. The baseline values are determined based on values for the plurality of physiological parameters that were measured over a predetermined period of time. The one or more processors are further configured, based on the comparing, to determine a qualitative descriptor of the user's physiological state from among a set of three or more predefined qualitative descriptors. The system includes a display that is in communication with the one or more sensors and the one or more processors. The display is configured to present the qualitative descriptor of the user's physiological state without displaying a numeric score representing the user's physiological state.

(D2) In some embodiments of (D1), the system is configured to operate in accordance with the method of any of (A1)-(A21).

(E1) In accordance with some embodiments, a capsule housing the one or more sensors, one or more processors, and display recited in (D1) is provided. The capsule is configured to couple with a wearable structure (e.g., a band portion and a cradle portion that is detachably coupled with the capsule) to form a wrist-wearable device, and the capsule includes one or more processors configured to perform or cause performance of the method of any of (A1)-(A21).

(F1) In accordance with some embodiments, a method of determining a qualitative descriptor of a user's physiological state at a wrist-wearable device is provided. In some embodiments, an overall physiological state is based on three different data points. In some embodiments, the overall physiological state is adjusted based on known variance data relating the three data points to one another. In some embodiments, a suitable activity is predicted and monitored for the user to perform based on the user's adjusted overall physiological state. In some embodiments, the method includes generating a model representing a user's overall physiological state using (i) measured data for a physiological parameter (e.g., heart rate variability, resting hear rate, and sleep) from a physical sensor of a wearable device worn by the user, (ii) a subjective indication of the user's attitudinal state (or subjective indicators), and (iii) an objective indication of a cognitive or motor function of the user. The cognitive or motor function of the user has a first known variance with respect to the physiological parameter and the user's attitudinal state has a second known variance with respect to the physiological parameter. The method further includes adjusting the model of the user's overall physiological state based on one of the first known variance or the second known variance to determine an adjusted overall physiological state for the user. For example, the method can include reducing or increasing weights given to i, ii, and iii in determining the adjusted overall physiological state. In some embodiments, the method includes substituting in different values for i, ii, or iii that are determined to be more accurate based on comparing the observed variances to the known variances. In some embodiments, the method includes, based on the adjusted overall physiological state, determining an activity for the user to perform in the physical world that is predicted to be suitable for the user based on the adjusted overall physiological state. In some embodiments, a suitable activity is an activity predicted to further improve the adjusted overall physiological score. The method further includes providing a user-interface object on a display of the wearable device that, when selected, causes the wearable device to begin monitoring the user's performance of the activity.

(F2) In some embodiments of (F1), the method further includes redetermining the overall and adjusted physiological states after the user's performance of the predicted activity, then predicting a next activity for the user to perform in the physical world. In some embodiments, the method further includes adjusting the first and second known variances based on data for other users that share physical characteristics with the user. In some embodiments, the predicted activity is integrated with other social features (e.g., the method can include suggesting other people to perform the activity with based on the physiological scores for those other people). In some embodiments, the method further includes an option that allows the user to opt in or opt out of using the social feature.

(F3) In some embodiments of any of (F1)-(F2), the method includes monitoring the user's performance of the predicted activity and suggesting changes in performance of the activity as the adjusted overall physiological state changes during the user's performance of the predicted activity. In some embodiments, the method includes providing haptic feedback via the wrist-wearable device to notify the user of the suggested changes. In some embodiments, the method includes providing visual feedback on the display of the wrist-wearable device to notify the user of the suggested changes.

(F4) In some embodiments of any of (F1)-(F3), the subjective and objective indications are obtained at the same wrist-wearable device that has the physical sensor used to obtain the measured data for the physiological parameter. In some embodiments, the method also includes displaying a user-interface object that, when selected, allows the user to schedule a future time by which to perform the activity.

(F5) In some embodiments of any of (F1)-(F4), data for an additional physiological parameter (e.g., blood pressure, blood oxygen level, skin temperature) is also used in determining the overall and adjusted physiological states. In some embodiments, the overall and adjusted physiological states are further based on background characteristics of the user (e.g., age, gender).

(F6) In some embodiments of any of (F1)-(F5), the method further includes determining whether to update an optimal range of values for the physiological parameter based on i, ii, and iii (shown above in F1), and displaying the optimal range on the display of the wrist-wearable device. In some embodiments, the method determines whether multiple different ranges for different physiological parameters should be updated. In some embodiments each of the physiological parameters includes different known variances, and the method includes updating the adjusted overall physiological state based on these different known variances.

Note that the various embodiments described above can be combined with any other embodiments described herein. The features and advantages described in the specification are not all-inclusive and, in particular, many additional features and advantages will be apparent to one of ordinary skill in the art in view of the drawings, specification, and claims.

BRIEF DESCRIPTION OF THE DRAWINGS

So that the present disclosure can be understood in greater detail, a more particular description may be had by reference to the features of various embodiments, some of which are illustrated in the appended drawings. The appended drawings, however, merely illustrate pertinent features of the present disclosure and are therefore not to be considered limiting, for the description may admit other effective features as the person of skill in this art will appreciate upon reading this disclosure.

FIGS. 3J-3L illustrate a fourth embodiment of a user interface used to display determined qualitative descriptors and associated recommended activities for the user based on the determined qualitative descriptors, in accordance with some embodiments.

FIGS. 6A-6E illustrate different activity metrics monitored by the wrist-wearable device, in accordance with various embodiments.

FIGS. 8A-8E are detailed flow diagrams illustrating a method of determining a qualitative descriptor, in accordance with some embodiments.

Figure 1A:
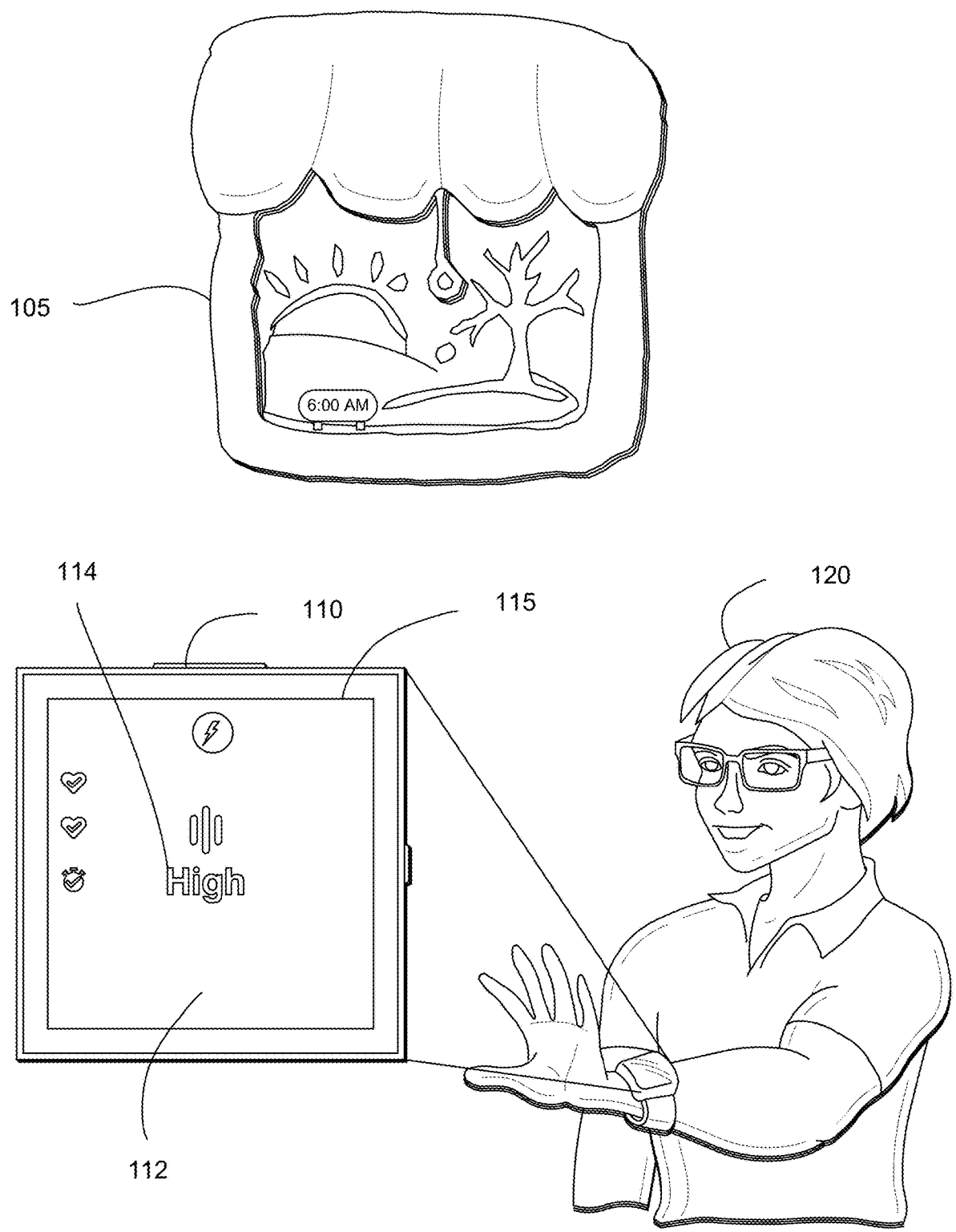
FIGS. 1A-1F illustrate examples of a qualitative descriptor of a user's physiological state presented to a user via a wrist-wearable device, in accordance with some embodiments.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method, or device. Finally, like reference numerals may be used to denote like features throughout the specification and figures.

DETAILED DESCRIPTION

Numerous details are described herein in order to provide a thorough understanding of the example embodiments illustrated in the accompanying drawings. However, some embodiments may be practiced without many of the specific details, and the scope of the claims is only limited by those features and aspects specifically recited in the claims. Furthermore, well-known processes, components, and materials have not been described in exhaustive detail so as to avoid obscuring pertinent aspects of the embodiments described herein.

FIGS. 1A-1F illustrate examples of a qualitative descriptor 112 of a user's physiological state presented to a user 120 via a wrist-wearable device 110 including a display 115, in accordance with some embodiments. In some embodiments, the wrist-wearable device 110 monitors values for a plurality of physiological parameters for a user 120 wearing the wrist-wearable device 110. Each physiological parameter of the plurality of physiological parameters is monitored using one or more sensors (e.g., a heart rate sensor 1058, an EMG sensor 1046, SpO2 sensor 1054; and examples of these and other sensors are shown and described with reference to FIGS. 9A-10) that are in communication with the wrist-wearable device 110. In some embodiments, the physiological parameters include one or more of heart rate (e.g., resting heart rate (RHR), average heart rate, target heart rate (when performing an activity)), heart rate variability (HRV), blood pressure, blood oxygen level, skin temperature, muscle movement, sleep stage (e.g., non-rapid eye movement (NREM) or rapid eye movement (REM) sleep), duration of deep sleep (or duration of sleep within a particular sleep stage or proportion in sleep stages, where deep-sleep duration can be a duration of REM sleep), sleep quantity (e.g., amount of sleep for a particular night), sleep quality (e.g., interrupted or uninterrupted sleep), and other like parameters. Additional data collected by the one or more sensors is described below in reference to FIGS. 9A-10.

In some embodiments, the physiological parameters are monitored by the wrist-wearable device 110, via the one or more sensors, at various time intervals. For example, the wrist-wearable device 110 can monitor the one or more physiological parameters throughout the day (e.g., every two hours, every hour, every half hour, every 15 minutes, every 10 minutes, every five minutes, every two minutes, every minute). In some embodiments, the wrist-wearable device 110 measures the user's 120 physiological parameters while the user 120 is active (e.g., performing an activity such as running, swimming, cycling, or cooking), the user 120 completed an activity, and/or while the user 120 is resting (e.g., sitting, lying down, sleeping).

The wrist-wearable device 110 uses the monitored (or measured) physiological parameters to determine baseline values for the physiological parameters. More specifically, in some embodiments, baseline values for the physiological parameters are determined based on values for the plurality of physiological parameters that were measured over a predetermined period of time. For example, the baseline values for the physiological parameters can be determined based on values for the plurality of physiological parameters that were measured over the past day, the past three days, the past week, the past two weeks, 30 days, two months, etc. The baseline values for the physiological parameters are specific for each particular user 120 wearing the wrist-wearable device 110 but can also be adjusted to account for baseline values associated with other, similarly situated users (e.g., if users opt in to sharing data, then baseline values for one or more other users with similar demographic backgrounds (e.g., age, sex, etc.) can be used to help determine the appropriate baseline values for the user of the wrist-wearable device).

In some embodiments, the predetermined period of time is a period during which the user 120 was in a state of deep sleep. In some embodiments, the wrist-wearable device 110 continually monitors and updates the baseline values for the physiological parameters, while in other embodiments the device determines the baseline values once and does not update them unless the wrist-wearable device goes through a reset process or the user goes through a process to specifically request that the wrist-wearable device obtain new baseline values (e.g., the user provides an input in a "settings" menu on the wrist-wearable device, the input corresponding to a request to obtain new baseline values).

In some embodiments, the baseline values for the physiological parameters are determined as a function of time, such that more than one set of baseline values can be maintained for different time periods. For example, a first set of baseline values for the physiological parameters can be stored for time periods in the morning, while a different second set of baselines values can be maintained for time periods in the middle of the day and a third set of baseline values can be maintained for time periods at night (three sets is just one example; two sets of baselines values can also be used, such as a first set for daytime periods of time and a second set for nighttime periods of time). Additionally, or alternatively, in some embodiments, the baseline values for the physiological parameters are based on different days of the week. For example, the baseline values for the physiological parameters for Monday can be different than the baseline values for the physiological parameters for Thursday. In some embodiments, the baseline values for the physiological parameters are based on the activity being performed or other contextual information. For example, the baseline values for a user 120 playing soccer will differ from the baseline values of a user working at his or her desk. Additionally, or alternatively, in some embodiments, the determined baseline values for the physiological parameters (for each particular user) can be defined for different thresholds (e.g., high, medium, low). For example, favorable baseline values for the physiological parameters can be defined as a high threshold (e.g., eight or more hours of sleep for a particular user 120), average baseline values for the physiological parameters can be defined as a medium threshold (e.g., six to seven hours of sleep for a particular user 120), and less-favorable values for the physiological parameters can be defined as a low threshold (e.g., less than six hours of sleep for a particular user 120). A favorable value can be a value that is within a predefined amount of a corresponding baseline value (e.g., within 15%-20% of the corresponding baseline value). The determination of whether a value qualifies as a favorable value can also depend on the physiological parameter of interest; for instance, a favorable heart rate value can be a value that is below a corresponding baseline heart-rate value by at least a first predetermined amount (e.g., below the baseline by at least 10%-15%, which can reflect that the user is not stressed and is currently relaxed), and a favorable sleep value can be a value that is above a corresponding baseline sleep value by at least a second predetermined amount (e.g., above the baseline by at least 20%-25%, reflecting that the user is well rested).

The above examples of the baseline values for the physiological parameters are non-limiting and simplified for ease of explanation. In embodiments in which different sets of baseline values are used, the wrist-wearable device is also configured to select the appropriate set of baseline values to use in conjunction with the comparisons with measured values for physiological parameters that are used to determine a qualitative descriptor of the user's physiological state (e.g., to select the baseline values associated with mornings when the qualitative descriptor is being determined in the morning).

In some embodiments, the one or more physiological parameters can include objective indications of cognitive or motor functions and subjective indications of the user's current experience or energy level. In some embodiments, the one or more physiological parameters and/or the baseline values discussed above can be adjusted based on subjective indications of the user's physiological state and/or objective indications of a cognitive or motor function of the user 120. In some embodiments, the cognitive or motor function (i.e., the objective indicators) of the user 120 can have a first known variance with respect to one or more of the plurality of physiological parameters and the subjective indications can have a second known variance with respect to one or more of the plurality of physiological parameters. As discussed below in reference to FIGS. 11A-11C, the objective indications are based on objective measurements of the user's current functioning (e.g., motor functioning, cognitive capacity, focus, problem solving, and impulse control) and the subjective indications are based on subjective measurements of the user's current experience (e.g., fatigue, energy, mood, motivation, stress).

The wrist-wearable device 110 compares the values for the plurality of physiological parameters to baseline values for the physiological parameters and determines the qualitative descriptor 112 of the user's 120 physiological state from among a set of three or more predefined qualitative descriptors based on the comparison. In some embodiments, the predefined qualitative descriptors include "high" 114, "medium" 116, and "low" 118 (examples shown in FIGS. 1A-1C). Each qualitative descriptor 112 provides users with an easily understandable and approachable interpretation of their physiological state as it relates to their overall health and energy levels, as described below. These guided user interactions enable users 120 to take appropriate actions based on their current physiological state and save the user time as well, since the descriptors are easy to understand and do not require interpretation. In some embodiments, no more than three predefined qualitative descriptors are used. Alternatively, in other embodiments, no more than six predefined qualitative descriptors are used. A lesser number of predefined qualitative descriptors helps to ensure that the descriptors remain actionable for users 120.

A high 114 qualitative descriptor conveys to users 120 that they have a high energy level (or high fuel level) and/or lower stress compared to the baseline values. In some embodiments, the wrist-wearable device 110 determines a high 114 qualitative descriptor 112 when the measured values for the plurality of physiological parameters are within a predetermined amount (e.g., +/−5%) of favorable baseline values for the physiological parameters (e.g., within a high threshold as described above). For example, the high 114 qualitative descriptor 112 can be provided to users 120 that are determined to be well rested, are engaged, are prepared to take on challenges, have a positive attitude or mood, and/or are energetic. As non-limiting examples, a particular user 120 can be determined to be well rested when measured physiological parameter values for sleep are substantially equal to (or better than) favorable baseline values for sleep (e.g., within the predetermined amount of the high threshold values as determined for the user 120 (e.g., at least seven hours of sleep or better, uninterrupted sleep)); the particular user 120 can be determined to be engaged when measured physiological parameter values for objective measurements of the user's current functioning (as described below in FIGS. 11B and 11C) are substantially equal to (or better than) favorable baseline values of the user's current functioning (e.g., within the predetermined amount of the high threshold values as determined for the user 120 (e.g., a high score in an anagram score as discussed below in reference to FIG. 11C)); the particular user 120 can be determined to be prepared to take on challenges and/or have a positive attitude or mood when measured physiological parameter values for subjective measurements of the user's current experience (as described below in FIG. 11A) are substantially equal to (or better than) favorable baseline values of the user's current experience (e.g., within the predetermined amount of the high threshold values as determined for the user 120 (e.g., positive user inputs in a visual analogue scale (VAS) as discussed below in reference to FIG. 11A)); and/or the particular user 120 can be determined to be energetic when overall measured physiological parameter values for the user are substantially equal to (or better than) favorable baseline values for the user 120 overall (e.g., within the predetermined amount of the high threshold values for the plurality of physiological parameters (e.g., heart rate, sleep, stress) as determined for the user 120).

A medium 116 qualitative descriptor conveys to users 120 that they have a medium energy level (or medium fuel level) and/or substantially average stress compared to the baseline values. In some embodiments, the wrist-wearable device 110 determines a medium 116 qualitative descriptor 112 when the measured values for the plurality of physiological parameters are within the predetermined range of average baseline values for the physiological parameters (e.g., within the predetermined amount of a medium threshold as described above). For example, the medium 116 qualitative descriptor 112 can be provided to users 120 that are determined to be moderately rested, have moderate energy, have consistent engagement, and/or have a level attitude or mood. As non-limiting examples, a particular user 120 can be determined to be moderately rested when measured physiological parameter values for sleep are substantially equal to (or better than) average baseline values for sleep; the particular user 120 can be determined to be engaged when measured physiological parameter values for objective measurements of the user's current functioning are substantially equal to (or better than) average baseline values of the user's current functioning; the particular user 120 can be determined to be prepared to take on challenges and/or have a positive attitude or mood when measured physiological parameter values for subjective measurements of the user's current experience are substantially equal to (or better than) average baseline values of the user's current experience; and/or the particular user 120 can be determined to be energetic when overall measured physiological parameter values for the user are substantially equal to (or better than) average baseline values for the user 120 overall.

A low 118 qualitative descriptor 112 conveys to users 120 that they have a lower energy level (or low fuel level) and/or higher stress level compared to the baseline values. In some embodiments, the wrist-wearable device 110 determines a low 118 qualitative descriptor 112 when the measured values for the plurality of physiological parameters are within the predetermined amount of less favorable baseline values for the physiological parameters (e.g., within the predetermined amount of a low threshold as described above). For example, the low 118 qualitative descriptor 112 can be provided to users 120 that are determined to be tired, sluggish, unmotivated, disengaged with work and/or activities, and/or stressed. As non-limiting examples, a particular user 120 can be determined to be tired when measured physiological parameter values for sleep are substantially equal to (or worse than) less favorable baseline values for sleep; the particular user 120 can be determined to be engaged when measured physiological parameter values for objective measurements of the user's current functioning are substantially equal to (or worse than) less favorable baseline values of the user's current functioning; the particular user 120 can be determined to be prepared to take on challenges and/or have a positive attitude or mood when measured physiological parameter values for subjective measurements of the user's current experience are substantially equal to (or worse than) less favorable baseline values of the user's current experience; and/or the particular user 120 can be determined to be energetic when overall measured physiological parameter values for the user are substantially equal to (or worse than) less favorable baseline values for the user 120 overall.

The predetermined amount provided above is non-limiting and provided as an example. The predetermined amount can be based on the specific physiological parameter. As described above, in some embodiments, the baseline values for the physiological parameters are determined for the user 120 over time. In some embodiments, each of the plurality of physiological parameters is compared individually. For example, heart rate, blood pressure, and sleep durations can each be individually compared to corresponding baseline values for each of those physiological parameters to determine the qualitative descriptor 112. In some embodiments, the individual comparisons are each (and collectively) used to determine the qualitative descriptor 112; other embodiments can use one or more (but not necessarily all) of the individual comparisons to determine the qualitative descriptor 112. The various comparisons can also be weighted such that a comparison of one physiological parameter is given more weight than a comparison involving a different physiological parameter (e.g., comparison involving comparing measured heart rate to an associated baseline heart rate value can be weighted at 55% when the user is known to be exercising, while comparing measured sleep data to an associated baseline sleep-data value can be weighted at a lower percentage when the user is known to be exercising).

In some embodiments, respective baseline values for each physiological parameter are compared to measured values (for the corresponding/same physiological parameter as the baseline value) to determine how far above or below the measured values are as compared to the relevant baseline values, and then determine which qualitative descriptor is appropriate. For example, if two of three measured values for the physiological parameters are above the associated baselines by the predetermined amount (e.g., 5%), then a high 114 qualitative descriptor is conveyed to the user 120. Alternatively, if one of three measured values for the physiological parameters is above associated baselines by the predetermined amount, then a medium 116 qualitative descriptor is conveyed to the user 120. As one more example, if zero of three measured values for the physiological parameters are above the associated baselines by the predetermined amount, then a low 118 qualitative descriptor is conveyed to the user 120.

As one other non-limiting example of determining the qualitative descriptor 112, the qualitative descriptor 112 can be based on the measured physiological parameters being within more or less than one standard deviation of normalized baseline values for the physiological parameters; based on high, medium, and low threshold for the baseline values as described above; based on percentage or discrete pre-defined amounts above or below the baseline values, etc.

In some embodiments, the one or more predefined qualitative descriptors 112 are actionable and non-numeric descriptors that have been discovered by the inventors as descriptors that cause users 120 to quickly recognize and understand their current physiological states. Each qualitative, non-numeric, and actionable qualitative descriptor 112 can also be referred to herein as a fuel or energy level for the user—as compared to a numerical value, which can be difficult to understand as it can be hard to appreciate the differences between, e.g., a score (such as a fuel score) of 95 as compared to a score (such as a fuel score) of 85. By comparison, the intentionally limited qualitative and actionable descriptors (e.g., just three qualitative descriptors) of physiological states as described herein have undergone experimental user studies to ensure that the descriptors are readily understandable by users, enabling those users to have a quick understanding of their current physiological state by simply reading the descriptor. The inventors have discovered that displaying only the qualitative, actionable descriptor helps to ensure that users can quickly understand their energy levels and, as such, the presentation of the qualitative descriptors 112 is presented without displaying a numeric representation of the users' physiological state. Examples of the qualitative descriptors are provided below in reference to FIGS. 2A-30.

In some embodiments, the comparison of the values for the plurality of physiological parameters to the baseline values for the physiological parameters is conducted using a machine-learning model that is trained using the baseline values for the physiological parameters. For example, the machine-learning model can be trained using a user's baseline values for the physiological parameters from the last seven days, last 14 days, last 30 days, etc. In some embodiments, the machine-learning model is further trained using subjective indications of the user 120's physiological state and objective indications of a cognitive or motor function of the user 120 (which can be determined at times similar to when the physiological parameters are measured, to ensure that the machine-learning model is able to learn and account for known relationships between measured physiological parameters and these objective and subjective indications). The subjective indications and the objective indications are discussed in detail below in reference to FIGS. 11A-11C.

In some embodiments, the wrist-wearable device 110 is in communication with the display 115, which presents the qualitative descriptor 112 to the user 120. In some embodiments, the qualitative descriptor 112 is displayed without a numeric score representing the user's physiological state. For example, as shown in FIGS. 1A-1F, the qualitative descriptors include the predefined qualitative descriptors high 114, medium 116, and low 118 without any numerical indicators. In some embodiments, the qualitative descriptor is presented on the display 115 with text, one or more background colors, and/or icons as described below in reference to FIGS. 2A-2C.

In some embodiments, the qualitative descriptor 112 is presented using an application (e.g., a health-related application managed by an operating system that is built by a same manufacturer of the wrist-wearable device) of the wrist-wearable device 110. In some embodiments, on first launch of application, the wrist-wearable device 110 provides, via the display 115, a description of how determinations of qualitative descriptors of the user's physiological state are made and explains research behind these determinations. In other words, in some embodiments a description explaining the determination of the qualitative descriptor 112 and/or the one or more physiological parameters used to make the qualitative descriptor 112 determinations are presented to the user 120 via the display 115. In some embodiments, the description presented via the display 115 includes information about metrics collected. For example, the display 115 can present an explanation of how the detected heart rate and detected sleep pattens compare to expected results (e.g., baseline values for the physiological parameters) as shown and described in FIGS. 3A-4B. Some embodiments also allow users to opt out and instruct the device to cease monitoring one or more of the physiological parameters, should they desire to do so.

Figure 1B:
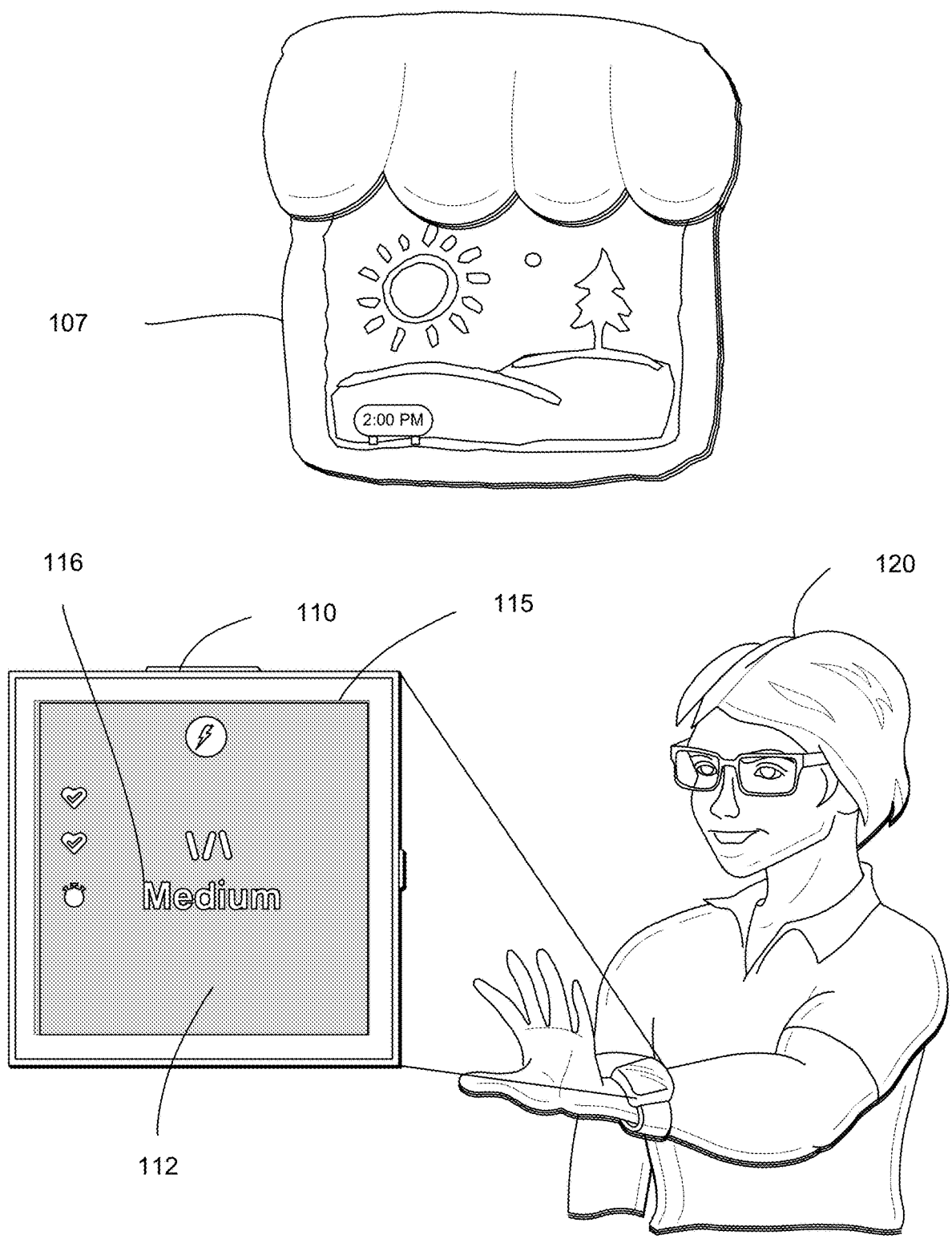
Figure 1C:
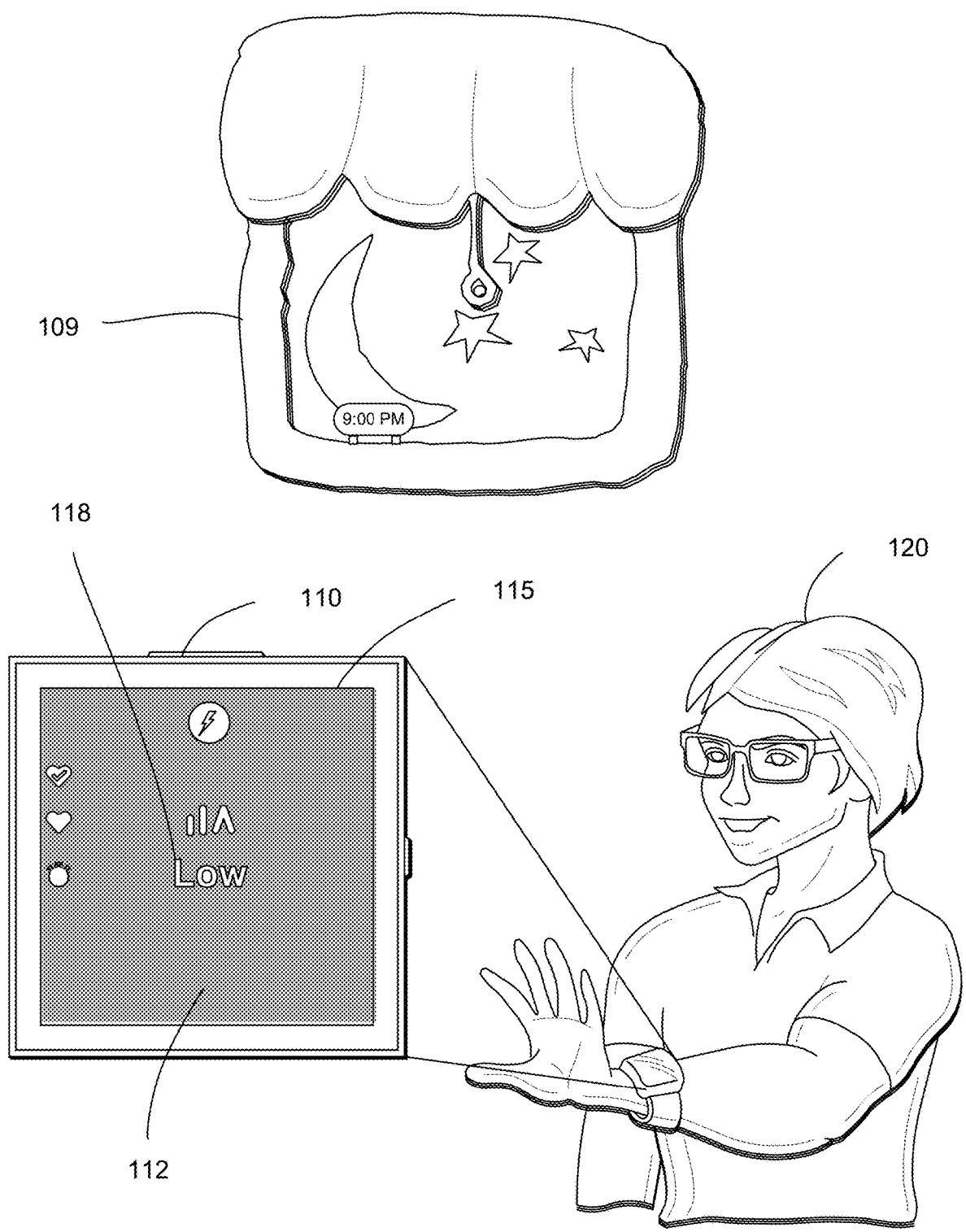

Turning to FIGS. 1A-1C, a change in a qualitative descriptor 112 that is presented to the user 120 as the day goes on is illustrated. For example, in FIG. 1A, the display 115 of the wrist-wearable device 110 presents a high 114 predefined qualitative descriptor early in the morning 105 (e.g., 6:00 AM). In this example, the wrist-wearable device 110 determines that the user 120 had a good night's sleep and woke up refreshed, resulting in favorable values for the physiological parameters, and thus presents a high 114 qualitative descriptor indicative of the user 120's high fuel level (e.g., energy level). In FIG. 1B, the user 120 may move into a lower fuel level as the day progresses. For example, during the afternoon 107 (e.g., 2:00 PM), the wrist-wearable device 110 can update/redetermine the qualitative descriptor 112 and present, via the display 115, a medium 116 predefined qualitative descriptor indicating the user 120's moderate fuel level. As described above, in some embodiments a determination of the qualitative descriptor 112 is based on a comparison of the user 120's current measured physiological parameters to the baseline values; as such, in FIG. 1B, the change in the qualitative descriptor 112 is based on a change in the user's monitored physiological parameters from favorable values to average values. In FIG. 1C, it is nighttime 109 (e.g., 9:00 PM) and the qualitative descriptor 112 changes again. In particular, the wrist-wearable device 110 determines that the user 120 is tired and has less favorable values for the physiological parameters, and thus presents a low 118 predefined qualitative descriptor indicative of the user 120's low fuel level. The new (or updated) qualitative descriptors of the user's physiological state can be presented without displaying a numeric score representing the user's physiological state.

FIGS. 1A-1C are provided as non-limiting examples. Different actions that a user 120 performs throughout the day can increase or decrease the user's determined fuel level and the displayed qualitative descriptor 112. For instance, the user 120 could have taken a nap at noon, which could result in a high fuel level at night. In some embodiments, as discussed below in reference to FIGS. 3A-3C, the wrist-wearable device 110 determines and presents, via the display 115, one or more recommended activities to the user 120 to perform in the physical world that can positively affect the user 120's fuel level (e.g., assist recovery, reduce stress, burn excess energy), thereby helping to encourage users to take actions to improve their physiological states (thereby pushing the user to achieve more desirable qualitative descriptors of the user's physiological states).

Figure 1D:
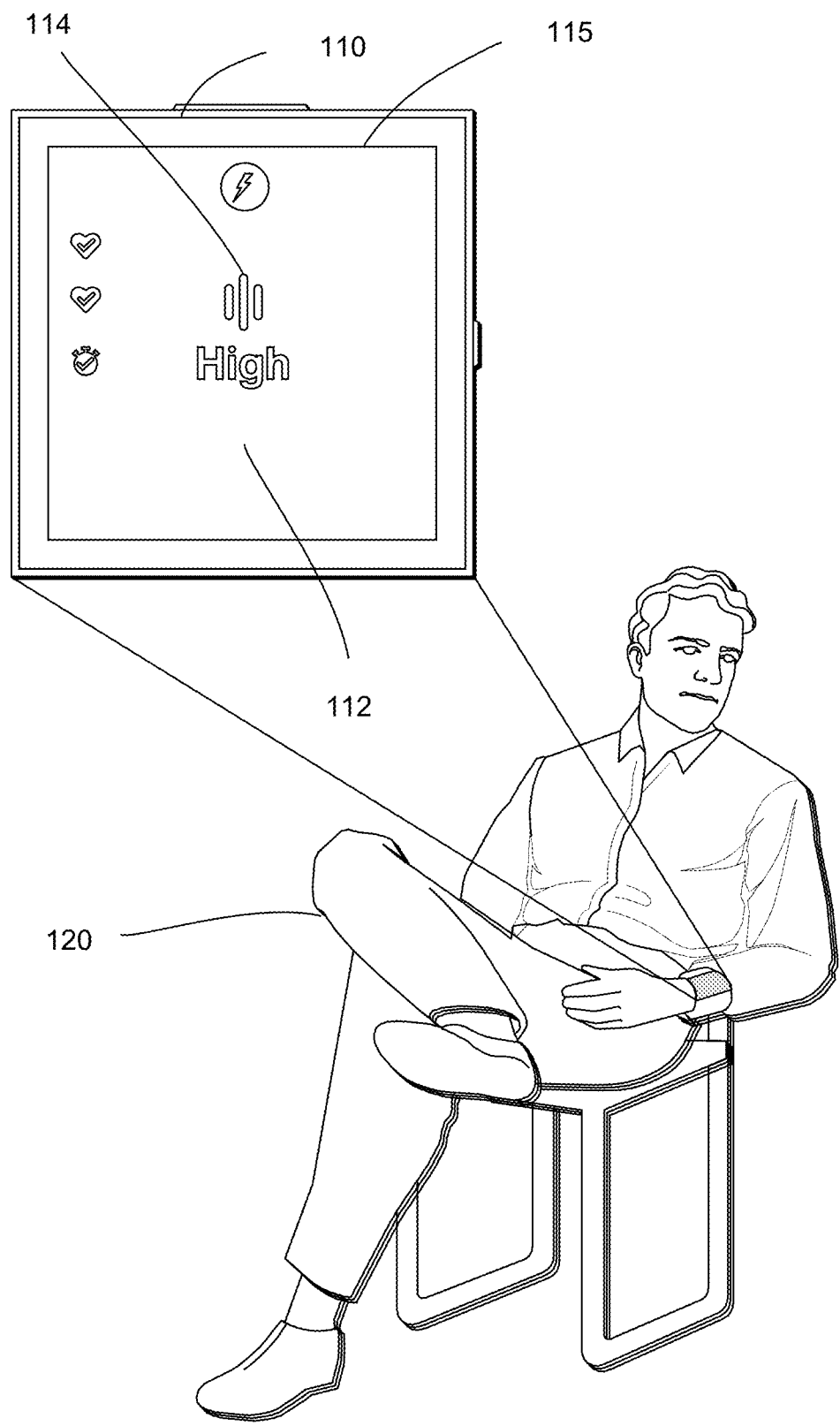
Figure 1E:
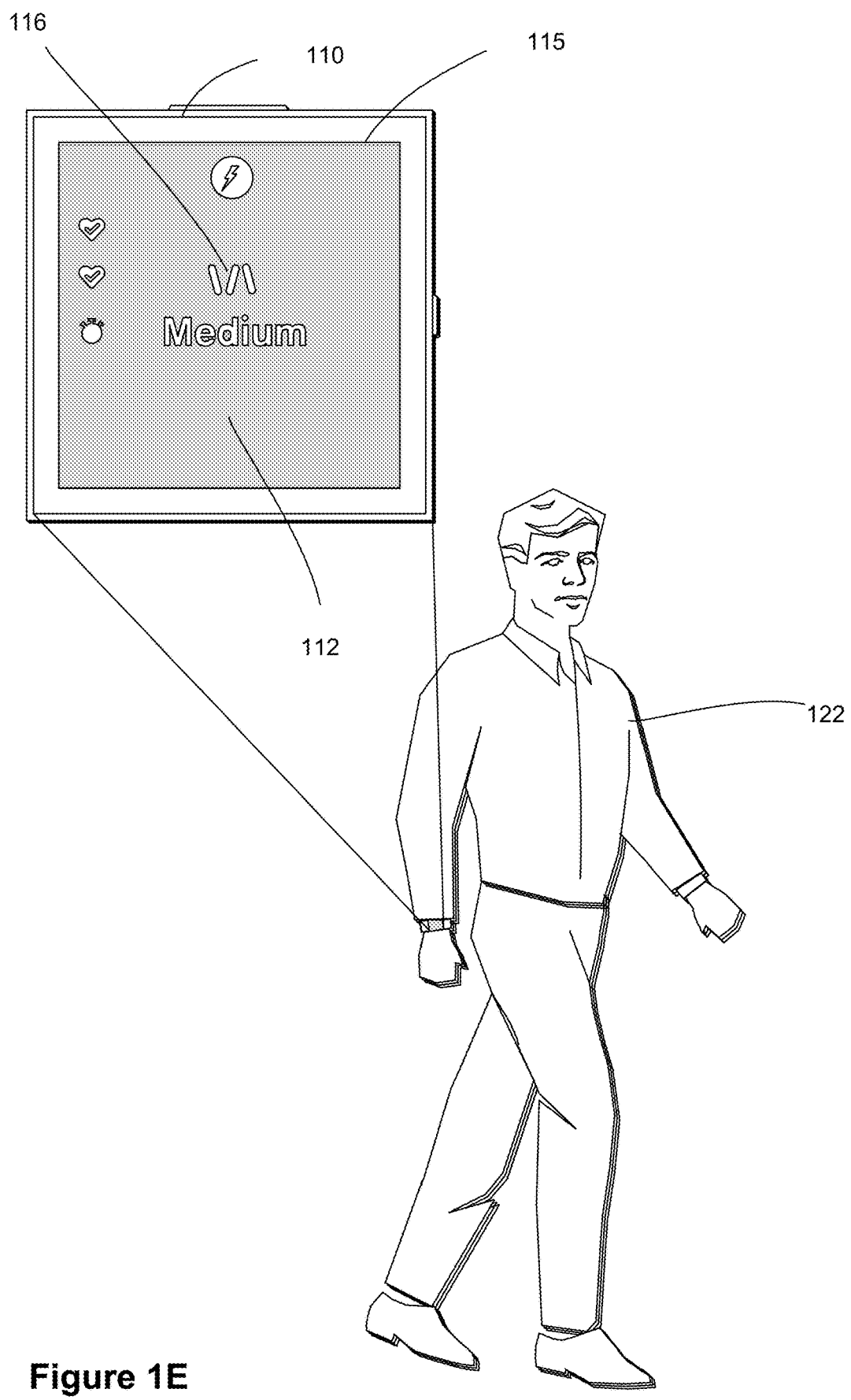
Figure 1F:
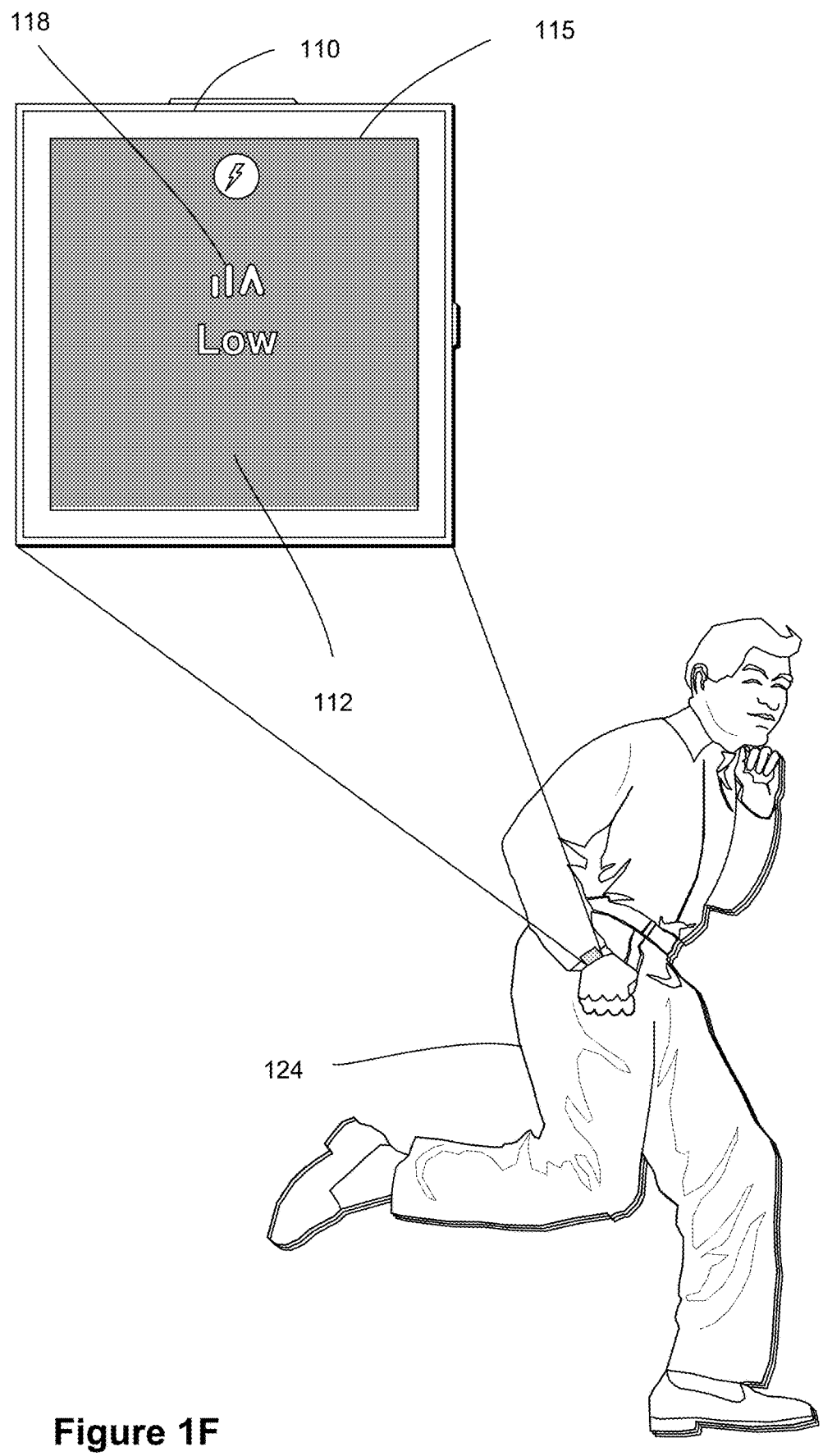

In some embodiments, the qualitative descriptor 112 is updated based on one or more activities performed by the user 120. For example, as shown in FIGS. 1D-1F, the qualitative descriptors 112 are updated after the user 120 has performed an activity (and, after performance of the activity, the device uses new comparisons of values of monitored physiological parameters to the baselines values to then select a new qualitative descriptor of a predetermined number (e.g., three) of qualitative descriptors as reflect the user's new physiological state after performance of the one or more activities). Additionally, or alternatively, in some embodiments the qualitative descriptors 112 are updated while the user 120 is performing an activity. In some embodiments, the wrist-wearable device 110 monitors the user 120's performance of the activity. Alternatively, in some embodiments the wrist-wearable device 110 begins to monitor the user 120's performance of the activity in response to the user 120's selection of a user-interface object corresponding to an activity to be performed by the user 120. In addition to or as an alternative to determining new qualitative descriptors of the user's physiological state after the user performs a physical activity, the wrist-wearable device 110 described herein can also continuously monitor values for the plurality of physiological parameters and make updated physiological-state determinations when a pattern representing a change in one of the physiological parameters is detected (e.g., a pattern of low hours of sleep (e.g., 3-4 hours), a pattern of elevated or decreased heart rate variability).

The wrist-wearable device 110 can also determine new qualitative descriptors on a fixed schedule (e.g., once per day, such as when a user wakes up; or twice per day, such as when a user wakes up and when a user is getting ready for bed) and/or on dynamic schedules that can be configured by a user or that can be learned by the system based on physical activity patterns of the user. For instance, the wrist-wearable device 110 can learn the times at which the user exercises and make new qualitative descriptor determinations for a predetermined period of time (e.g., 10-30 minutes) before the user is predicted to become active (e.g., exercising).

In some embodiments, as discussed below in reference to FIGS. 3A-3O, the wrist-wearable device 110 determines one or more activities for the user 120 to perform in the physical world, which activities are predicted to be suitable for the user 120 based on the qualitative descriptor (medium 116) of the user 120's physiological state.

Based on a comparison of the new values for the physiological parameters to the baseline values for the physiological parameters, the wrist-wearable device 110 determines a new qualitative descriptor (medium 116) of the user's physiological state from among the set of three or more predefined qualitative descriptors. The wrist-wearable device 110 presents, on the display 115 that is in communication with the wrist-wearable device 110, the new qualitative descriptor (medium 116) of the user's physiological state without displaying a numeric score representing the user 120's physiological state.

For example, FIG. 1D illustrates a user 120 relaxing by sitting in a chair. In this example, the display 115 of the wrist-wearable device 110 displays a high 114 predefined qualitative descriptor 112 as the user 120 is not performing an activity and is determined to be calm, which results in favorable measured physiological parameters. In this example, the user 120's physiological parameters (e.g., heart rate, breathing, stress) are favorable (e.g., at a high threshold relative to the baseline values for the physiological parameters), which results in the high 114 predefined qualitative descriptor.

In FIG. 1E, the display 115 shows an updated predefined qualitative descriptor of medium 116 after the user 120 performs a first activity 122 (e.g., walking). In this example, one or more newly measured physiological parameters (after or during the walk) when compared to the baseline values for the physiological parameters are determined to indicate a medium energy level for the user, which results in presentation of the medium 116 predefined qualitative descriptor. In some embodiments, medium energy level results from the walk exhausting and/or stressing the user 120 (e.g., a fast-paced walk that places the user 120's physiological parameters within medium thresholds or values, or a walk with a colleague who conveyed difficult or distressing news to the user, resulting in a decrease in the values for the user's physiological parameters relative to the user's associated baselines).

As a different example, if the user starts with a low energy level (example in FIG. 1F), medium energy level depicted in FIG. 1E can be achieved after a walk that rejuvenates and/or calms the user 120 (e.g., a slow-to moderate-paced walk that places the user 120's physiological parameters within the medium thresholds or values).

In some embodiments, and turning to FIG. 1F, the display 115 shows another updated predefined qualitative descriptor of low 118 after the user 120 performs a second activity 124 (e.g., running). In this example, one or more newly measured physiological parameters (after or during the run), when compared to the baseline values for the physiological parameters, indicate that the user has a low energy level, which results in the presentation of the low 118 predefined qualitative descriptor. The determination of a low energy level can result from the run exhausting, overexerting, and/or stressing the user 120 (e.g., the run causing the user 120's physiological parameters to drop relative to the associated baseline values).

A non-exhaustive list of activities includes meditating, resting (e.g., sleeping, napping, sitting), walking, breathing exercise, and working out (e.g., running, biking, lifting weights, swimming). Performance of the one or more activities can cause the wrist-wearable device 110 to update the qualitative descriptor to a higher or lower qualitative descriptor 112 based on changes in monitored values for physiological parameters due to performance of the activity, as discussed further in detail below in reference to FIGS. 3A-3O.

Figure 2A:
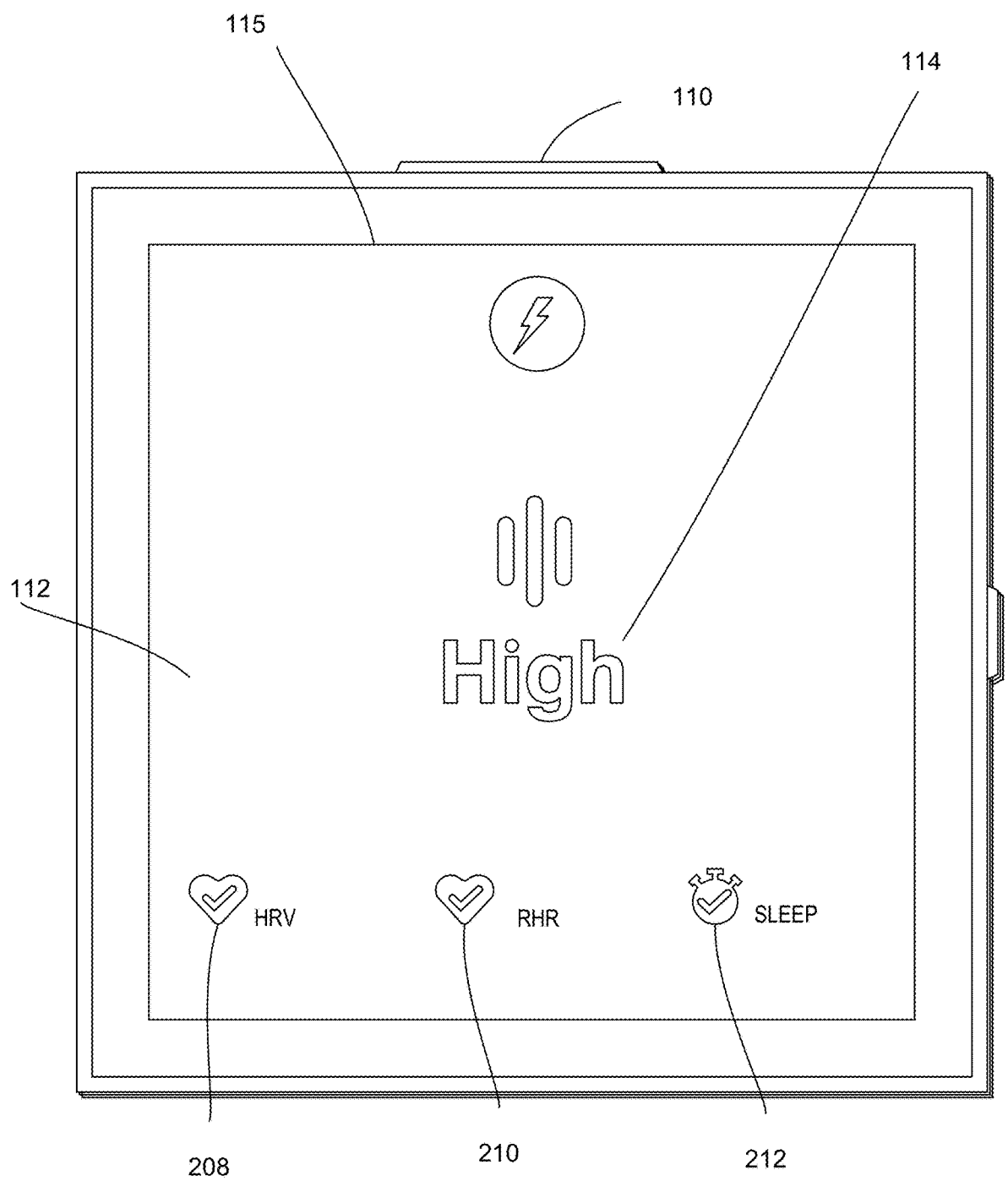
FIGS. 2A-2C illustrate examples of a wrist-wearable device presenting qualitative descriptors of a user's physiological state, in accordance with some embodiments.
Figure 2B:
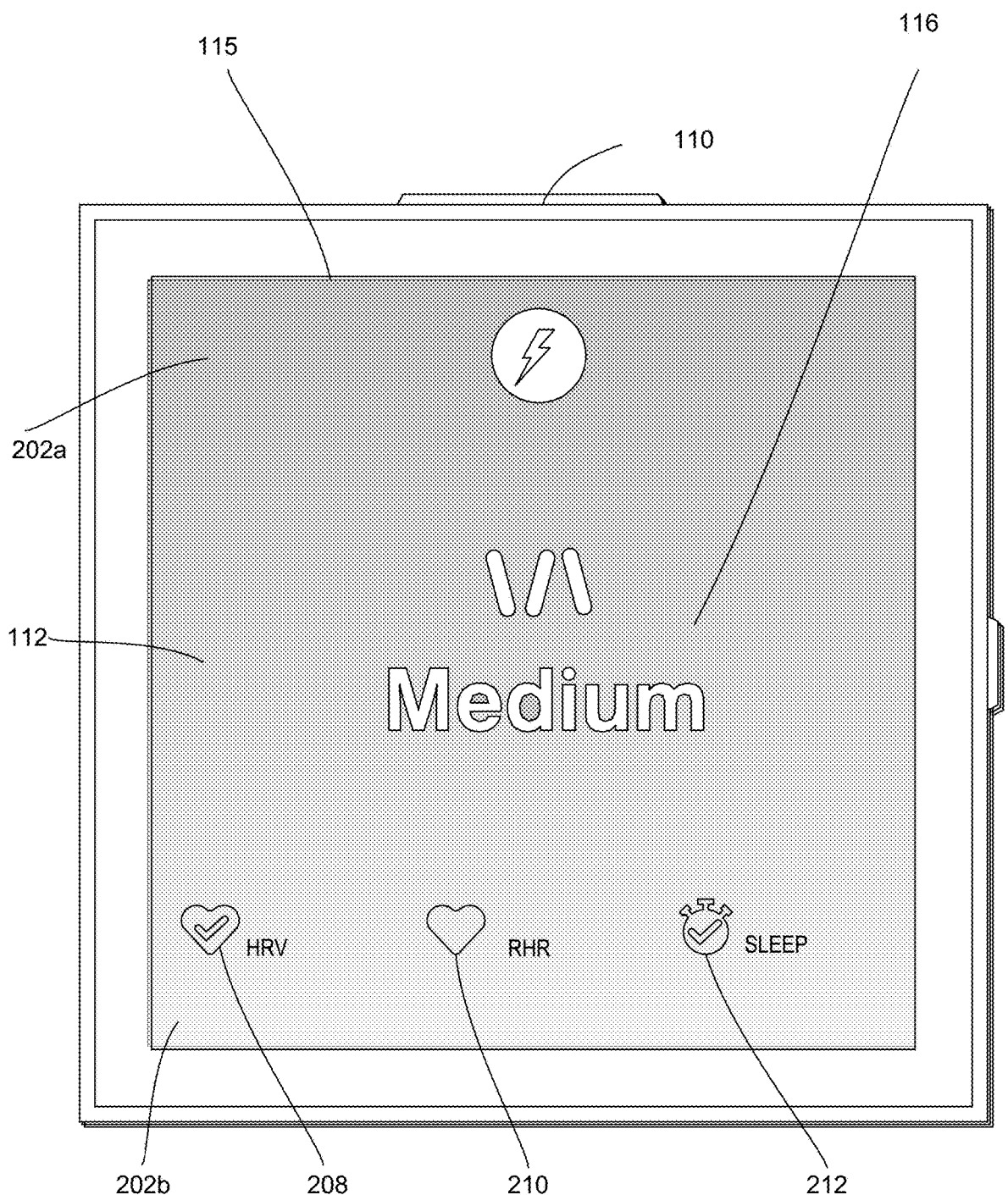
Figure 2C:
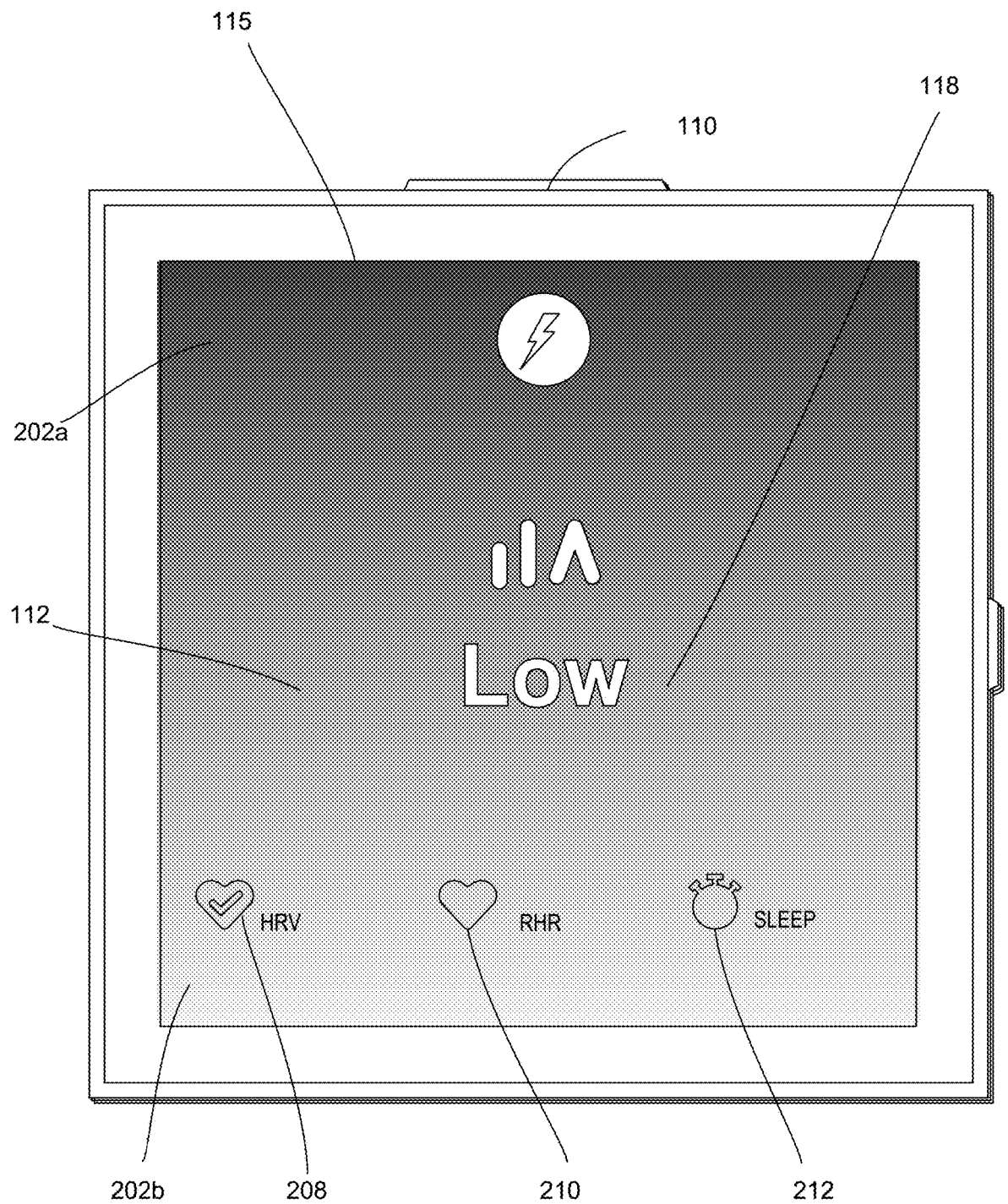

FIGS. 2A-2C illustrate examples of a wrist-wearable device 110 presenting actionable qualitative descriptors 112 of a user's physiological state, in accordance with some embodiments. In some embodiments, wrist-wearable device 110 includes display 115 that provides the user with a predefined qualitative descriptor (e.g., high 114, medium 116, low 118) and/or actionable descriptor of the user's physiological state. In some embodiments, the display 115 is physically coupled with the wrist-wearable device 110 (in other words, the same device that determines the appropriate qualitative descriptor of the user's physiological state also uses its own display to provide a representation of that qualitative descriptor of the user's physiological state). Examples of the wrist-wearable device 110 are provided below (in FIGS. 9A and 9B). In some circumstances, in addition to using its own display 115, the qualitative descriptor can additionally be presented on a display of another device (distinct from the wrist-wearable device 110) that is communicatively coupled with the wrist-wearable device 110, such as a user's smartphone, laptop, tablet, artificial-reality glasses, smart glasses, smart contacts (or eye-wearable artificial-reality devices), virtual-reality head-mounted display, etc. One or more predefined qualitative descriptors and/or actionable descriptors are actionable and non-numeric descriptors, which have been discovered by the inventors as descriptors that cause users to quickly recognize and understand their current physiological states. For example, the one or more predefined qualitative descriptors and/or actionable descriptors can be displayed with one or more of text, colors, icons, and symbols as described below, which can further the user's ability to quickly determine appropriate actions to take. Each qualitative, non-numeric, and actionable qualitative descriptor can also be referred to herein as a fuel or energy level for the user.

In some embodiments, the wrist-wearable device 110 monitors, via one or more sensors (FIGS. 9A-10) that are in communication with the wrist-wearable device 110, values for a plurality of physiological parameters for a user 120 wearing the wrist-wearable device 110. In some embodiments, each sensor of the one or more sensors is physically coupled with the wrist-wearable device 110—for example, either via a capsule portion or watch body 954 and/or a band portion or watch band 962 of the wrist-wearable device shown below in reference to FIG. 9A. Additionally, or alternatively, in some embodiments one or more sensors 964 and 965 can be in communication with the wrist-wearable device 110 but not physically coupled with it. For example, in some embodiments the wrist-wearable device 110 is communicatively coupled to one or more heart-rate monitors and/or GPS.

In some embodiments, the qualitative descriptor 112 that is presented on the display 115 includes textual descriptions. For example, the qualitative descriptor 112 can indicate whether the user 120's current physiological state is high 114, medium 116, or low 118 (examples in each of FIGS. 2A-2C, respectively). As depicted in FIGS. 3A-3O, the presented qualitative descriptor 112 can also include textual status words (e.g., "Go for it" 302) and/or messages ("Your fuel is looking good" 304) that are configured to motivate the user 120 and/or encourage the user 120 in an actionable way throughout the day. The messages and/or status words can be presented with different text, kerning, font, font size, and color, which can be selected to ensure that users can have a quick understanding of their current physiological state by simply reading the descriptor and its surrounding context on the display.

As one example, the qualitative descriptor 112 is presented on the display 115 along with a background color associated with the qualitative descriptor 112. In some embodiments, each respective qualitative descriptor for the set of three or more predefined qualitative descriptors (e.g., high 114, medium 116, and low 118) is associated with a different background color. As non-limiting examples, the different white and grey background colors used in FIGS. 2A-2C illustrate that three different colors can be displayed in conjunction with each of the three different predefined qualitative descriptors. In particular, FIG. 2A shows that a first color (e.g., green) can be associated with a first or high 114 predefined qualitative descriptor (e.g., associated with a high energy or fuel level); FIG. 2B shows that a second color (e.g., blue) can be associated with a second or medium 116 predefined qualitative descriptor (e.g., associated with a medium energy or fuel level); and FIG. 2C shows that a third color (e.g., purple) can be associated with a third or low 118 predefined qualitative descriptor (e.g., associated with a low energy or fuel level).

In some embodiments, the colors are selected based on data obtained from user studies to ensure that the colors are calming and soothing to users, and the colors can be displayed with a gradient treatment such that more color is present in a certain portion of the display relative to other portions of the display (e.g., as shown in FIGS. 2B-2C, the most color is present in an upper/top portion 202*a* of the display 115 and gradually less color is displayed in a bottom/lower portion 202*b* of the display 115).

Additionally, or alternatively, in some embodiments presenting the qualitative descriptor 112 on the display 115 also includes presenting information to the user 120 regarding the values for the plurality of physiological parameters to provide the user with information as to how the qualitative descriptor was determined. As one example, FIGS. 2A-2C show that the display 115 can also present representations of at least three different physiological parameters (e.g., icons representing HRV 208, RHR 210, and Sleep 212, respectively) along with an indication of whether the user's value for that physiological parameter is within an expected range (e.g., whether each icon is filled in or empty, as shown in the examples of FIGS. 2A-2C). Additional or alternative indications of whether the user's values for physiological parameters are within expected ranges (or not) include highlighted, checked, bolded, etc., icons. As described above, a user 120's physiological parameters can be determined to be within expected ranges (or not) based on a comparison of values measured for the physiological parameters with baseline values.

Although FIGS. 2A-2C show indicators for three different physiological parameters, more than three physiological parameters can be used to determine the qualitative descriptor, as was mentioned above. Further, as shown between FIGS. 1A-2C, the representations of three different physiological parameters (e.g., icons representing HRV 208, RHR 210, and Sleep 212, respectively) can be presented on different portions of the display 115.

In some embodiments, the icons representing HRV 208, RHR 210, and Sleep 212 can be updated in real time. As described above in reference to FIGS. 1A-1F, in some embodiments the wrist-wearable device 110 monitors values for the user's physiological parameters while the user is performing an activity (e.g., reading, sleeping, running, working) via the one or more sensors that are in communication with the wrist-wearable device 110. In some embodiments, new values for the plurality of physiological parameters for the user wearing the wrist-wearable device 110 are determined based on the monitored activity. The new values for the plurality of physiological parameters can be compared to the baseline values for the physiological parameters and, in addition to being used to select a qualitative descriptor of the user's physiological state from among a predefined number (e.g., three) of predefined qualitative descriptors, can be used to update the icons representing HRV 208, RHR 210, and Sleep 212 (along with the qualitative descriptor 112) to reflect results of the comparisons.

Figures 3A, 3B, 3C:
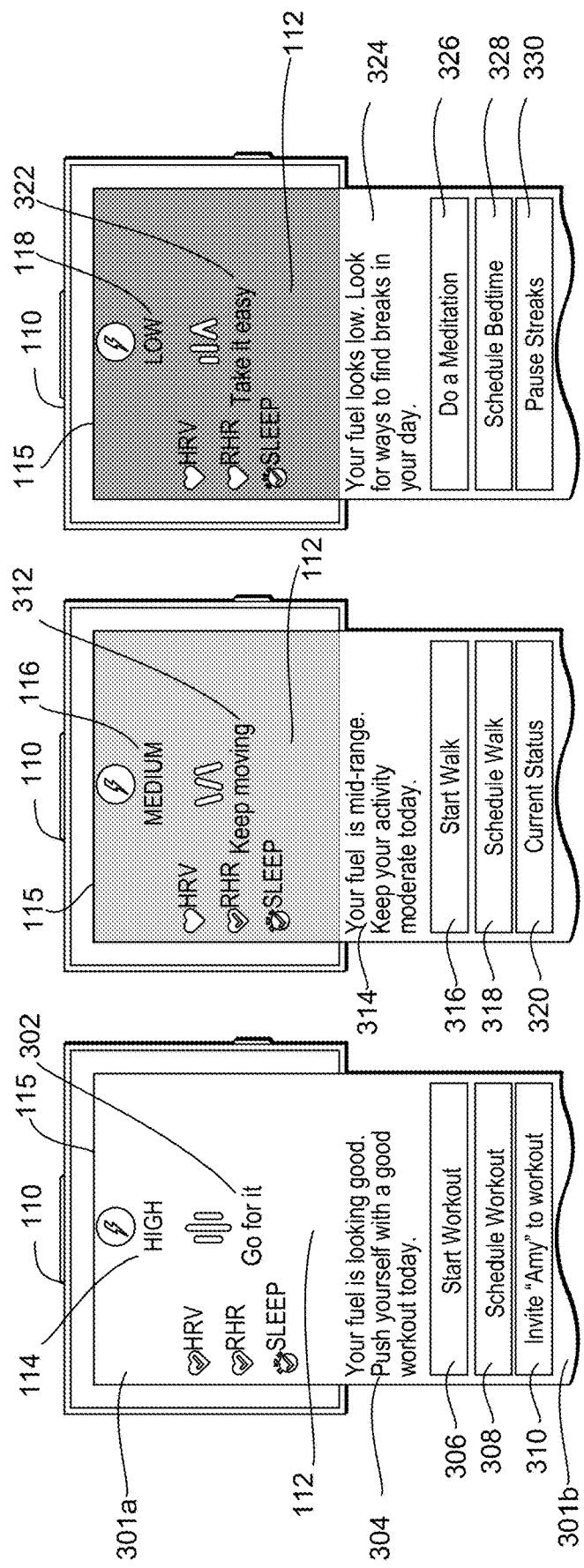
FIGS. 3A-3C illustrate a first embodiment of a user interface used to display determined qualitative descriptors and associated recommended activities for the user based on the determined qualitative descriptors, in accordance with some embodiments.

FIGS. 3A-3C illustrate a first embodiment of a user interface used to display determined qualitative descriptors and associated recommended activities for the user based on the determined qualitative descriptors, in accordance with some embodiments. As mentioned above in reference to FIGS. 2A-2C, in some embodiments the qualitative descriptor is displayed alongside messages and/or status words that readily communicate to a user 120 his or her current physiological state and/or provide the user with actionable descriptors that are used to encourage, motivate, and/or coach a user 120 in performing an activity and/or carrying out his or her day. For example, status words such as "Go for it," "Seize," "Drive," etc., can be provided to users studying or working to encourage them as they work and to encourage them to keep focus, and can change to remind the user to keep pushing forward (e.g., "keep moving") or remind the user to take a break (e.g., "Take it easy"). As discussed below, the messages can also be updated accordingly.

In some embodiments, while the qualitative descriptor 112 of the user's physiological state is displayed in a first portion 301 of a user interface on a display 115 of a wrist-wearable device 110, a touch-based user input (e.g., a scrolling input received while the user moves his or her finger across the display in a substantially downward direction; or, in a different example, a single tap from a finger of the user) is detected within the first portion 301 of the user interface. In some embodiments, in response to the user input within the first portion 301*a* of the user interface, an additional portion 301*b* of the user interface that includes one or more user interface objects is displayed.

In some embodiments, the one or more interface objects include one or more activities for the user 120 to perform in the physical world, the activities predicted to be suitable for the user 120 based on the determined qualitative descriptor 112 of the user 120's physiological state. Suitable activities can be activities predicted to be appropriate for the user 120 while the qualitative descriptor of the user's physiological state continues to apply. For example, if the qualitative descriptor of the user's physiological state is within one of the categories indicating that the user has a lower fuel level, then the determined activity can be predicted to be suitable for the user because it will help to further improve the user's energy/fuel level, which should help to move the user to a higher fuel level. Example activities presented to the user are described below. In some embodiments, the additional portion 301*b* of the user interface includes respective user interface elements associated with each of at least two activities determined for the user to perform in the physical world (such that, after selection of a respective user interface element associated with a particular activity, the device begins to monitor the user's performance of the particular activity (and can cease to display the qualitative descriptor and instead switch to a health-monitoring user interface)).

Turning to FIG. 3A, a high 114 qualitative descriptor 112 can be displayed with first status words 302 "Go for it" and a first message 304 that states "Your fuel is looking good. Push yourself with a good workout today," which are provided to a user 120 to motivate the user 120 and/or encourage the user 120 to challenge himself or herself throughout the day. As described above, the user 120 can be presented an additional portion 301*b* of the user interface (in response to the user input within the first portion 301*a*) that includes one or more user interface objects associated with one or more determined activities for the user 120 to perform in the physical world. In some embodiments, because the user 120's determined qualitative descriptor 112 is high 114 (e.g., the user 120's current physiological state is healthy and/or energetic), the wrist-wearable device 110 determines high-energy activities that the user can perform to take advantage of his or her current physiological state, such as performing a physical workout at the gym, going for a run, etc. In FIG. 3A, the user 120 is presented with a first interface object 306 to start a workout, a second user interface object 308 to schedule performance of the workout at a future time, and a third user interface object 310 to invite at least one other user to perform the workout with the user.

In some embodiments, displaying the additional portion of the user interface also includes presenting on the display 115 an explanation as to why the activity has been selected as appropriate for the user 120. For example, the status words (e.g., first status words 304) can be provided to the user 120 as an explanation that includes a short description as to why the activity has been selected as appropriate for the user 120 (e.g., "Your fuel is looking good. Push yourself with a good workout today."). By including such short descriptions alongside the suggested activity, the system described herein helps to ensure that users 120 have insights into the recommendations, which helps users to trust and follow the recommended actions over time, rather than ignore them. Additional example short explanations are also shown in FIGS. 3B-5C (described below).

In some embodiments, the wrist-wearable device 110 receives a selection of the user interface object from within the additional portion 301b and, in response to the selection of the user interface object, causes performance of an action (corresponding to the user interface object) based on the selection. For example, the wrist-wearable device 110, in response to the selection of the first interface object 306, begins to monitor the user's performance of the workout. In some embodiments, the user 120 can specify the workout he or she will perform (e.g., lifting weights, running, golfing). Alternatively, in some embodiments, the wrist-wearable device 110 automatically recommends a workout to the user (e.g., Start Cycling Workout). The recommended workout can be based on the user's preferences, workout history, and/or social circle (e.g., friends the user normally workouts out with). In another example, the user 120 can select the second user interface object 308, which causes the wrist-wearable device 110 to present the user 120 with another user interface (an alarm user interface, or a calendar user interface, etc.) or another user interface object (e.g., a calendar) that allows the user to schedule a time, location, and/or type of workout that the user plans to perform in the future.

In some embodiments, when determining an activity for the user 120 to perform in the physical world that is predicted to be suitable for the user based on the qualitative descriptor 112 of the user's physiological state, the wrist-wearable device 110 can also identify at least one other user with whom the user 120 should perform the physical activity. In some embodiments, the determination is based on other users who are in closest range to the user 120. In some embodiments, the user may add user profiles to his or her wrist-wearable device 110 (e.g., friends, family, colleagues), and the other users are selected from among those user profiles. In some embodiments, a recommendation is provided on the display 115 that the user 120 perform the physical activity with the at least one other user. For example, as shown in FIG. 3A, the third user interface object 310 recommends inviting "Amy" to workout with the user. In some embodiments, selection of the third user interface object 310 causes the wrist-wearable device 110 to send via one or more messaging applications associated with the wrist-wearable device 110 an invitation to the other user (e.g., Amy). This feature can allow for users to remain socially engaged and supported in their performance of the physical activities, for instance by walking with a group of neighbors or friends, playing basketball with colleagues that are all on a lunch break, etc. In some embodiments, the at least one other user is also determined to have the same qualitative physiological descriptor as the user 120, but in other embodiments the at least one other user is selected because that at least one other user has a qualitative physiological descriptor that is different from the user's, such that pairing the users together for performance of the physical activity helps to ensure that a user with a lower energy level is encouraged by a user with a higher energy level during the performance of the physical activity.

In FIG. 3B, a medium 116 qualitative descriptor 112 can include second status words 312 "Keep moving" and a second message 314 that states "Your fuel is mild-range. . . . Keep your activity moderate today," which are provided to the user 120 to help him or her maintain or improve his or her current physiological state. Further, the one or more user interface objects presented in the additional portion 301b can include activities determined to be appropriate for the user while the medium 116 qualitative descriptor 112 applies. More specifically, the one or more activities determined for the user 120 to perform in the physical world are adjusted such that the user 120's current physiological state improves and/or does not move to a lower energy/fuel level. In some embodiments, because the user 120's determined qualitative descriptor 112 is medium 116 (i.e., the user 120's current the physiological state is moderately healthy and/or moderately energetic), the wrist-wearable device 110 determines lower-intensity activities that the user can perform to take advantage of his or her current physiological state, such as going out for a walk. In FIG. 3B, the user 120 is presented with a fourth interface object 316 to start a walk, a fifth user interface object 318 to schedule performance of the activity at a future time, and/or a sixth user interface object 320 to check the user 120's current status.

As described above, selection of the user interface object from within the additional portion 301b of the user interface causes the wrist-wearable device 110 to perform an action associated with the selected user interface object. For example, the wrist-wearable device 110, in response to the selection of the fourth interface object 316, begins to monitor the user's performance of the walk. In some embodiments, the user 120 can specify (and/or be automatically recommended) other lesser-intensity activities such as light yoga, hiking, light resistance workouts, etc. The recommended workout can be based on the user's preferences, workout history, and/or social circle (e.g., friends the user normally workouts out with). Similarly, as mentioned above, the user 120 can schedule the activity for a future time by selecting the fifth user interface object 318 (similar to the second user interface object 308). In some embodiments, the user 120 can select the sixth user interface object 320, which causes the wrist-wearable device 110 to present the user 120 with another user interface including the user 120's current physiological state and/or one or more activity goals currently held or set by the user 120. Examples of the user interfaces including the user 120's current physiological state and/or one or more activity goals are described below in reference to FIGS. 5A-5C.

In FIG. 3C, a low 118 qualitative descriptor 112 can include third status words 322 "Take it easy" and a third message 324 that states "Your fuel looks low. . . . Look for ways to find breaks in your day," which are provided to the user 120 to help the user 120 reenergize himself or herself or improve his or her current physiological state. As described above in reference to FIGS. 3A and 3B, one or more user interface objects are presented in the additional portion 301b of the user interface. The one or more user interface objects include activities determined to be appropriate for the user while the low 118 qualitative descriptor 112 applies. More specifically, the one or more activities determined for the user 120 to perform in the physical world are adjusted such that the user 120's current physiological state improves. In some embodiments, because the user 120's determined qualitative descriptor 112 is low 118 (i.e., the user 120's current the physiological state is low energy, reflecting that the user might be tired or overstressed), the wrist-wearable device 110 determines mindful activities that the user 120 can perform to improve his or her current physiological state, such as meditation or breathing exercises. In FIG. 3C, the user 120 is presented with a seventh interface object 326 to do a meditation, an eighth user interface object 328 to schedule a bedtime, and/or a ninth user interface object 330 to pause streaks representing performance of physical activities by the user 120.

In some embodiments, the wrist-wearable device 110, in response to the selection of the seventh interface object 326, begins to monitor the user's performance of the meditation. In some embodiments, the wrist-wearable device 110 sets a timer for the duration of the mediation (e.g., five minutes, 10 minutes, 30 minutes). In some embodiments, the wrist-wearable device 110 enters a "do-not-disturb" mode in which calls are forwarded to voicemail and/or other notifications are silenced. In some embodiments, the user 120 can specify (and/or be automatically recommended) other relaxing and/or destressing activities such as taking a nap, reading, performing deep breathing exercises, stretching, etc. The recommended activity can be based on the user's preferences and/or history of activities known to relax. Similarly, as mentioned above, the user 120 can schedule the activity for a future time by selecting the eighth user interface object 328 (similar to the second user interface object 308). For example, the user can schedule a bedtime and the wrist-wearable device 110 will notify the user when the bedtime approaches.

In some embodiments, the user 120 can select the ninth user interface object 330, which causes the wrist-wearable device 110 to pause a streak for one or more workouts or activities of the user. For example, the user 120 could record working out for five consecutive days and, by selecting the pause streak user interface object, the user 120 can cause the wrist-wearable device 110 to temporarily pause the streak for a set amount of time (e.g., an hour, two hours) or end the streak. Any activity streaks (e.g., hourly streaks, daily streaks, weekly streaks, monthly streaks, yearly streaks) can be paused. Accordingly, when the user's energy level is determined to be low, the wrist-wearable device 110 can be configured to ensure that the user does not suffer further physiological setbacks by losing streaks that he or she has worked hard to retain. Instead, the system recognizes the low energy level of the user and finds ways to try to help the user move to higher energy levels (e.g., by performing lower-impact physical activities while also allowing users to pause their physical activity streaks at the same time, which in combination helps to ensure that users will take the actionable steps necessary to move toward a higher energy level).

Figure 3F:
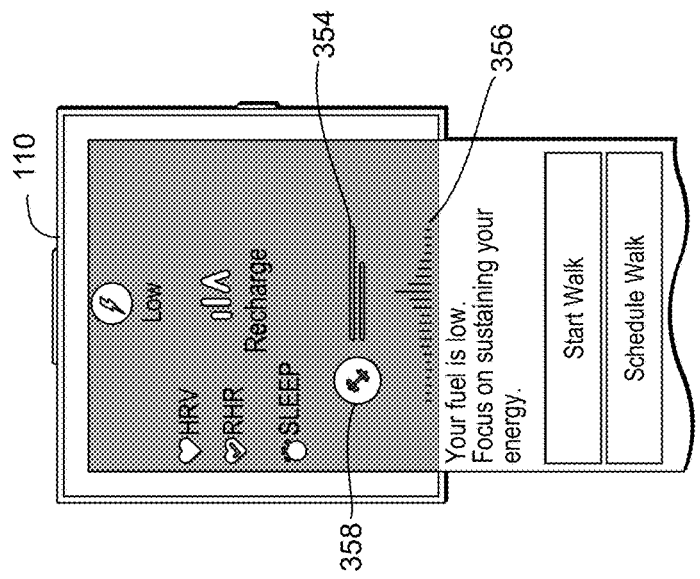
FIGS. 3D-3F illustrate a second embodiment of a user interface used to display determined qualitative descriptors and associated recommended activities for the user based on the determined qualitative descriptors, in accordance with some embodiments.
Figure 3E:
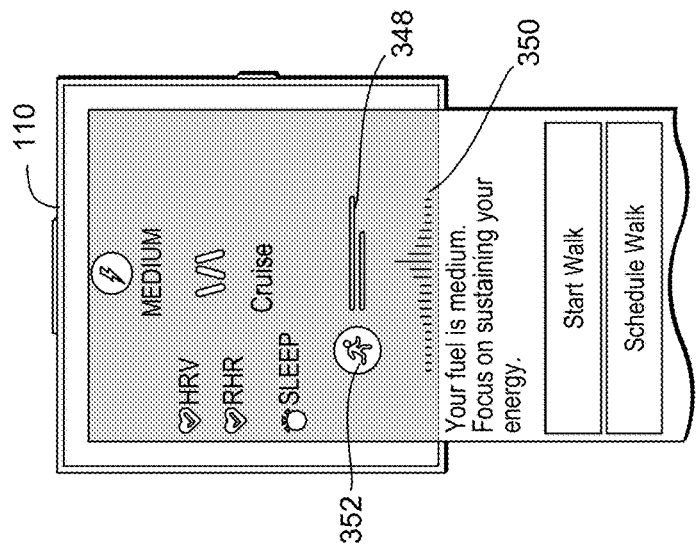
Figure 3D:
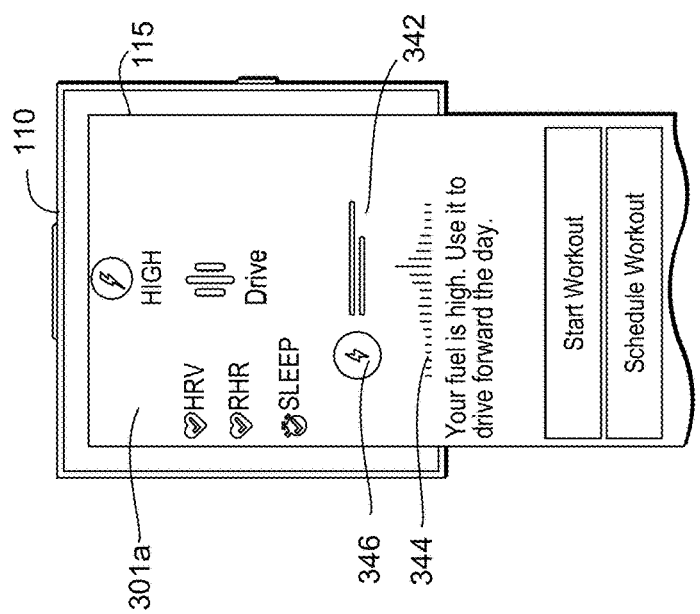

FIGS. 3D-3F illustrate a second embodiment of a user interface used to display determined qualitative descriptors and associated recommended activities for the user based on the determined qualitative descriptors. As shown in FIG. 3D, in some embodiments, the user interface includes a progress bar 342 and a graph plot 344. The displayed progress bar 342 and the graph plot 344 include a user 120's current status and the user 120's fuel levels. The progress bar 342 includes a goal indicator (top bar) and a current measured value (bottom bar) that allow the user to easily determine his or her daily status and progress to reaching his or her goals.

In some embodiments, the progress bar 342 can represent the user 120's burned calories (indicated by the electricity icon 346). Alternatively, as shown in FIGS. 3E and 3F, in some embodiments the progress bar can represent the user 120's steps (e.g., number of steps) or workouts (e.g., duration, intensity). In some embodiments, the respective activity portions are a representation of the user 120's sleep (duration, quality), water intake, calories, heart rate (HRV, RHR, etc.), and/or other physiological parameters. In this example, the user 120 is able to determine at which times he or she is the most active based on the monitored physiological state (e.g., heart rate, activity, sleep schedule, quality of sleep, burned calories, calories from their diet, etc.). In some embodiments, the progress bar 342 and the graph plot 344 measure the user 120's activity. For example, in some embodiments the progress bar 342 and the graph plot 344 correspond to a user's ability to reach his or her calorie goals (e.g., daily, weekly, monthly, etc.). In FIG. 3D, the user is able to determine how many calories he or she burned as well as his or her calorie intake throughout the day by looking at the graph plot 344. In some embodiments, the graph plot 344 includes an overlay (not shown) representative of historic or baseline values for the physiological parameters.

Turning to 3E, in some embodiments the progress bar 348 and the graph plot 350 are representations of the user 120's steps (represented by a moving person icon 352). In some embodiments, the progress bar 348 and the graph plot 350 include information relating to the user 120's step goals. For example, the progress bar 348 and the graph plot 350 can illustrate how close the user is to accomplishing a certain task or activity (e.g., reaching a goal step count). For example, the user may input a goal of 10,000 steps a day. In this example, the progress bar 348 can show how many steps the user has accomplished in relation to the goal (e.g., percentage of steps to goal, number of steps to goal, bar chart). In some embodiments, the progress bar 348 provides the amount that the user 120 has left to accomplish (time, steps, etc.).

In some embodiments, as shown in FIG. 3F, the progress bar 354 and the graph plot 356 are representations of the user 120's workout (represented by a dumbbell weight icon 358). In some embodiments, the progress bar 354 and the graph plot 356 include information relating to the user 120's workout goals. For example, the progress bar 354 and the graph plot 356 can illustrate how close the user is to accomplishing a certain task or activity (e.g., reaching a goal, a workout intensity level, total workout time for the day, burned calories). For example, the user may input a goal of 60-minute workouts a day and the progress bar 354 and the graph plot 356 can update as the user performs activities throughout the day.

Figure 3I:
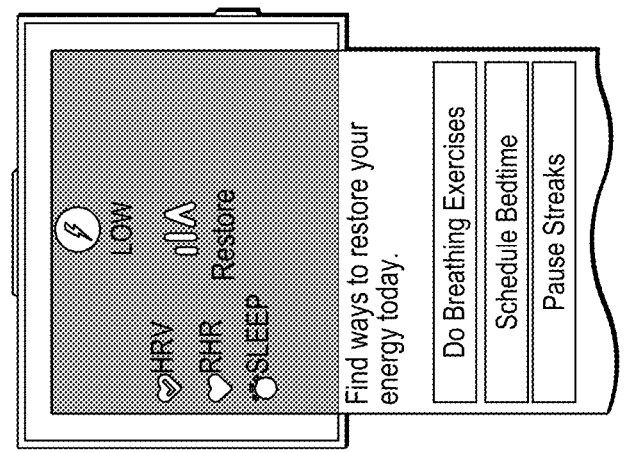
FIGS. 3G-3I illustrate a third embodiment of a user interface used to display determined qualitative descriptors and associated recommended activities for the user based on the determined qualitative descriptors, in accordance with some embodiments.
Figure 3H:
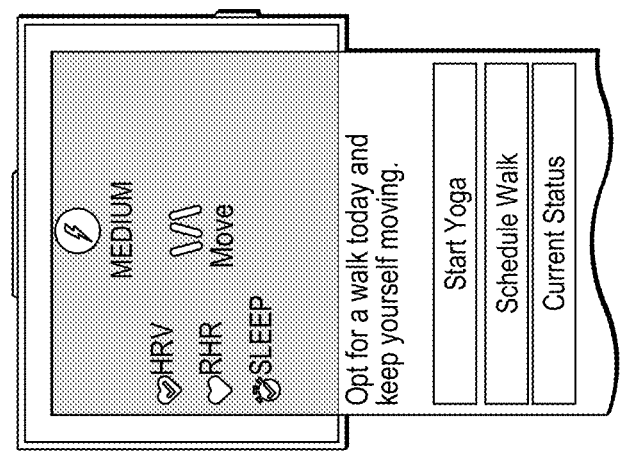
Figure 3G:
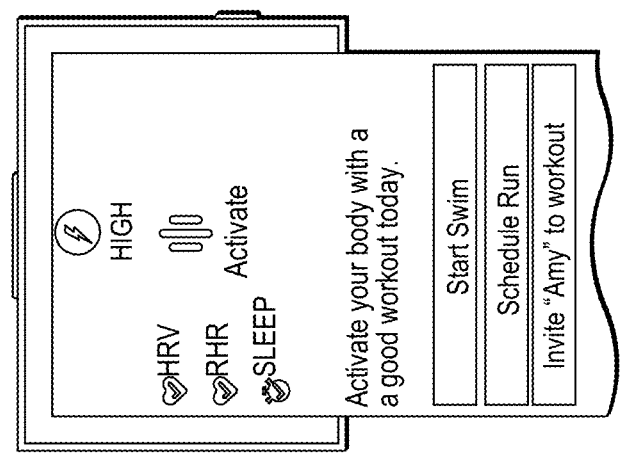

FIGS. 3G-3I illustrate a third embodiment of a user interface used to display determined qualitative descriptors and associated recommended activities for the user based on a current qualitative descriptor of the user's physiological state. FIGS. 3G-3I illustrate respective qualitative descriptors "High," "Medium," and "Low," similar to those described above in reference to FIGS. 1A-3C. FIGS. 3G-3I further illustrate different embodiments of status words, such as "activate," "move," and "restore," and different embodiments of messages (e.g., "Activate your body with a good workout today") displayed to a user. In some embodiments, status words and messages are updated periodically to encourage, motivate, and/or coach throughout the day as their physiological state and, particularly, energy level for undertaking tasks and activities at a particular time, changes. For example, after an intense workout, the user can be presented with a status indicating that he or she should "Recharge," "Rest" and/or "Recover." In some embodiments, the user is presented with a rest and/recovery period (e.g., rest for 10 hours, one day, two days) and, when the recovery period has lapsed, the user is presented with a "Ready" indicator or other similar indication. In some embodiments, as is the case with the qualitative descriptor, the status indicator is based on a comparison of the plurality of physiological parameters to baseline values for the physiological parameters as described above in reference to FIGS. 1A-1F.

FIGS. 3J-3L illustrate a fourth embodiment of a user interface used to display determined qualitative descriptors and associated recommended activities for the user based on the determined qualitative descriptors. FIGS. 3J-3L include similar features to those described above in FIGS. 1A-3I and also illustrate other examples of status words, such as "Drive," "Cruise," and "Recharge," and different embodiments of messages (e.g., "Activate your body with a good workout today") displayed to a user. Similarly, FIGS. 3J-3L show other example user interface objects including activities recommended to the user based on the current qualitative descriptor that is determined to represent the user's physiological state.

FIG. 3J further shows an example user interface for displaying specific ranges of values 360 for the physiological parameters. The specific ranges include low and high baseline values of the physiological parameters, as well as the user 120's current measured values. The specific ranges are represented as bar graphs, which allow a user 120 to easily identify and compare his or her current measured values with high and low baseline values of the physiological parameters. As shown in FIG. 3L, when a user 120's current measured values reach or drop below a low baseline value or, in some cases, exceed a high baseline value, an associated icon is unchecked (e.g., in FIG. 3L, HRV, and SLEEP are unchecked icons because the current HRV values exceed the high baseline value, and the sleep values meet the low baseline values). FIG. 3K shows another example user interface for displaying specific ranges of values 365 for the physiological parameters. The specific ranges include low and high baseline values of the physiological parameters represented on a sliding scale. As the user 120's measured values change throughout the day, a marker on the sliding scale moves accordingly. For example, as shown in FIG. 3K, the user 120's HRV is measured near low baseline values (which result in the HRV icon to be unchecked). In some embodiments, the user interfaces shown in FIGS. 3J-3L are presented to the user in response to detection of user input at one of the user icons representing HRV, RHR, and Sleep, or selection of a "Current Status" user interface object 320 (FIG. 3B).

Figure 3O:
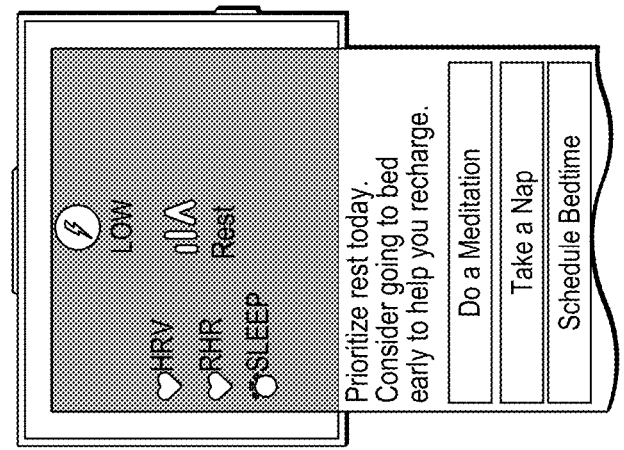
FIGS. 3M-3O illustrate a fifth embodiment of a user interface used to display determined qualitative descriptors and associated recommended activities for the user based on the determined qualitative descriptors, in accordance with some embodiments.
Figure 3N:
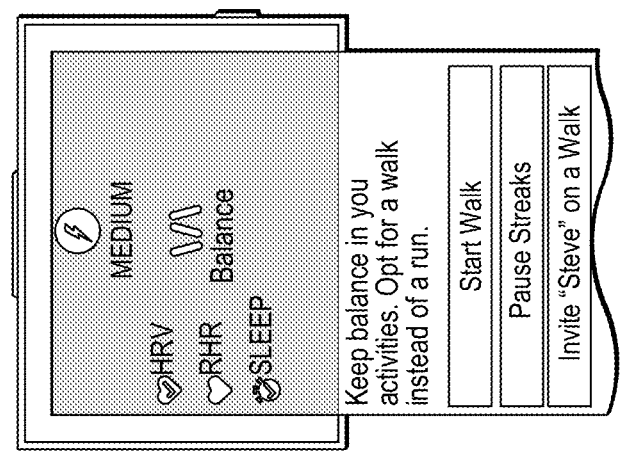
Figure 3M:
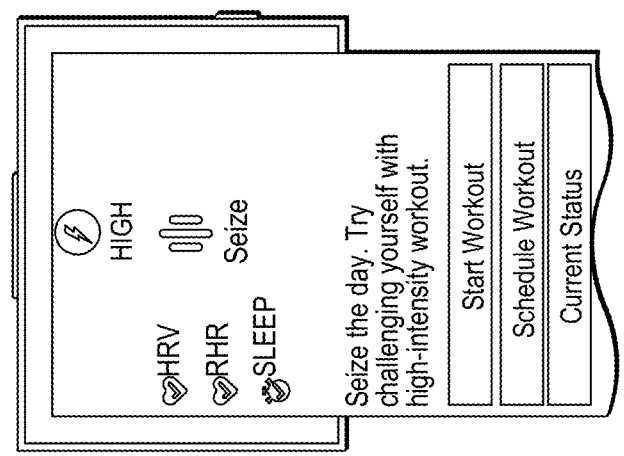

FIGS. 3M-3O illustrate a fifth embodiment of a user interface used to display determined qualitative descriptors and associated recommended activities for the user based on the determined qualitative descriptors. FIGS. 3M-3O include similar features to those described above in FIGS. 1A-3L and also show other examples of status words, such as "Seize," "Balance," and "Rest," and different embodiments of messages (e.g., "Prioritize rest today. Consider going to bed early to help you recharge.") displayed to a user. Similarly, FIGS. 3M-3O show other examples of user interface objects, including activities recommended to the user based on the current qualitative descriptor that is determined to represent the user's physiological state.

The skilled artisan will appreciate that different combinations of the qualitative descriptors, status words, message, user interface objects, and/or other features described with reference to FIGS. 3A-3O can be used in various combinations. For example, the user interface in FIG. 3N can include any user interface object in FIGS. 3B, 3E, 3H, and 3K (i.e., user interfaces associated with a medium qualitative descriptor). In some embodiment, user interface objects for different qualitative descriptors can be combined. For example, the "Drink Water" user interface object shown in FIG. 3K (a user interface associated with a medium qualitative descriptor) can be included in a user interface object associated with a high or low qualitative descriptor. The different combinations of qualitative descriptors, status words, message, user interface objects, etc., can be based on the comparisons of the measured values for the user's physiological parameters with the associated baseline values. The embodiments shown in FIGS. 3A-3O are also non-exhaustive. Different messages and/or status words not specifically shown in the provided embodiments can also be presented to the user. Additionally, FIGS. 3A-3O also show different user interface objects associated with activities determined for the user to perform in the physical world. In some embodiments, different qualitative descriptors can include the same user interface objects associated with activities determined for the user to perform in the physical world. The skilled artisan will appreciate that the different messages, status words, and/or user interface objects associated with activities determined for the user to perform in the physical world can be provided to the user 120 based on the determined qualitative descriptors.

Figure 4A:
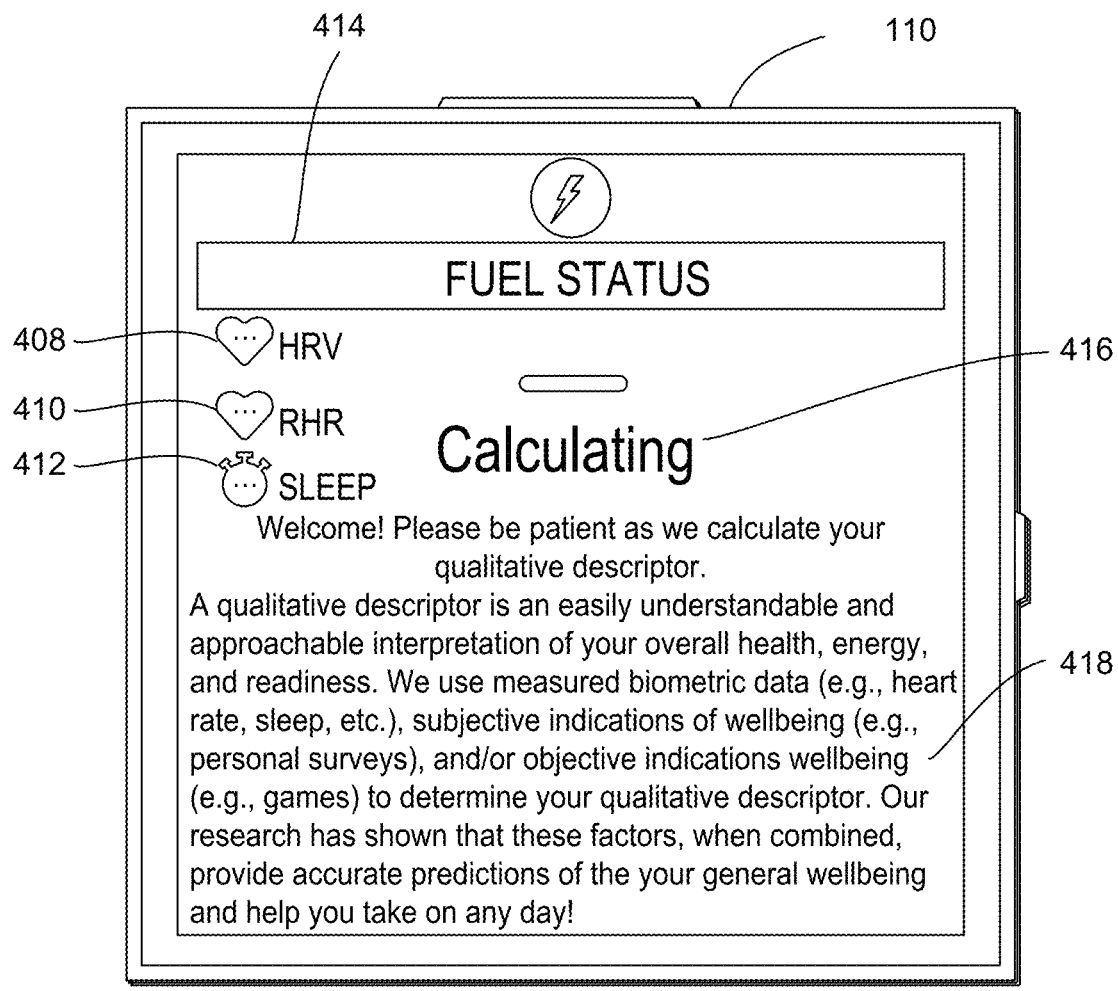
FIGS. 4A-4B illustrate user interfaces that can be presented to the user to provide explanations as to how qualitative descriptions are determined, in accordance with some embodiments.
Figure 4B:
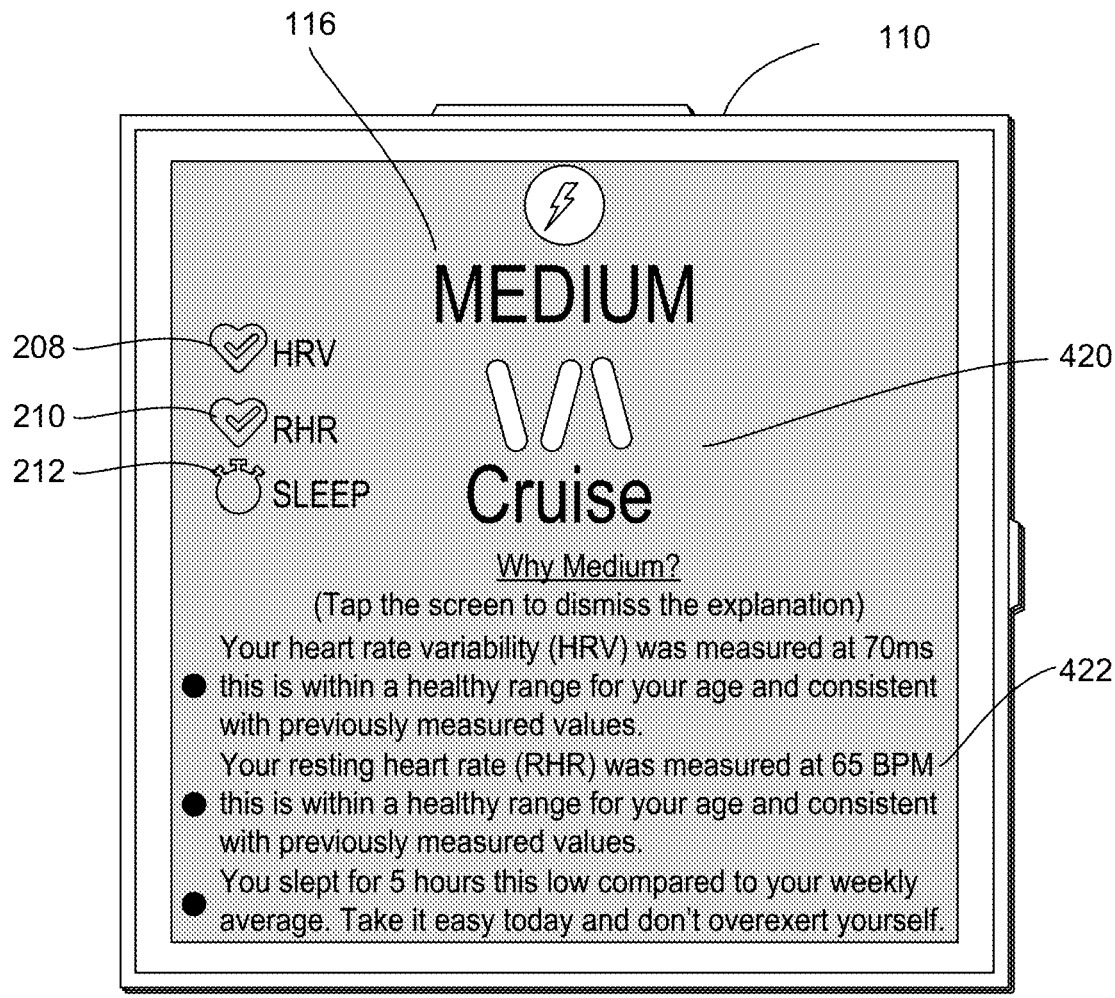

FIGS. 4A-4B illustrate user interfaces that can be presented to the user to provide explanations as to how qualitative descriptions are determined, in accordance with some embodiments. In FIG. 4A, a wrist-wearable device 110 displays a user interface including a fuel status 414, representations of at least three different physiological parameters (e.g., icons representing HRV 408, RHR 410, and Sleep 412), a pending status 416, and a brief description 418. The icons representing HRV 408, RHR 410, and Sleep 412 are similar to HRV 208, RHR 210, and Sleep 212; however, they include ellipses to indicate that they are currently being measured and/or being updated. In some embodiments, before a qualitative descriptor is determined for the user, the wrist-wearable device 110 displays to the user at least the fuel status 414 and the pending status 416. The fuel status 414 user interface object is a temporary place holder for a predefined qualitative descriptor (e.g., "High" 114, "Medium" 116, and "Low" 118 described above in reference to FIGS. 1A-1F) when determined. In some embodiments, the pending status 416 notifies the user that his or her qualitative descriptor is being determined (e.g., calculating).

In some embodiments, before the qualitative descriptor is determined for the user, the wrist-wearable device 110 displays a brief description 418 explaining to the user how the qualitative descriptors of the user's physiological state will be determined by the wrist-wearable device 110 and an explanation of research behind the use of qualitative descriptors of the user's physiological state. For example, the brief description 418 can explain to the user that physiological parameters, subjective indications of well-being, and objective indications of well-being are used to determine the user's qualitative descriptor (additional information on the determination of the qualitative descriptors is provided above in references to FIGS. 1A-1F). In some embodiments, before the wrist-wearable device 110 determines the qualitative descriptor, the user interface includes a description about values for physiological parameters that will be collected in conjunction with determinations of qualitative descriptive of the user's physiological state (and, in some embodiments, the user has the ability to opt out of the tracking of any of these physiological parameters). For example, as shown in the brief description 418, a user will be notified that his or her heart rate, sleep, and other data will be used for determining the qualitative descriptor.

Turning to FIG. 4B, the wrist-wearable device 110 displays a user interface including a medium 116 qualitative descriptor, representations of at least three different physiological parameters (e.g., icons representing HRV 208, RHR 210, and Sleep 212), a current status word 420 (similar to status words 302, 312, and 322 described above in reference to FIGS. 3A-3O), and a determination explanation 422. In some embodiments, the wrist-wearable device 110 displays in the user interface (along with the determined qualitative descriptor) information to the user regarding the values for the plurality of physiological parameters so that the user is informed as to how the qualitative descriptor was determined. For example, as shown in the determination explanation 422, the user is provided with an explanation as to why he or she was provided a medium 116 qualitative descriptor. In some embodiments, the determination explanation 422 includes measured values (e.g., measured HRV, RHR, and sleep values) and a brief explanation as to how the measured values relate to the user's age and/or baseline values (e.g., previously measured values, weekly average, and/or other example baselines provided above in reference to FIGS. 1A-1F).

In some embodiments, each representation of the at least three different physiological parameters provides the user 120 with a readily understandable status of current values for each of these physiological parameters. In particular, each representation of the at least three different physiological parameters provides the user with an indication of whether the user's value for that physiological parameter is within an expected range. In some embodiments, the indication of whether the user's value for that physiological parameter is within an expected range includes filled-in or empty icons, bolded or non-bolded icons, highlighted or unhighlighted icons, checked or unchecked icons, a sliding scale of values, etc. For example, as shown in FIG. 4B, two of the at least three different physiological parameters are checked off and one of the at least three different physiological parameters is unchecked, which notifies the user that one physiological parameters is not within an expected range (in this example, sleep 212 was not within an expected range).

In some embodiments, the at least three different physiological parameters can be used to provide a user 120 with a quick understanding of how his or her determined qualitative descriptor was selected. For example, a high 114 predefined qualitative descriptor 112 can be associated with the at least three different physiological parameters being checked off (i.e., within expected ranges relative to the associated baseline values), a medium 116 predefined qualitative descriptor 112 can be associated with two of the at least three different physiological parameters being checked off (i.e., within expected ranges relative to the associated baseline values), and a low 118 predefined qualitative descriptor 112 can be associated with one (or none) of the at least three different physiological parameters being checked off (i.e., within expected ranges relative to the associated baseline values). Examples of this can be seen in FIGS. 1A-3O.

Figures 5A, 5B, 5C:
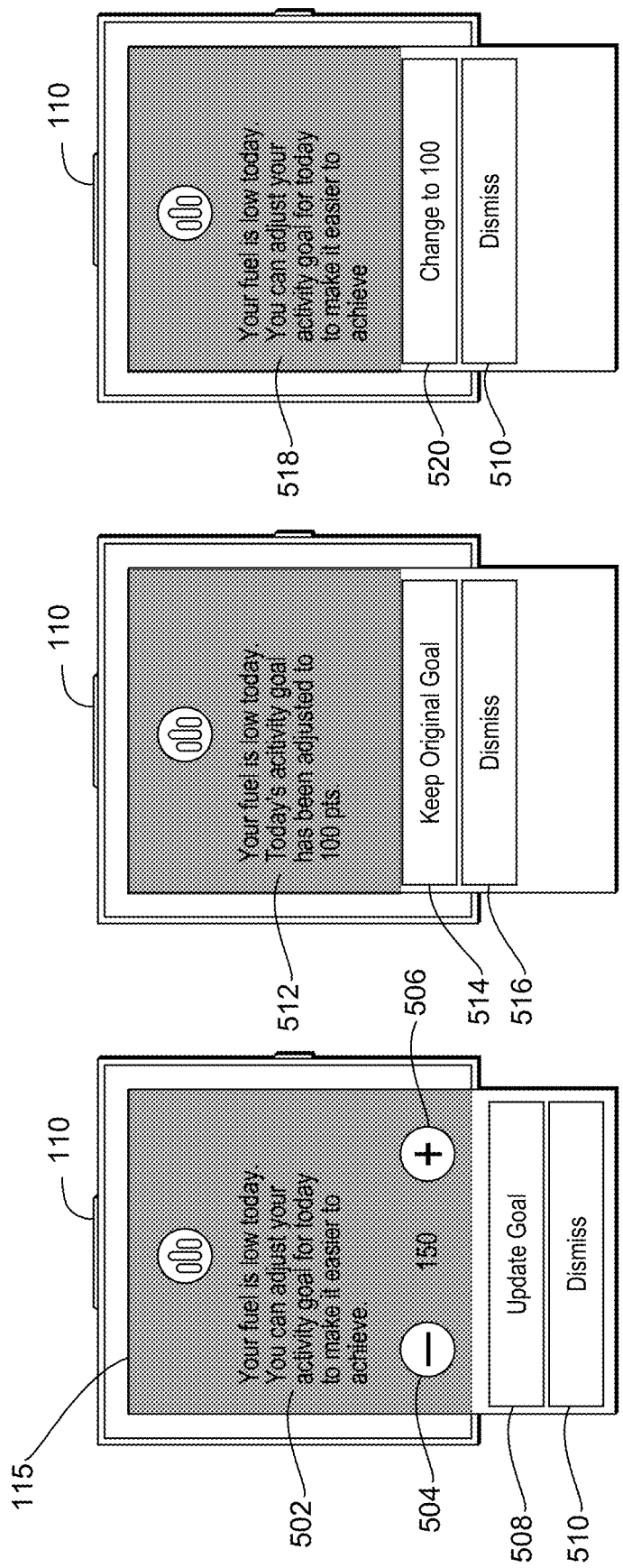
FIGS. 5A-5C illustrate example user interfaces presented on the wrist-wearable devices that allow the user to adjust one or more goals and/or activities, in accordance with some embodiments.

FIGS. 5A-5C illustrate examples of user interfaces presented on the wrist-wearable devices 110 that allow the user to adjust one or more goals and/or activities, in accordance with some embodiments. In some embodiments, a user interface can be presented to the user 120 that allows the user 120 to modify or adjust a goal or activity. In some embodiments, and in accordance with a determination that the qualitative descriptor for the user 120's physiological state corresponds to a low energy state, the wrist-wearable device 110 displays automatically and without human intervention (e.g., no request for the user), via its display 115, a user interface that allows the user to adjust a physical activity goal by a certain amount.

For example, FIG. 5A shows that the display 115 includes a message 502 corresponding to the user 120's qualitative descriptor (low energy level) and also includes a suggestion that has been determined based on the qualitative descriptor. In FIG. 5A, the message states "Your fuel is low today. You can adjust your activity goal for today to make it easier to achieve." In some embodiments, the user interface for adjusting the one or more goals includes one or more user interface objects for decreasing (e.g., "−" 504) or increasing (e.g., "+" 506) the goal, respectively. In this example, the user updates his or her physical activity goal such that the user defines the certain amount by which the physical activity goal would be adjusted. The goal can be a time duration, a point score based on the activity performed, the number of activities performed, calories burned, target heart rate, and/or any other measure of performance. In some embodiments, the wrist-wearable device 110, automatically and without human intervention, suggests a new goal to be accepted or declined by the user. For example, a drop-down can provide options to the user. The user can select one or more of the options presented. A confirmation user interface object 508 (as shown in FIG. 5A) allows the user to confirm and update the goal to the user-defined goal. In some embodiments, a cancellation user interface object 510 allows the user to dismiss the recommended change. In some embodiments, adjusting the activity goal is done by the user or is automatically, without human intervention, determined by the wrist-wearable device 110. In some embodiments, the user 120 is prompted for a confirmation before the goal is automatically adjusted.

Turning to FIG. 5B, in some embodiments the wrist-wearable device 110 presents to the user 120 a recommended amount by which to adjust his or her physical activity goal (e.g., 100 pts) such that the certain amount by which the physical activity goal is adjusted is automatically determined by the wrist-wearable device 110, without requiring human intervention to determine the certain amount by which the physical activity goal is to be adjusted. For example, the goal can be automatically changed from 150 points to 100 points. In some embodiments, the wrist-wearable device 110 presents another message 512 to the user 120 reflecting the change. For example, the other message 512 can state "Your fuel is low today. Today's activity goal has been adjusted to 100 points." In some embodiments, the wrist-wearable device 110 displays user interface objects that allow the user to reject the automatic change (e.g., "Keep Original Goal" 514) or to acknowledge and dismiss the message (e.g., "Dismiss" 516). In some embodiments, the user interface objects are included in a drop-down menu.

FIG. 5C is an example of an adjustment to a goal using a user interface object presented on the display of the wrist-wearable device 110. For example, the wrist-wearable device 110 can present to the user an additional message 518 stating, "Your fuel is low today. You can adjust your activity goal for today to make it easier to achieve." The additional message 518 can be presented with a user interface object including a recommended change determined to be appropriate (e.g., based on past instances in which the user has missed reaching activity targets by particular amounts while the user had a low fuel level) by the wrist-wearable device 110 (e.g., "Change to 100" 520). In some embodiments, the cancellation user interface object 510 allows the user to dismiss the recommended change.

The messages and recommended adjustments discussed above are presented to the user in order to encourage the user to remain active despite his or her low energy (fuel) level while also providing the user 120 with opportunities to reach a higher energy level. In some embodiments, the user interface for adjusting a user's one or more goals is presented to the user in response to selection of a "pause streaks" user interface object, examples of which are described above in reference to FIGS. 3A-3O.

In some embodiments, the goals are an amount of time that the user is engaging in an activity (e.g., walking, running, meditating, reading, lifting weights). In some embodiments, the goals correspond to physical health conditions (e.g., low stress levels, high energy, motivated mindset, low blood pressure, steady heart rate and breathing). In some embodiments, the goals are points corresponding to the user's participation in certain activities (e.g., predetermined amount of points for sleep time, quality, exercise time, streak length). In some embodiments, a metric is used to represent the goals (e.g., metabolic equivalent of task (MET)—minutes, activity points, intensity points, METs, Hearts, Points). In some embodiments, the wrist-wearable device can use several metrics corresponding to various activities. In some embodiments, a description of each metric is presented to the user in a pop-up or scroll-down portion of a displayed user interface. The discussion below of FIGS. 6A-6E identifies examples of the metrics used to track different user goals.

FIGS. 6A-6E illustrates different activity metrics monitored by the wrist-wearable device, in accordance with various embodiments. Specifically, FIGS. 6A-6E present user interfaces at the wrist-wearable device 110 for performing activities and tracking progress. For example, the wrist-wearable device 110 can display a user-interface element 608 that, when selected by the user, causes display of the user's current progress for that task. In some embodiments, the user interface element 608 is a period of time. In this example, the user interface element is a time period being monitored (e.g., a week). In some embodiments, the user-interface element is a month, year, etc. In some embodiments, a second user interface element 606 is provided that allows the user to adjust the time period being monitored. For example, selection of user-interface element 606 causes the activity for the day to be presented to the user. The above examples are non-limiting and different time periods can be used. In some embodiments, the user can define the length of time to be monitored. In some embodiments, the user interfaces shown in FIGS. 6A-6E are shown in response to detection of a user input to start an activity (e.g., "start workout" user interface object 306).

In some embodiments, the display shows an illustration 604 of the user's progress. In some embodiments, the illustration 604 is a chart, graph, image, percentage, amount, etc. In this example, the illustration 604 is a track, and the track is filled in based on the user's progress. In some embodiments, the illustration 604 has a corresponding metric 602. In FIG. 6A, the metric 602 is METs. Other examples of metrics are shown in FIGS. 6B-6E (e.g., metric 628 in FIG. 6B corresponding to intensity points, metric 630 in FIG. 6C corresponding to points, metric 632 in FIG. 6D corresponding to activity points, metric 634 in FIG. 6E corresponding to hearts). In some embodiments, the metric (e.g., 602, 628, 630, 632, 634) has a corresponding text related to the metric. For example, the metric 602 includes a numerical characterization of the amount of activity the user has accomplished compared to his or her goal (e.g., 262/1050 METs, 30/100 minute cardio, 20,000/70,000 steps).

In some embodiments, the display has drop-down menu 636 that includes a breakdown menu 612 with information relating to the activities. Alternatively, in some embodiments breakdown menu 612 is part of the user interface element and the user can scroll down to different portions of the user interface. In some embodiments, the breakdown menu 612 includes a series of user interface elements corresponding to the amount of energy excreted by the user or the activity level at which the user performed. Each activity level can have a corresponding metric value (e.g., 620, 622, 624, 626, 628) and a duration of time at which the user performed at that activity level. For example, FIG. 6A shows a breakdown of light-, moderate-, and high-intensity activities performed by the user 120. For example, user interface element 614 shows a light-intensity activity (e.g., a walk) performed by the user that lasted for 13 minutes. The user interface element 614 includes a metric associated with it (e.g., metric 620 for METs, e.g., 50 METs). User interface element 616 shows a moderate-intensity activity (e.g., a jog, a moderate bike ride) performed by the user that lasted for 33 minutes, and user interface element 618 shows a high-intensity activity (e.g., a sprint, high intensity interval training (HIIT)) performed by the user that lasted for three minutes.

In some embodiments, time element 610 can reflect the local time at the user's current location. In some embodiments, the time element 610 provides a representation of a stopwatch and/or a timer being used by the user.

Figure 7:
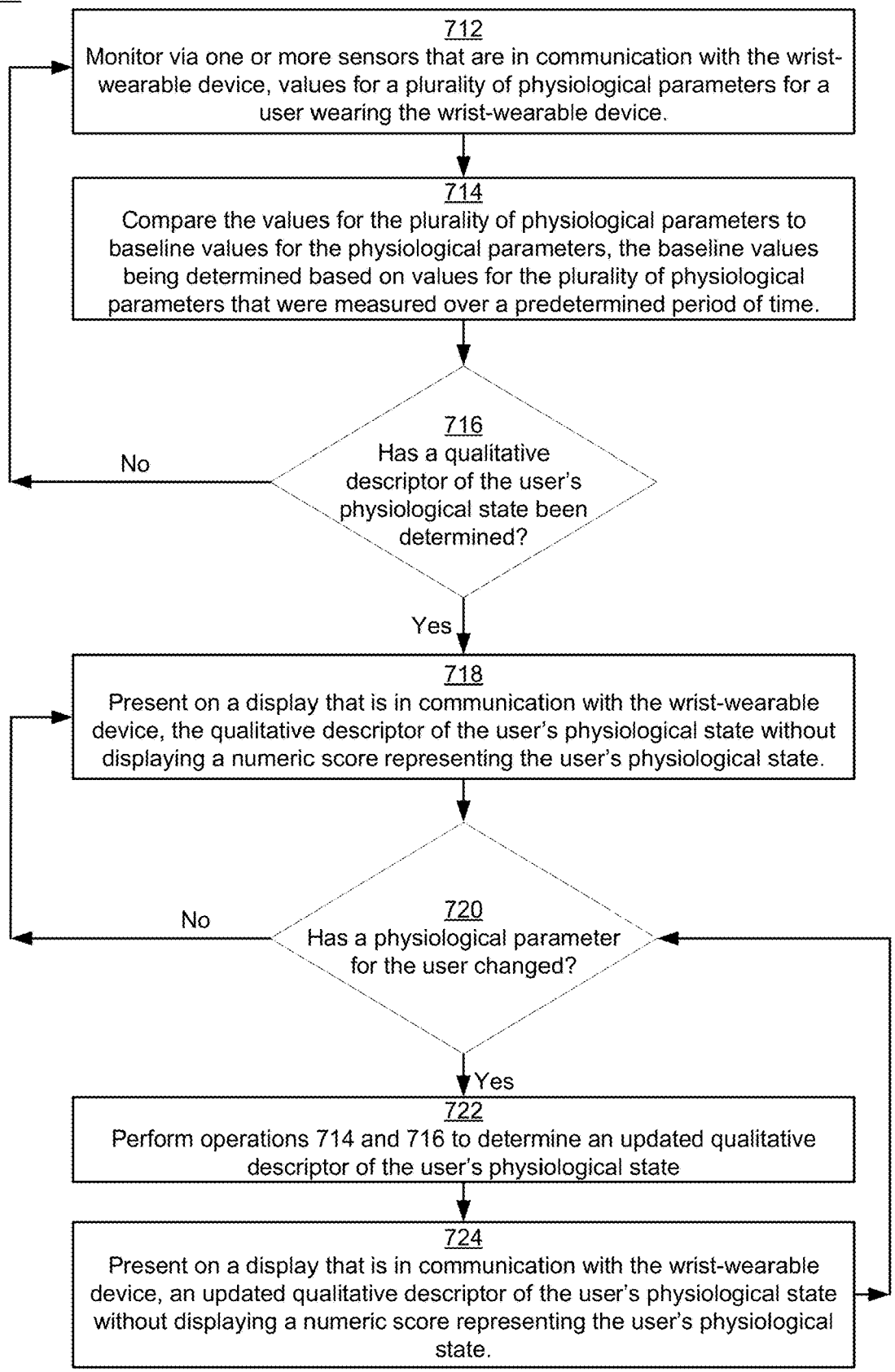
FIG. 7 is an overview flow diagram illustrating a method of determining a qualitative descriptor at a wrist-wearable device, in accordance with various embodiments.
Figure 10:
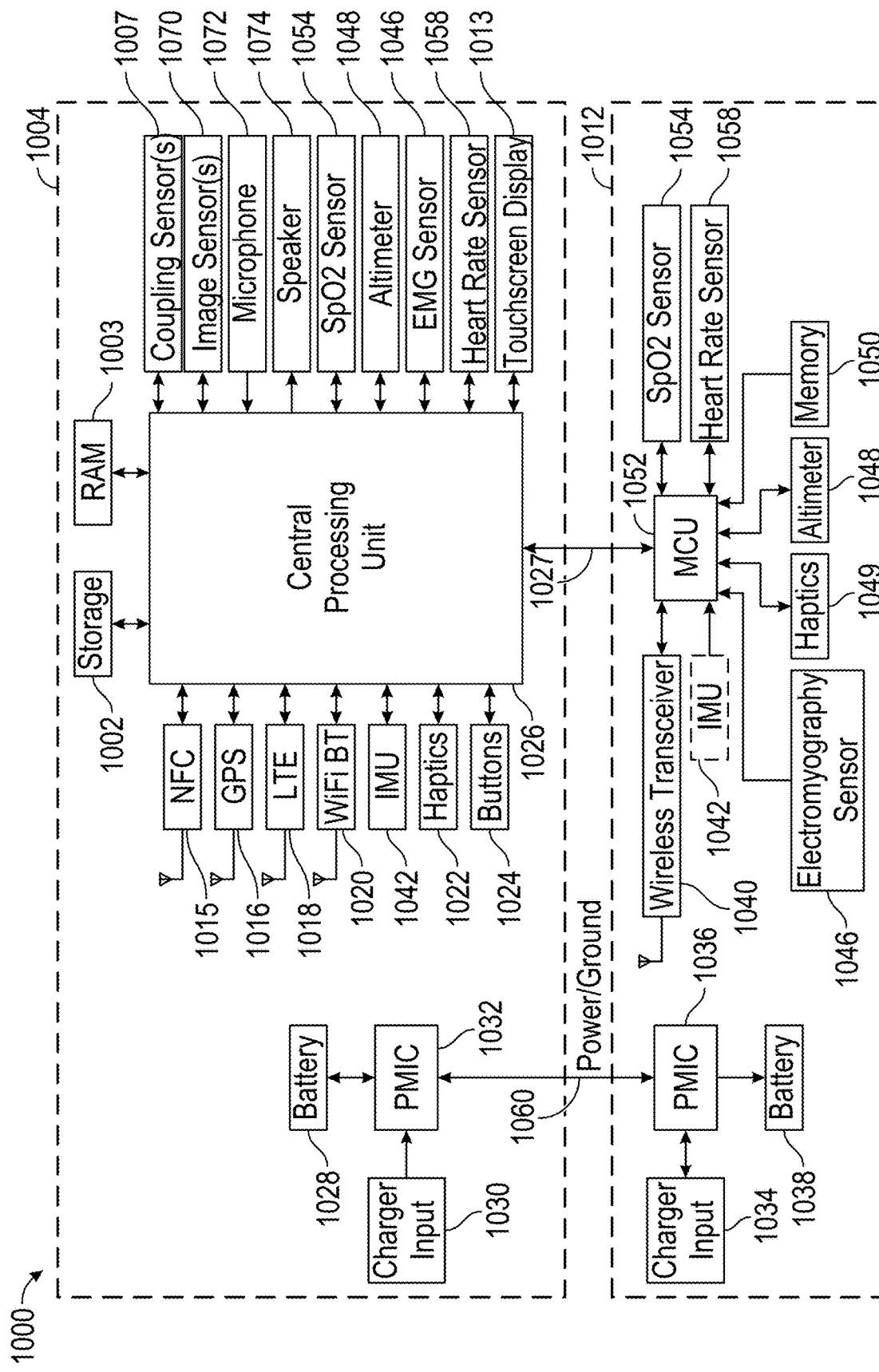
FIG. 10 is a block diagram of a wrist-wearable device system, according to at least one embodiment of the present disclosure.

FIG. 7 is an overview flow diagram illustrating a method of determining a qualitative descriptor at a wrist-wearable device, in accordance with some embodiments. Operations (e.g., steps) of the method 700 may be performed by one or more processors 1026 and/or 1052 (FIG. 10) of a wrist-wearable device 110. At least some of the operations shown in FIG. 7 correspond to instructions stored in a computer memory or computer-readable storage medium (e.g., storage 1002 of the wrist-wearable device 110; FIG. 10). Operations 712-718 can also be performed in part by using one or more processors and/or using instructions stored in memory or computer-readable medium of a computing device (such as a head-mounted display device that can perform operations 712-718 alone or in conjunction with the one or more processors of the wrist-wearable device 110).

In some embodiments, the method 700 includes monitoring (712) via one or more sensors that are in communication with the wrist-wearable device 110 values for a plurality of physiological parameters for a user wearing the wrist-wearable device 110. The method 700 includes comparing (714) the values for the plurality of physiological parameters measured via the one or more sensors to baseline values for the physiological parameters. The baseline values are determined based on values for the plurality of physiological parameters that were measured over a predetermined period of time as described above in FIGS. 1A-1F.

Based on the comparison, the method 700 includes determining (716) a qualitative descriptor corresponding to the user's current physiological state. In accordance with no qualitative descriptor being determined (determination "No" at operation 716), the method 700 includes returning to operation (712) and continues to monitor values for the plurality of physiological parameters via the one or more sensors. Alternatively, in accordance with a determination of a qualitative descriptor (determination "Yes" at operation 716), the method 700 includes presenting (718), via a display that is in communication with the wrist-wearable device 110, the determined qualitative descriptor of the user's current physiological state. The qualitative descriptor is presented without a numeric score representing the user's physiological state.

In some embodiments, the method 700, after presenting the determined qualitative descriptor of the user's current physiological state, continues to monitor the user's physiological parameters and determines (720) whether a physiological parameter for the user has changed. In accordance with a determination that no physiological parameter for the user has changed (determination "No" at operation 720), the method 700 includes returning to operation (718) and continues presenting, on the display, the determined qualitative descriptor of the user's current physiological state. Alternatively, in accordance with a determination that a physiological parameter for the user has changed (determination "Yes" at operation 720), the method 700 includes performing (722) operations (714) and (716) to determine an updated qualitative descriptor of the user's physiological state. The method 700 further includes presenting (724) on the display that is in communication with the wrist-wearable device the updated qualitative descriptor of the user's physiological state without displaying a numeric score representing the user's physiological state. In some embodiments, the method 700 returning to operation (770) to continue to monitor any changes to the plurality of physiological parameters via the one or more sensors.

FIGS. 8A-8E are detailed flow diagrams illustrating a method 800 of determining a qualitative descriptor, in accordance with some embodiments. Operations (e.g., steps) of the method 800 may be performed by one or more processors 1026 and/or 1052 (FIG. 10) of a wrist-wearable device 110 (FIG. 1). At least some of the operations shown in FIGS. 8A-8E correspond to instructions stored in a computer memory or computer-readable storage medium (e.g., storage 1002 of the wrist-wearable device 110; FIG. 10). Operations 810-856 can also be performed in part by using one or more processors and/or using instructions stored in memory or computer-readable medium of a computing device (such as a head-mounted display device that can perform operations 810-856 alone or in conjunction with the one or more processors of the wrist-wearable device 110).

Method 800 includes monitoring (810), via one or more sensors that are in communication with the wrist-wearable device, values for a plurality of physiological parameters for a user wearing the wrist-wearable device 110. In some embodiments, each sensor of the one or more sensors is (812) physically coupled (e.g., either via a capsule portion or a band portion of the wrist-wearable device 110) with the wrist-wearable device 110. In other embodiments, some of the one or more sensors can be in communication with the wrist-wearable device 110 but not physically coupled with it. In some embodiments, the wrist-wearable device 110 includes (814) a display that is in communication with the wrist-wearable device 110. In some embodiments, the display is also physically coupled with the wrist-wearable device 110. In other embodiments, the display can be a display at a device that is communicatively coupled with the wrist-wearable device 110, such as a user's smartphone, laptop, table, artificial-reality glasses, virtual-reality head-mounted display, etc. In some embodiments, the plurality of physiological parameters monitored by the one or more sensors includes (816) three or more of heart rate, heart rate variability, duration of deep sleep, blood oxygen levels, blood pressure, stress level, energy level, and activity level.

The method 800 further includes comparing (818) the values for the plurality of physiological parameters to baseline values for the physiological parameters. As described above in reference to FIGS. 1A-AF, the baseline values are determined based on values for the plurality of physiological parameters that were measured over a predetermined period of time (e.g., 30 days). In some embodiments, the values for the plurality of physiological parameters can be values that were measured over the predetermined period of time while the user was in a state of deep sleep. In some embodiments, the baseline values are (819) determined based on values for the plurality of physiological parameters that were measured over a predetermined period of time while the user was in a state of deep sleep (e.g., the stage of sleep that a user typically would need to feel refreshed when he or she wakes up, such as rapid eye movement (REM) sleep). In some embodiments, the comparison (820) is conducted using a machine-learning model that was trained using the baseline values for the physiological parameters. In some embodiments, the machine-learning model was (822) also trained using (i) subjective indications of the user's physiological state and (ii) objective indications of a cognitive or motor function of the user. The cognitive or motor function of the user has a first known variance with respect to one or more physiological parameters of the plurality of physiological parameters. In some embodiments, the subjective indications have a second known variance with respect to one or more physiological parameters of the plurality of physiological parameters. The subjective and objective indicators are described below in reference to FIGS. 11A-11C.

The method 800 includes based on the comparing, determining 824 a qualitative descriptor of the user's physiological state from among a set of three or more predefined qualitative descriptors. In some embodiments, there are three predefined qualitative descriptors; in other embodiments, there are no more than six predefined qualitative descriptors. A fewer number of predefined qualitative descriptors helps to ensure that the descriptors remain actionable for users.

The method 800 includes presenting (826) on a display that is in communication with the wrist-wearable device, the qualitative descriptor of the user's physiological state without displaying a numeric score representing the user's physiological state. In some embodiments, the method 800 includes, in accordance with a determination that the qualitative descriptor for the user's physiological state corresponds to a low energy state, display on the display (828) a user interface object that allows the user to adjust a physical activity goal by a certain amount. In some embodiments, the certain amount is (830) provided by the user or is automatically, without human intervention, determined by the wrist-wearable device 110.

Examples of the user interface are shown in FIGS. 5A-5C. In FIG. 5A, the user is allowed to update their physical activity goal, such that the user defines the certain amount by which the physical activity goal would be adjusted. In FIG. 5B, the user is provided with a recommended amount by which to adjust his or her physical activity goal, such that the certain amount by which the physical activity goal is adjusted automatically determined by the wrist-wearable device, without requiring human intervention, to determine the certain amount by which the physical activity goal is adjusted.

In some embodiments, the method includes determining (832) an activity for the user 120 to perform in the physical world that is predicted to be suitable for the user 120 based on the qualitative descriptor of the user 120's physiological state. In some embodiments, suitable activities are activities that are predicted to be appropriate for the user 120 while the (current) qualitative descriptor of the user's physiological state continues to apply. For example, if the qualitative descriptor of the user's physiological state is within one of the categories indicating that the user has a lower fuel level (e.g., low 118 qualitative descriptor 112; FIG. 1), then the determined activity can be predicted to be suitable for the user because it will help to further improve the user's energy level, which should help to move the user to a higher fuel level (e.g., high 114 or medium 116 qualitative descriptor 112; FIG. 1). Additional detail on suitable activities is provided above in reference to FIGS. 3A-30.

In some embodiments, the qualitative descriptor of the user 120's physiological state is displayed in a first portion of a user interface on the display, and the method 800 further includes detecting (834-*a*) a user input within the first portion of the user interface (e.g., a scrolling input received in a substantially downward direction). In some embodiments, the method 800 includes, in response to detecting the user input within the first portion of the user interface, causing the wrist-wearable device 110 to display (834-*b*) an additional portion of the user interface that includes a user interface object that, when selected, causes the wrist-wearable device to begin monitoring the user's performance of the activity. In some embodiments, method 800 further includes receiving a selection of the user interface object from within the additional portion of the user interface and, in response, monitoring the user's performance of the (selected) activity.

In some embodiments, the user interface object is (836) a first user interface object, and displaying the user interface object also includes displaying a second user interface object that, when selected, causes the wrist-wearable device 110 to schedule a future performance of the activity. In some embodiments, displaying (838) the additional portion of the user interface also includes presenting on the display an explanation as to why the activity has been selected as appropriate for the user. Additional examples of the user interface objects are provided above in reference to FIGS. 3A-30. In some embodiments, the explanation can include a short description as to the activity that has been selected as appropriate for the user. By including a such short description alongside the suggested activity, the methods 800 described herein help ensure that users have insights into the recommendations, which helps users trust and follow the recommended actions over time rather than ignore them. In some embodiments, in accordance with a determination that the qualitative descriptor for the user's physiological state indicates that the user has a low energy level, determining an activity for the user to perform in the physical world includes determining (840) at least two activities for the user to perform in the physical world, and the additional portion of the user interface includes respective user interface elements associated with each of the at least two activities for the user to perform in the physical world. In some embodiments, displaying (842) the additional portion of the user interface also includes displaying another user interface element that, when selected, pauses streaks representing performance of physical activities by the user. Pausing activity streaks is discussed above in reference to FIGS. 3A-30.

In some embodiments, the method 800 further includes after monitoring the user's performance of the activity, monitoring (844-*a*) via the one or more sensors that are in communication with the wrist-wearable device 110 new values for the plurality of physiological parameters for the user wearing the wrist-wearable device. The method 800 further includes comparing (844-*b*) the new values for the plurality of physiological parameters to the baseline values for the physiological parameters. Based on the comparing of the new values to the baseline values, the method 800 includes determining (844-*c*) a new qualitative descriptor of the user's physiological state from among the set of three or more predefined qualitative descriptors. In some embodiments, after the determining (844-*c*), the method 800 includes presenting (844-*d*) on the display that is in communication with the wrist-wearable device the new qualitative descriptor of the user's physiological state without displaying a numeric score representing the user's physiological state. In some embodiments, determining an activity for the user to perform in the physical world that is predicted to be suitable for the user based on the qualitative descriptor of the user's physiological state also includes determining (846) at least one other user with whom the user should perform the physical activity, and providing a recommendation on the display that the user should perform the physical activity with the at least one other user 120.

In some embodiments, the qualitative descriptor is (848) presented on the display along with a background color associated with the qualitative descriptor, and each respective predefined qualitative descriptor in the set of three or more predefined qualitative descriptors is associated with a different background color. As non-limiting examples, the different shading and/or gradients used in FIGS. 1A-2C illustrate that at least three different colors can be displayed in conjunction with each of the at least three different predefined qualitative descriptors. In particular, FIG. 2A shows that a first color (e.g., green) can be associated with a first predefined qualitative descriptor (e.g., associated with a high energy or fuel level); FIG. 2B shows that a second color (e.g., blue) can be associated with a second predefined qualitative descriptor (e.g., associated with a medium energy or fuel level); and FIG. 2C shows that a third color (e.g., purple) can be associated with a third predefined qualitative descriptor (e.g., associated a low energy or fuel level). In some embodiments, the colors are selected based on experimental user studies to ensure that the colors are calming and soothing to users, and the colors can be displayed with a gradient treatment such that more color is present in a certain portion of the display relative to other portions of the display.

In some embodiments, presenting the qualitative descriptor on the display also includes presenting (850) information to the user regarding the values for the plurality of physiological parameters to provide the user with information as to how the qualitative descriptor was determined. As one example, FIGS. 2A-2C show that the display can also include representations of three different physiological parameters (e.g., icons representing HRV, RHR, and Sleep, respectively) along with an indication (e.g., whether each icon is filled in or empty) of whether the user's value for that physiological parameter is within an expected range. Addition examples are provided in FIGS. 3A-30. In some embodiments, the method 800 further includes, while presenting information to the user regarding the values for the plurality of physiological parameters, detecting (852-*a*) another user input within a second portion of the user interface. The method 800 includes, in response to detecting the user input within the second portion of the user interface, displaying (852-*b*) a third portion of the user interface that includes displaying ranges of values for at least one physiological parameter of the plurality of the physiological parameters within the additional portion of the user interface. Examples of the specific ranges are described above in reference to FIGS. 3D-3F.

In some embodiments, the method 800 includes, before determining the qualitative descriptor, providing (854) a description of how qualitative descriptors of the user's physiological state will be determined by the wrist-wearable device and an explanation of research behind the use of qualitative descriptors of the user's physiological state. In some embodiments, the method 800 further includes, before determining the qualitative descriptor, providing (856) a description about values for physiological parameters that will be collected in conjunction with determinations of qualitative descriptors of the user's physiological state by the wrist-wearable device.

Figure 9A:
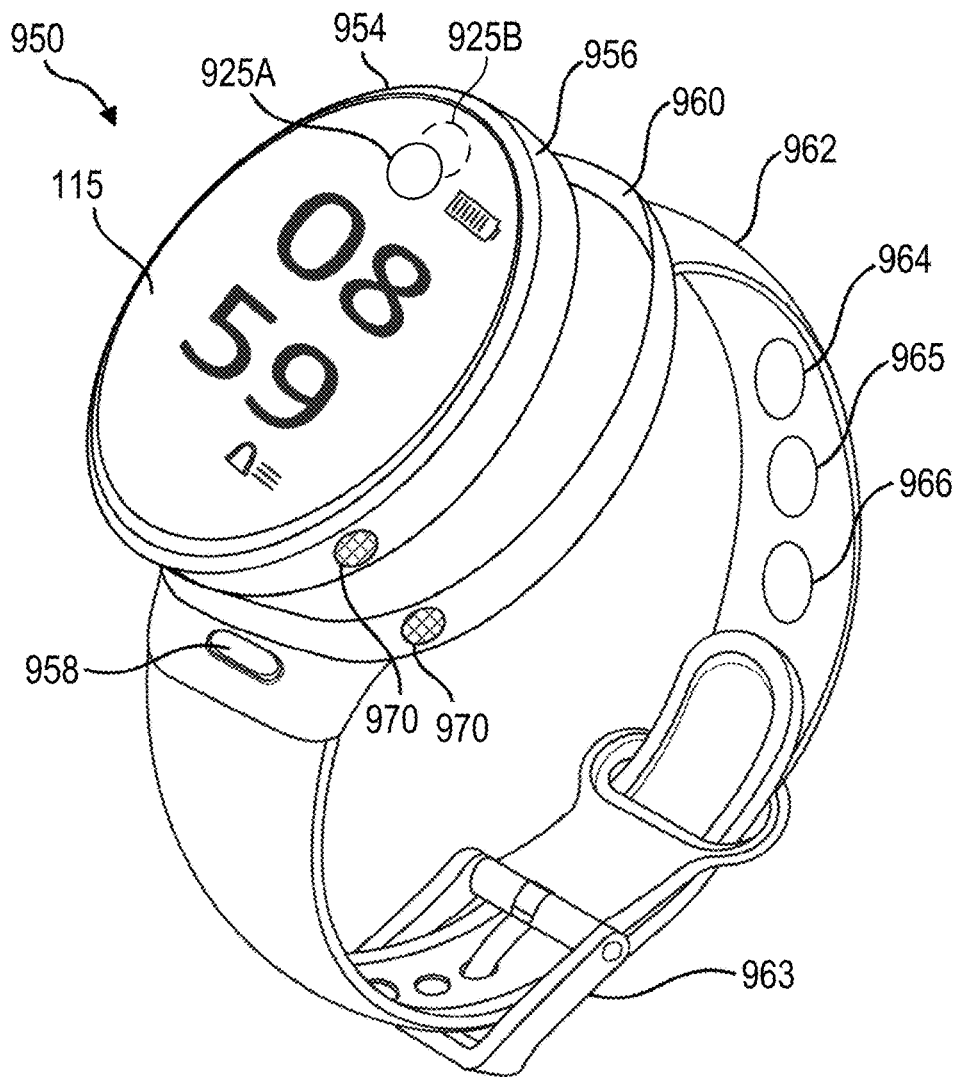
FIGS. 9A and 9B illustrate an example wrist-wearable device, in accordance with some embodiments.
Figure 9B:
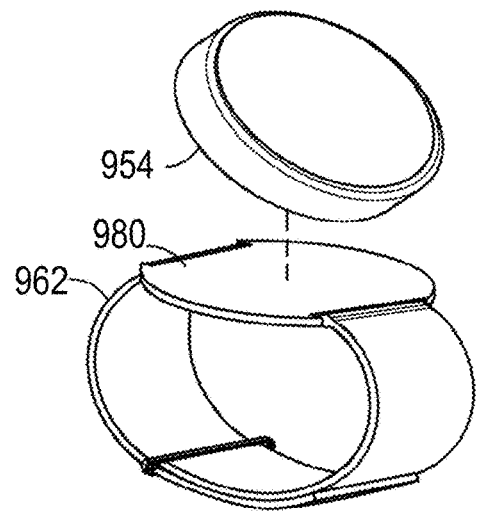

FIGS. 9A and 9B illustrate an example wrist-wearable device 950, in accordance with some embodiments. The wrist-wearable device 950 is an instance of the wrist-wearable device 110 described in reference to FIGS. 1A-8E and 11A-11C, such that wrist-wearable device 110 should be understood to have the features of wrist-wearable device 950 and vice versa. FIG. 9A illustrates a perspective view of the wrist-wearable device 950 that includes a watch body 954 decoupled from a watch band 962. Watch body 954 and watch band 962 can have substantially rectangular or circular shapes and can be configured to allow a user to wear the wrist-wearable device 950 on a body part (e.g., a wrist). The wrist-wearable device 950 can include a retaining mechanism 963 (e.g., a buckle, a hook and loop fastener) for securing watch band 962 to the user's wrist. The wrist-wearable device 950 can also include a coupling mechanism 960 (e.g., a cradle) for detachably coupling capsule or watch body 954 (via a coupling surface 956 of the watch body 954) to watch band 962.

The wrist-wearable device 950 can perform various functions associated with measuring physiological parameters and determining a qualitative descriptor as described with reference to FIGS. 1A-8E and 11A-11C. As will be described in more detail below with reference to FIG. 10, functions executed by the wrist-wearable device 950 can include, without limitation, display of visual content to the user (e.g., visual content displayed on display screen 915), sensing user input (e.g., sensing a touch on button 958, sensing biometric data on sensor 964, sensing ECG, EMG, EEG signals on sensor 965), messaging (e.g., text, speech, video), image capture, wireless communications (e.g., cellular, near field, Wi-Fi, personal area network), location determination, financial transactions, providing haptic feedback, alarms, notifications, biometric authentication, health monitoring, sleep monitoring, heart rate monitoring, etc. These functions can be executed independently in watch body 954, independently in watch band 962, and/or in communication between watch body 954 and watch band 962.

The watch band 962 can be configured to be worn by a user such that an inner surface of the watch band 962 is in contact with the user's skin. When worn by a user, sensor 964 is in contact with the user's skin. The sensor 964 can be a biosensor that senses a user's heart rate, saturated oxygen level, temperature, sweat level, muscle intentions, or a combination thereof. The watch band 962 can include multiple sensors 964 that can be distributed on an inside and/or an outside surface of the watch band 962. Additionally, or alternatively, the watch body 954 can include the same or different sensors than the watch band 962 (or the watch band 962 can include no sensors at all in some embodiments). For example, multiple sensors can be distributed on an inside and/or an outside surface of watch body 954. As described below with reference to FIGS. 10, the watch body 954 can include, without limitation, front-facing image sensor 925A and/or rear-facing image sensor 925B (each an instance of image sensor 135; FIG. 1), a biometric sensor, an inertial measurement unit (IMU), a heart rate sensor, a saturated oxygen sensor, a neuromuscular sensor(s) (e.g., EMG sensors 1046 FIG. 10), an altimeter sensor, a temperature sensor, a bioimpedance sensor, a pedometer sensor, an optical sensor, a touch sensor, a sweat sensor, etc. The sensor 964 can also include a light sensor (e.g., an infrared light sensor, a visible light sensor) that is configured to track a position and/or motion of watch body 954 and/or watch band 962. Watch band 962 can transmit the data acquired by the sensor 964 to watch body 954 using a wired communication method (e.g., a UART, a USB transceiver, etc.) and/or a wireless communication method (e.g., near field communication, Bluetooth™, etc.). Watch band 962 can be configured to operate (e.g., to collect data using sensor 964) independent of whether watch body 954 is coupled to or decoupled from watch band 962.

The watch band 962 and/or watch body 954 can include a haptic device 966 (e.g., a vibratory haptic actuator) that is configured to provide haptic feedback (e.g., a cutaneous and/or kinesthetic sensation, etc.) to the user's skin. The sensor 964 and/or haptic device 966 can be configured to operate in conjunction with multiple applications including, without limitation, health monitoring, social media, game playing, and artificial reality (e.g., the applications associated with artificial reality).

Signals from sensor 965 can be used to provide a user with an enhanced interaction with the graphical user interface, as a qualitative descriptor will be presented to the user. Signals from sensor 965 can be obtained (e.g., sensed and recorded) by one or more sensors 965 of watch band 962. Although FIG. 9A shows a sensor 965, watch band 962 can include a plurality of sensors 965 arranged circumferentially on an inside surface of watch band 962 such that the plurality of sensors 965 contact the skin of the user. Watch band 962 can include a plurality of sensors 965 arranged circumferentially on an inside surface of watch band 962. Sensor 965 can sense and record signals from the user as the user performs muscular activities (e.g., movements, sleep, work, etc.). The activations performed by the user can include static gestures, such as placing the user's hand palm down on a table, sleeping, etc.; dynamic gestures, such as typing on a laptop; and covert gestures that are imperceptible to another person, such as slightly tensing a joint by co-contracting opposing muscles or using sub-muscular activations.

The wrist-wearable device 950 can include a coupling mechanism (also referred to as a cradle) for detachably coupling watch body 954 to watch band 962. A user can detach watch body 954 from watch band 962 in order to reduce the encumbrance of the wrist-wearable device 950 to the user. The wrist-wearable device 950 can include a coupling surface 956 on the watch body 954 and/or watch band coupling mechanism(s) 960 (e.g., a cradle, a tracker band, a support base, a clasp). A user can perform any type of motion to couple watch body 954 to watch band 962 and to decouple watch body 954 from watch band 962. For example, a user can twist, slide, turn, push, pull, or rotate watch body 954 relative to watch band 962, or a combination thereof, to attach watch body 954 to watch band 962 and to detach watch body 954 from watch band 962.

As shown in the example of FIG. 9A, watch band coupling mechanism 960 can include a type of frame or shell that allows watch body 954 coupling surface 956 to be retained within watch band coupling mechanism 960. Watch body 954 can be detachably coupled to watch band 962 through a friction fit, magnetic coupling, a rotation-based connector, a shear-pin coupler, a retention spring, one or more magnets, a clip, a pin shaft, a hook and loop fastener, or a combination thereof. In some examples, watch body 954 can be decoupled from watch band 962 by actuation of release mechanism 970. The release mechanism 970 can include, without limitation, a button, a knob, a plunger, a handle, a lever, a fastener, a clasp, a dial, a latch, or a combination thereof.

The wrist-wearable device 950 can include a single release mechanism 970 or multiple release mechanisms 970 (e.g., two release mechanisms 970 positioned on opposing sides of the wrist-wearable device 950, such as spring-loaded buttons). As shown in FIG. 9A, the release mechanism 220 can be positioned on watch body 954 and/or watch band coupling mechanism 960. Although FIG. 9A shows release mechanism 970 positioned at a corner of watch body 954 and at a corner of watch band coupling mechanism 960, the release mechanism 970 can be positioned anywhere on watch body 954 and/or watch band coupling mechanism 960 that is convenient for a user of wrist-wearable device 950 to actuate. A user of the wrist-wearable device 950 can actuate the release mechanism 970 by pushing, turning, lifting, depressing, shifting, or performing other actions on the release mechanism 970. Actuation of the release mechanism 970 can release (e.g., decouple) the watch body 954 from the watch band coupling mechanism 960 and the watch band 962, allowing the user to use the watch body 954 independently from watch band 962. For example, decoupling the watch body 954 from the watch band 962 can allow the user to capture images using rear-facing image sensor 925B.

FIG. 9B is a perspective view of another example of the wrist-wearable device 950. The wrist-wearable devices 950 of FIG. 9B can include a watch body interface 980 (another example of a cradle for the capsule portion of the device 202). The watch body 954 can be detachably coupled to the watch body interface 980. Watch body 954 can be detachably coupled to watch body interface 980 through a friction fit, magnetic coupling, a rotation-based connector, a shear-pin coupler, a retention spring, one or more magnets, a clip, a pin shaft, a hook and loop fastener, or a combination thereof.

In some examples, watch body 954 can be decoupled from watch body interface 980 by actuation of a release mechanism. The release mechanism can include, without limitation, a button, a knob, a plunger, a handle, a lever, a fastener, a clasp, a dial, a latch, or a combination thereof. In some examples, the wristband system functions can be executed independently in watch body 954, independently in watch body interface 980, and/or in communication between watch body 954 and watch body interface 980. Watch body interface 980 can be configured to operate independently (e.g., execute functions independently) from watch body 954. Additionally, or alternatively, watch body 954 can be configured to operate independently (e.g., execute functions independently) from watch body interface 980. As will be described in more detail below with reference to the block diagram of FIG. 10, watch body interface 980 and/or watch body 954 can each include the independent resources required to independently execute functions. For example, watch body interface 980 and/or watch body 954 can each include a power source (e.g., a battery), a memory, data storage, a processor (e.g., a CPU), communications, a light source, and/or input/output devices.

In this example, watch body interface 980 can include all of the electronic components of watch band 962. In additional examples, one or more electronic components can be housed in watch body interface 980 and one or more other electronic components can be housed in portions of watch band 962 away from watch body interface 980.

FIG. 10 is a block diagram of a wrist-wearable device system 1000, according to at least one embodiment of the present disclosure. The wrist-wearable device 110 described in detail above is an example wrist-wearable device system 1000, so wrist-wearable device 110 will be understood to include the components shown and described for system 1000 below. The wrist-wearable device system 1000 can have a split architecture (e.g., a split mechanical architecture, a split electrical architecture) between a watch body 1004 (e.g., capsule or watch body 954) and a watch band 1012 (e.g., a band portion 914), which was described above in reference to FIGS. 9A and 9B. Each of watch body 1004 and watch band 1012 can have a power source, a processor, a memory, sensors, a charging device, and a communications device that enables each of watch body 1004 and watch band 1012 to execute computing, controlling, communication, and sensing functions independently in watch body 1004, independently in watch band 1012, and/or in communication between watch body 1004 and watch band 1012.

For example, watch body 1004 can include battery 1028, CPU 1026, storage 1002, heart rate sensor 1058, EMG sensor 1046, SpO2 sensor 1054, altimeter 1048, IMU 1042, RAM 1003, charging input 1030 and communication devices NFC 1015, LTE 1018, and WiFi/Bluetooth™ 1020. Similarly, watch band 1012 can include battery 1038, microcontroller unit 1052, memory 1050, heart rate sensor 1058, EMG sensor 1046, SpO2 sensor 1054, altimeter 1048, IMU 1042, charging input 1034 and wireless transceiver 1040. In some embodiments, the watch body 1004 and/or the watch band 1012 include one or more ECG sensors, EEG sensors, mechanomyography (MMG) sensors, sonomyography (SMG) sensors, and electrical impedance tomography (EIT) sensors. In some examples, a level of functionality of at least one of watch band 1012 or watch body 1004 can be modified when watch body 1004 is detached from watch band 1012. The level of functionality that can be modified can include the functionality of at least one sensor (e.g., heart rate sensor 1058, EMG sensor 1046). Each of watch body 1004 and watch band 1012 can execute instructions stored in storage 1002 and memory 1050, respectively, that enable at least one sensor (e.g., heart rate sensor 1058, EMG sensor 1046) in watch band 1012 to acquire data when watch band 1012 is detached from watch body 1004 and when watch band 1012 is attached to watch body 1004.

Watch body 1004 and watch band 1012 can further execute instructions stored in storage 1002 and memory 1050, respectively, that enable watch band 1012 to transmit the acquired data to watch body 1004 using wired communications 1027 and/or wireless transceiver 1040. For example, watch body 1004 can display visual content to a user on touchscreen display 1013 (e.g., an instance of display 115) and play audio content on speaker 1074. Watch body 1004 can receive user inputs such as audio input from microphone 1072 and touch input from buttons 1024. Watch body 1004 can also receive inputs associated with a user's location and/or surroundings. For example, watch body 1004 can receive location information from GPS 1016 and/or altimeter 1048 of watch band 1012.

Watch body 1004 can receive image data from at least one image sensor 1070 (e.g., a camera). Image sensor 1070 can include front-facing image sensor 925A (FIG. 9A) and/or rear-facing image sensor 925B (FIG. 9B). Front-facing image sensor 925A and/or rear-facing image sensor 925B can capture wide-angle images of the area surrounding the front-facing image sensor 925A and/or the rear-facing image sensor 925B, such as hemispherical images (e.g., at least hemispherical, substantially spherical), 180-degree images, 360-degree area images, panoramic images, ultra-wide area images, or a combination thereof. In some examples, front-facing image sensor 925A and/or rear-facing image sensor 925B can be configured to capture images having a range between 45 degrees and 360 degrees. Certain input information received by watch body 1004 (e.g., user inputs, etc.) can be communicated to watch band 1012. Similarly, certain input information (e.g., acquired sensor data, neuromuscular sensor data) received by watch band 1012 can be communicated to watch body 1004.

Watch body 1004 and watch band 1012 can receive a charge using a variety of techniques. In some embodiments, watch body 1004 and watch band 1012 can use a wired charging assembly (e.g., power cords) to receive the charge. Alternatively, or in addition, watch body 1004 and/or watch band 1012 can be configured for wireless charging. For example, a portable charging device can be designed to mate with a portion of watch body 1004 and/or watch band 1012 and wirelessly deliver usable power to a battery of watch body 1004 and/or watch band 1012.

Watch body 1004 and watch band 1012 can have independent power and charging sources to enable each to operate independently. Watch body 1004 and watch band 1012 can also share power (e.g., one can charge the other) via power management IC 1032 in watch body 1004 and power management IC 1036 in watch band 1012. Power management IC 1032 and power management IC 1036 can share power over power and ground conductors and/or over wireless charging antennas.

Wrist-wearable device system 1000 can operate in conjunction with a health-monitoring application that acquires biometric and activity information associated with the user. The health-monitoring application can be designed to provide information to a user that is related to the user's health. For example, wrist-wearable device system 1000 can monitor a user's physical activity by acquiring data from IMU 1042 while simultaneously monitoring the user's heart rate via the heart rate sensor 1058 and saturated blood oxygen levels via SpO2 sensor 1054. CPU 1026 can process the acquired data and display health-related information to the user on touchscreen display 1013.

Wrist-wearable device system 1000 can detect when watch body 1004 and watch band 1012 are connected to one another (e.g., mechanically connected and/or electrically or magnetically connected) or detached from one another. For example, pin(s), power/ground connections 1060, wireless transceiver 1040, and/or wired communications 1027 can detect whether watch body 1004 and watch band 1012 are mechanically and/or electrically or magnetically connected to one another (e.g., detecting a disconnect between the one or more electrical contacts of power/ground connections 1060 and/or wired communications 1027). In some examples, when watch body 1004 and watch band 1012 are mechanically and/or electrically disconnected from one another, watch body 1012 has been detached from watch band 1012 as described with reference to FIGS. 9A and 9B), watch body 1004 and/or watch band 1012 can operate with modified level of functionality (e.g., reduced functionality) as compared to when watch body 1004 and watch band 1012 are mechanically and/or electrically connected to one another. The modified level of functionality (e.g., switching from full functionality to reduced functionality and from reduced functionality to full functionality) can occur automatically (e.g., without user intervention) when wrist-wearable device system 1000 determines that watch body 1004 and watch band 1012 are mechanically and/or electrically disconnected from one another and connected to each other, respectively.

Modifying the level of functionality (e.g., reducing the functionality in watch body 1004 and/or watch band 1012) can reduce power consumption in battery 1028 and/or battery 1038. For example, any of the sensors (e.g., heart rate sensor 1058, EMG sensor 1046, SpO2 sensor 1054, altimeter 1048), processors (e.g., CPU 1026, microcontroller unit 1052), communications elements (e.g., NFC 1015, GPS 1016, LTE 1018, WiFi/Bluetooth™ 1020), or actuators (e.g., haptics 1022, 1049) can reduce functionality and/or power consumption (e.g., enter a sleep mode) when watch body 1004 and watch band 1012 are mechanically and/or electrically disconnected from one another. Watch body 1004 and watch band 1012 can return to full functionality when watch body 1004 and watch band 1012 are mechanically and/or electrically connected to one another. The level of functionality of each of the sensors, processors, actuators, and memory can be independently controlled.

As described above, wrist-wearable device system 1000 can detect when watch body 1004 and watch band 1012 are coupled to one another (e.g., mechanically connected and/or electrically connected) or decoupled from one another. In some examples, watch body 1004 can modify a level of functionality (e.g., activate and/or deactivate certain functions) based on whether watch body 1004 is coupled to watch band 1012. For example, CPU 1026 can execute instructions that detect when watch body 1004 and watch band 1012 are coupled to one another and activate front-facing image sensor 925A. CPU 1026 can activate front-facing image sensor 925A based on receiving user input (e.g., a user touch input from touchscreen display 1013, a user voice command from microphone 127, a user gesture recognition input from EMG sensor 1046).

When CPU 1026 detects that watch body 1004 and watch band 1012 are decoupled from one another, CPU 1026 can modify a level of functionality (e.g., activate and/or deactivate additional functions). For example, CPU 1026 can detect when watch body 1004 and watch band 1012 are decoupled from one another and activate rear-facing image sensor 925B. CPU 1026 can activate rear-facing image sensor 925B automatically (e.g., without user input) and/or based on receiving user input (e.g., a touch input, a voice input, a body movement). Automatically activating the rear-facing image sensor 925B can allow a user to take wide-angle images without having to provide user input to activate rear-facing image sensor 925B.

In some examples, rear-facing image can be activated based on an image-capture criterion (e.g., an image quality, an image resolution). For example, rear-facing image sensor 925B can receive an image (e.g., a test image). CPU 1026 and/or rear-facing image sensor 925B can analyze the received test image data and determine whether the test-image data satisfies the image-capture criterion (e.g., the image quality exceeds a threshold, the image resolution exceeds a threshold). Rear-facing image sensor 925B can be activated when the test-image data satisfies the image-capture criterion. Additionally, or alternatively, rear-facing image sensor 925B can be deactivated when the test-image data fails to satisfy the image-capture criterion.

In some examples, CPU 1026 can detect when watch body 1004 is coupled to watch band 1012 and deactivate rear-facing image sensor 925B. CPU 1026 can deactivate rear-facing image sensor 925B automatically (e.g., without user input) and/or based on receiving user input (e.g., a touch input, a voice input, an intention detection). Deactivating the rear-facing image sensor 925B can automatically (e.g., without user input) reduce the power consumption of watch body 1004 and increase the battery charge time in watch body 1004. In some examples, wrist-wearable device system 1000 can include a coupling sensor 1007 that senses whether watch body 1004 is coupled to or decoupled from watch band 1012. Coupling sensor 1007 can be included in any of watch body 1004, watch band 1012, or watch band coupling mechanism 960 of FIGS. 9A and 9B. Coupling sensor 1007 (e.g., a proximity sensor) can include, without limitation, an inductive proximity sensor, a limit switch, an optical proximity sensor, a capacitive proximity sensor, a magnetic proximity sensor, an ultrasonic proximity sensor, or a combination thereof. CPU 1026 can detect when watch body 1004 is coupled to watch band 1012 or decoupled from watch band 1012 by reading the status of coupling sensor 1007.

Figure 11A:
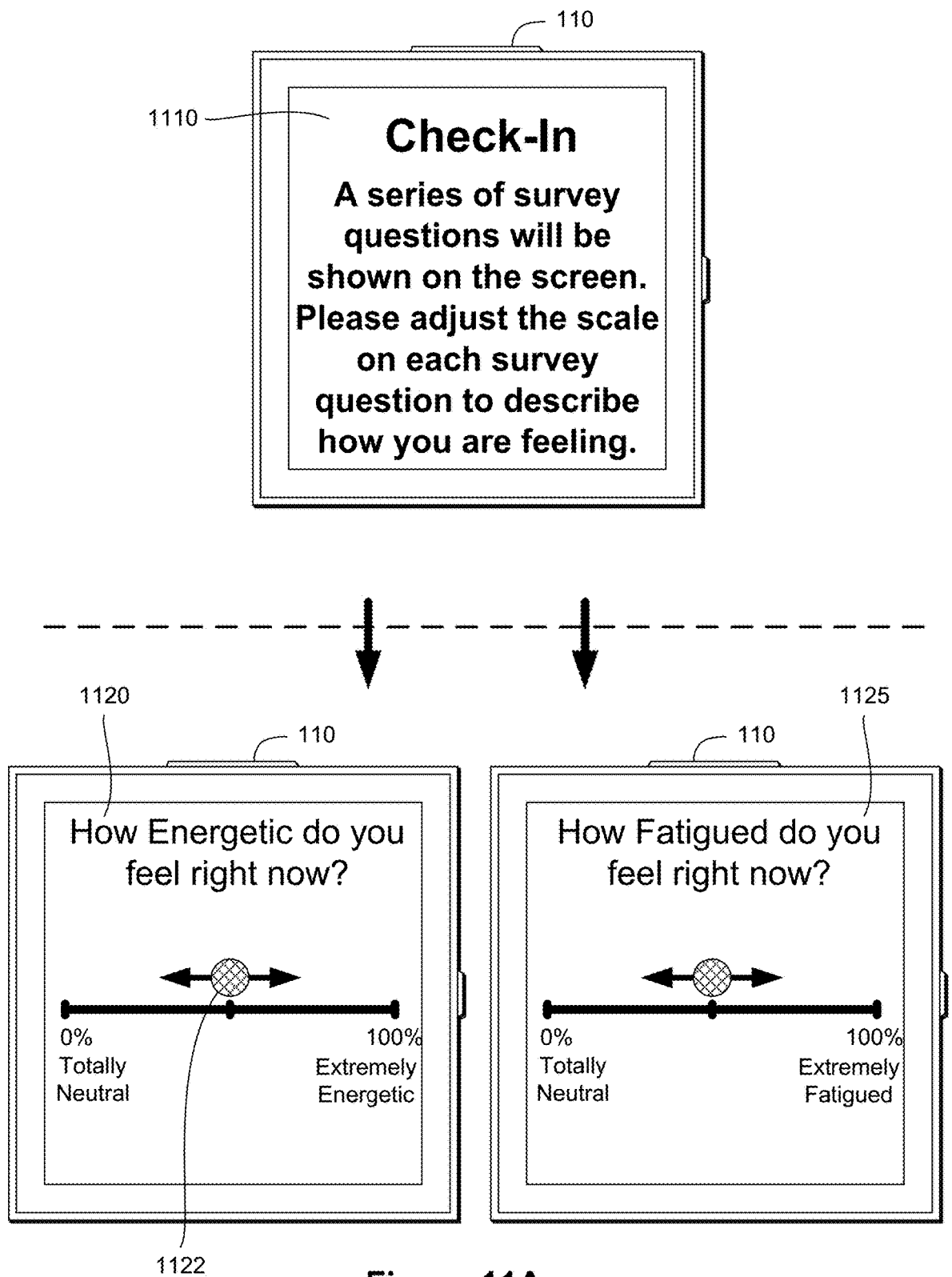
FIG. 11A illustrates user interfaces for obtaining subjective indications of a user's physiological state, in accordance with some embodiments.

FIG. 11A illustrates user interfaces for obtaining subjective indications of a user 120's (FIGS. 1A-1F) current experience or energy level, in accordance with some embodiments. In some embodiments the wrist-wearable device 110 displays a subjective task instructions user interface 1110, including instructions for participating in subjective tasks for obtaining subjective indications. Subjective tasks include visual analogue scales (VASs) configured to collect subjective outputs from the user 120 (i.e., user's description of how they feel). The subjective outputs collected from the user 120 using the VAS are used in conjunction with the objective outputs collected from cognitive tasks (described below in reference to FIGS. 11B and 11C) and a plurality of physiological parameters, monitored using one or more sensors (e.g., a heart rate sensor 1058, an EMG sensor 1046, SpO2 sensor 1054; FIG. 10), for the user 120 wearing the wrist-wearable device to determine the qualitative descriptor (as described above in reference to FIGS. 1A-1F).

In some embodiments, the subjective outputs are used to validate measures of the user 120's current physiological state (e.g., how accurate is the user's determined physiological state compared to the subjective outputs). The subjective outputs measure the user 120's current experience, in particular the user 120's fatigue, energy, mood, motivation, and stress. In some embodiments, the subjective outputs are collected from the user 120 using daily surveys. The daily surveys can be provided to the user 120 via a web-based application and/or a mobile application (on the wrist-wearable device 110 and/or other computing device, such as a smartphone, laptop, artificial-reality glasses). The daily surveys include one or more of brief VASs (as shown in a first VAS user interface 1120 and a second VAS user interface 1125) to collect subjective outputs. In some embodiments, the daily surveys include at least one set of VAS and at least one reaction time-based task (as described below in reference to FIGS. 11B and 11C).

Figure 11B:
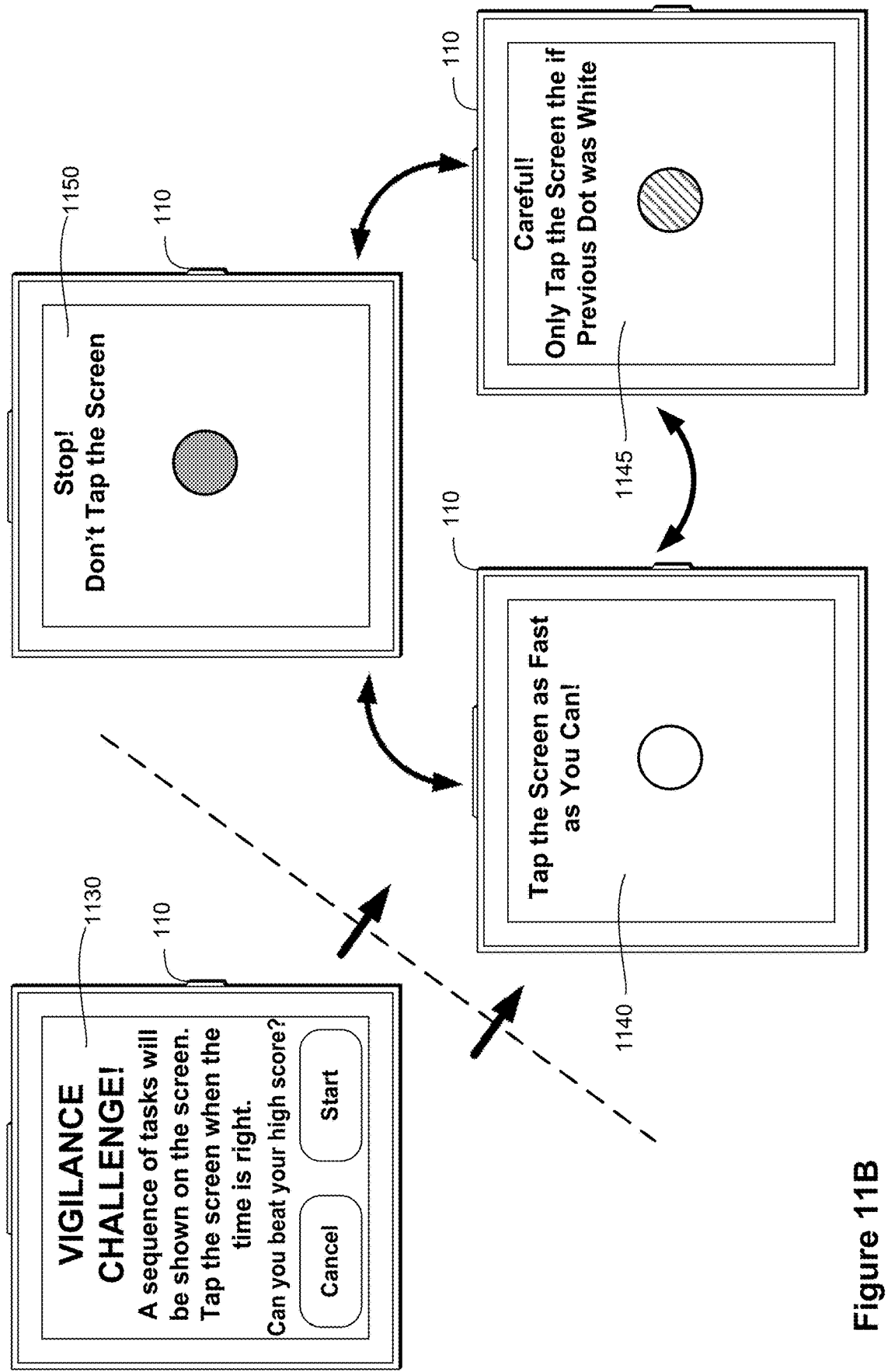
FIGS. 11B and 11C illustrate user interfaces for obtaining objective indications of a cognitive or motor function of a user, in accordance with some embodiments.

A VAS is robust to daily variability and is grounded in the individual's experience. The first VAS user interface 1120 illustrates a first VAS requesting information on how energetic the user 120 currently feels. The first VAS user interface 1120 includes one or more moveable objects (e.g., a slidable user interface object 1122) that allow the user 120 to specify whether he or she feels totally neutral (0%) or extremely energetic (100%). The second VAS user interface 1125 illustrates a second VAS requesting information on how fatigued the user 120 currently feels. The user 120 can specify, via one or more moveable objects in the second VAS user interface 1125, whether he or she feels totally neutral (0%) or extremely fatigued (100%). FIG. 11B illustrates a second VAS requesting information. In some embodiments, the daily surveys include additional VAS items than those shown in the first VAS user interface 1120 and the second VAS user interface 1125. A non-exhaustive list of the VAS items that can be provided to the user include how negative the user 120 currently feels, how positive the user 120 currently feels, how stressed the user 120 currently feels, or how happy the user 120 currently feels. In some embodiments, the total survey time for daily VASs is less than one minute. In some embodiments, the user 120 can request to participate in an extensive survey, distinct from the daily survey, that has a total survey that takes at least five minutes.

Figure 11C:
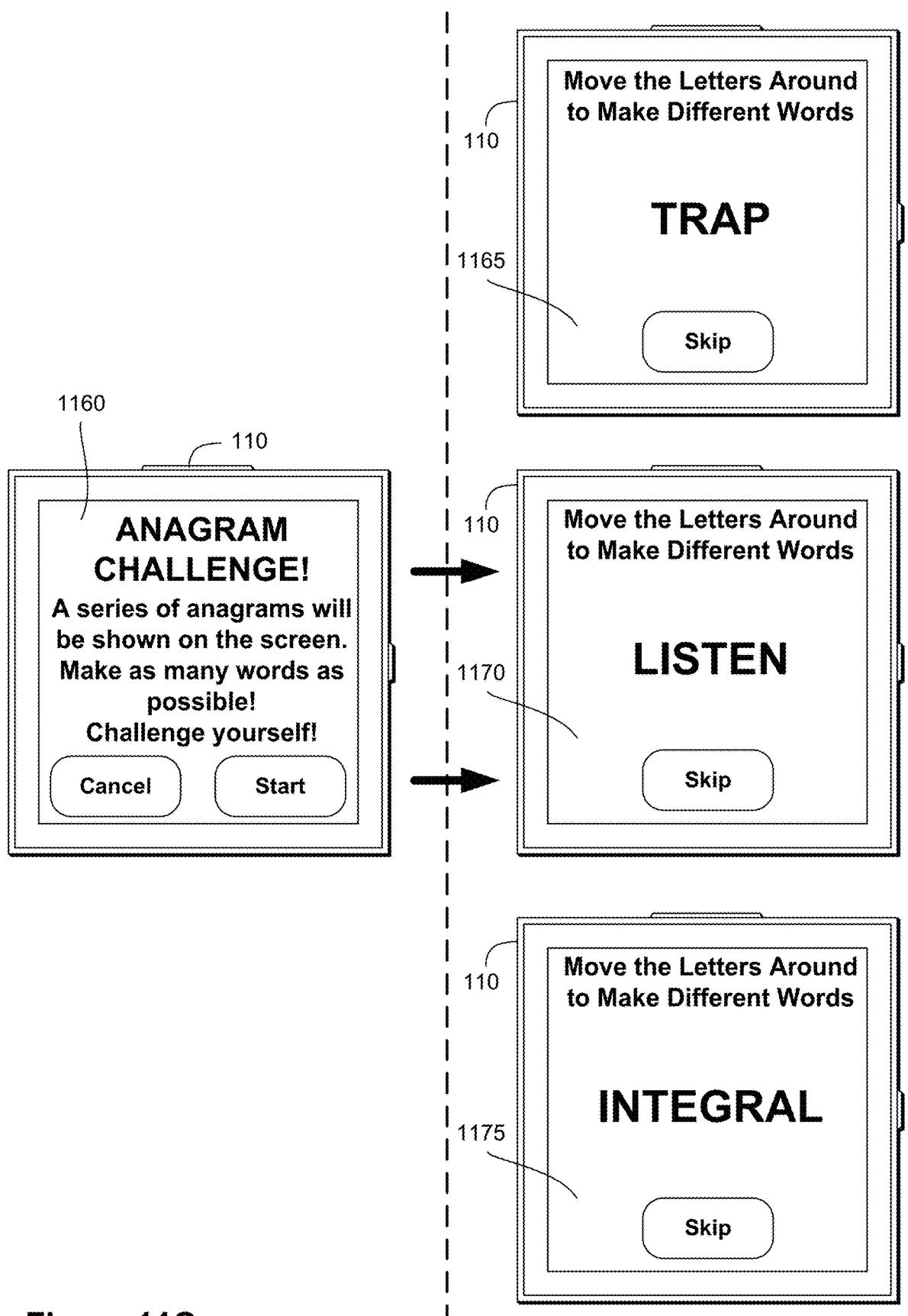

FIGS. 11B-11C illustrate user interfaces for obtaining objective indications of a cognitive or motor function of a user 120, in accordance with some embodiments. FIG. 11B illustrates a psychomotor vigilance cognitive task, and FIG. 11C illustrates anagram cognitive tasks. The cognitive tasks shown in FIGS. 11B and 11C are used to collect objective outputs from the user 120. The cognitive tasks in FIGS. 11B and 11C are reaction time-based tasks that are widely utilized to assess current functioning on cognitive and motor dimensions of the user 120. Scores for the cognitive tasks can be affected by physiological functioning, sleep, mood, and motivation. The reaction time-based tasks provide robust to daily variability and can be compared to the individual's baseline. In some embodiments, each reaction time-based task takes approximately one minute to complete. In some embodiments, the daily survey includes at least one reaction time-based task. Alternatively, in some embodiments, the daily survey includes more than one reaction time-based task. The objective outputs collected from the user 120 via the cognitive tasks shown in FIGS. 11B and 11C are used in conjunction with subjective outputs shown in FIG. 11A and the plurality of physiological parameters for the user 120 wearing the wrist-wearable device to determine the qualitative descriptor.

In some embodiments, the objective outputs are used to validate measures of the user 120's current physiological state (e.g., how accurate is the user's determined physiological state compared to the objective outputs). The objective outputs measure the user 120's current functioning, in particular the user 120's motor functioning, cogitative capacity, problem solving and/or impulse control. In some embodiments, the objective outputs are collected from the user 120 using daily surveys. As described above, the daily surveys can be provided to the user via a web-based application and/or a mobile application (on the wrist-wearable device 110 and/or other computing device such as a smartphone, laptop, artificial-reality glasses). The daily surveys include one or more of brief reaction time-based tasks to collect objective outputs (such as the psychomotor vigilance task and the anagram task shown in FIGS. 11B and 11C, respectively). In some embodiments, the daily surveys include at least one set of VAS and at least one reaction time-based task.

Turning to FIG. 11B, in some embodiments the wrist-wearable device 110 displays a first objective task instructions user interface 1130 including instructions for participating in a psychomotor vigilance cognitive task for obtaining objection indications of the user 120. The psychomotor vigilance task is configured to measure motor functioning, impulse control, attention, and/or discrimination. In some embodiments, the psychomotor vigilance task instructs the user 120 to (i) tap the screen as fast as the user 120 can for 30 seconds, (ii) tap the screen whenever a first colored dot appears as quickly as the user 120 can, (iii) only tap the screen when a second colored dot appears after the first colored dot, and/or (iv) to never tap on the screen when a third colored dot appears. The first, second, and third colored dots are represented in FIG. 11B via individual user interfaces. For example, a first psychomotor vigilance task user interface 1140 includes the first colored dot (e.g., a white dot), a second psychomotor vigilance task user interface 1145 includes the second colored dot (e.g., a pattern filled dot), and a third psychomotor vigilance task user interface 1150 includes the third colored dot (e.g., a grey dot). In some embodiments, the wrist-wearable device 110 switches between the first, second, and third psychomotor vigilance task user interface 1140, 1145, and 1150 during performance of the task to assess the user 120's score. In some embodiments, scores for the psychomotor vigilance task are determined as follows: gross motor functioning is determined based on the rate of tapping to first condition (i.e., condition (i)), attention is determined based on the rate of response to second condition (i.e., condition (ii)), discrimination is based on the rate of response to third condition (i.e., condition (iii)), and/or impulse control is determined based on the error rate for third and fourth conditions (i.e., conditions (iii) and (iv)).

Turning to FIG. 11C, in some embodiments the wrist-wearable device 110 displays a second objective task instructions user interface 1160 including instructions for participating in an anagram cognitive task for obtaining objection indications of the user 120. The anagram cognitive task is configured to measure executive functioning and/or motivation. In some embodiments, the anagram cognitive task instructs the user 120 to (i) solve a displayed anagram as quickly and accurately as possible and (ii) skip the anagram if the user 120 finds the currently displayed anagram too difficult. FIG. 11C includes user interfaces for three distinct anagrams displayed to the user 120. A first anagram user interface 1165 includes a first word (e.g., TRAP), a second anagram user interface 1170 includes a second word (e.g., LISTEN), and a third anagram user interface 1175 includes a third word (e.g., INTEGRAL). The example anagrams are non-exhaustive. Any anagram can be displayed in a respective user interface. In some embodiments, scores for the anagram task are determined as follows: executive functioning is determined based on the mean rate of correct responses and/or the difficulty of anagram, and motivation is determined based on the rate and/or frequency of anagram skips and/or the difficulty of anagram.

The above-identified VASs and reaction time-based tasks are non-limiting examples of subjective and objective tasks for collection user outputs. The skilled artisan will appreciate that the different tasks, surveys, queries, and/or tests can be used to collect subjective and objective outputs from the user.

In some embodiments, a machine-learning model is trained using the subjective outputs, the objective outputs, and the baseline values for the physiological parameters of the user 120. In some embodiments, the machine-learning model is improved iteratively. In some embodiments, the machine-learning model increases generalizability by expanding research to diverse populations and increasing the input and output space to include other sensor data and construct measures. In some embodiments, more than one machine-learning model is trained. The one or more machine-learning models are trained to identify shared relationships between input (e.g., each of the measured plurality of physiological parameters) and output measures (e.g., objective and subjective outputs).

Although some examples provided with reference to FIGS. 1A-11C are discussed in the context of EMG, ECG, and EEG sensors as the example sensors, other sensors can also include, but are not limited to, mechanomyography (MMG) sensors, sonomyography (SMG) sensors, and electrical impedance tomography (EIT) sensors. The approaches described herein may also be implemented in wearable interfaces that communicate with computer hosts through wires and cables (e.g., USB cables, optical fiber cables), in addition to the wireless communication channels described in conjunction with various embodiments herein. Further embodiments also include various subsets of the above embodiments, including embodiments in FIGS. 1A-11C combined or otherwise rearranged.

It will be understood that, although the terms "first," "second," etc., may be used herein to describe various elements, these elements should not be limited by these terms. These terms are only used to distinguish one element from another.

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" can be construed to mean "when" or "upon" or "in response to determining" or "in accordance with a determination" or "in response to detecting" that a stated condition precedent is true, depending on the context. Similarly, the phrase "if it is determined [that a stated condition precedent is true]" or "if [a stated condition precedent is true]" or "when [a stated condition precedent is true]" can be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the claims to the precise forms disclosed. Many modifications and variations are possible in view of the above teachings. The embodiments were chosen and described in order to best explain principles of operation and practical applications, to thereby enable others skilled in the art.

What is claimed is:

1. A method of presenting a qualitative descriptor of a user's physiological state at a wrist-wearable device, the method comprising:
   presenting, on a display that is in communication with the wrist-wearable device, a description of how a set of three or more predefined qualitative descriptors of a user's physiological state will be determined by the wrist-wearable device and an explanation of research behind the use of qualitative descriptors of the user's physiological state;
monitoring, via one or more sensors that are in communication with the wrist-wearable device, values for a plurality of physiological parameters for a user wearing the wrist-wearable device;
comparing the values for the plurality of physiological parameters to baseline values for the physiological parameters, the baseline values being determined based on values for the plurality of physiological parameters that were measured over a predetermined period of time;
based on the comparing, determining a qualitative descriptor of the user's physiological state from among the set of three or more predefined qualitative descriptors; and
presenting, on the display that is in communication with the wrist-wearable device, the qualitative descriptor of the user's physiological state without displaying a numeric score representing the user's physiological state.

2. The method of claim 1, further comprising:
determining an activity for the user to perform in the physical world that is predicted to be suitable for the user based on the qualitative descriptor of the user's physiological state.

3. The method of claim 2, wherein the qualitative descriptor of the user's physiological state is displayed in a first portion of a user interface on the display, and the method further comprises:
detecting a user input within the first portion of the user interface; and
in response to detecting the user input within the first portion of the user interface, displaying an additional portion of the user interface that includes a user interface object that, when selected, causes the wrist-wearable device to begin monitoring the user's performance of the activity.

4. The method of claim 3, further comprising:
after monitoring the user's performance of the activity:
monitoring, via the one or more sensors that are in communication with the wrist-wearable device, new values for the plurality of physiological parameters for the user wearing the wrist-wearable device;
comparing the new values for the plurality of physiological parameters to the baseline values for the physiological parameters;
based on the comparing of the new values to the baseline values, determining a new qualitative descriptor of the user's physiological state from among the set of three or more predefined qualitative descriptors; and
presenting, on the display that is in communication with the wrist-wearable device, the new qualitative descriptor of the user's physiological state without displaying a numeric score representing the user's physiological state.

5. The method of claim 3, wherein the user interface object is a first user interface object, and the displaying the user interface object also includes displaying a second user interface object that, when selected, causes the wrist-wearable device to schedule a future performance of the activity.

6. The method of claim 5, wherein the displaying the additional portion of the user interface also includes presenting on the display an explanation as to why the activity has been selected as appropriate for the user.

7. The method of claim 3, further comprising:
in accordance with a determination that the qualitative descriptor for the user's physiological state indicates that the user has a low energy level, the determining an activity for the user to perform in the physical world includes determining at least two activities for the user to perform in the physical world, and the additional portion of the user interface includes respective user interface elements associated with each of the at least two activities for the user to perform in the physical world.

8. The method of claim 2, wherein the determining an activity for the user to perform in the physical world that is predicted to be suitable for the user based on the qualitative descriptor of the user's physiological state also includes determining at least one other user with whom the user should perform the physical activity, and providing a recommendation on the display that the user should perform the physical activity with the at least one other user.

9. The method of claim 1, further comprising:
before determining the qualitative descriptor, providing a description about values for physiological parameters that will be collected in conjunction with determinations of qualitative descriptors of the user's physiological state by the wrist-wearable device.

10. The method of claim 1, wherein the baseline values are determined based on values for the plurality of physiological parameters that were measured over a predetermined period of time while the user was in a state of deep sleep.

11. A non-transitory, computer-readable storage medium including instructions that, when executed by a wrist-wearable device, cause the wrist-wearable device to perform or cause performance of:
presenting, on a display that is in communication with the wrist-wearable device, a description of how a set of three or more predefined qualitative descriptors of a user's physiological state will be determined by the wrist-wearable device and an explanation of research behind the use of qualitative descriptors of the user's physiological state;
monitoring, via one or more sensors that are in communication with a wrist-wearable device, values for a plurality of physiological parameters for a user wearing the wrist-wearable device;
comparing the values for the plurality of physiological parameters to baseline values for the physiological parameters, the baseline values being determined based on values for the plurality of physiological parameters that were measured over a predetermined period of time;
based on the comparing, determining a qualitative descriptor of the user's physiological state from among the set of three or more predefined qualitative descriptors; and
presenting, on the display that is in communication with the wrist-wearable device, the qualitative descriptor of the user's physiological state without displaying a numeric score representing the user's physiological state.

12. The non-transitory, computer-readable storage medium of claim 11, wherein the instructions, when executed by the wrist-wearable device, further cause the wrist-wearable device to perform:

determining an activity for the user to perform in the physical world that is predicted to be suitable for the user based on the qualitative descriptor of the user's physiological state.

13. The non-transitory, computer-readable storage medium of claim 12, wherein the qualitative descriptor of the user's physiological state is displayed in a first portion of a user interface on the display, and the instructions, when executed by the wrist-wearable device, further cause the wrist-wearable device to perform:

detecting a user input within the first portion of the user interface; and in response to detecting the user input within the first portion of the user interface, displaying an additional portion of the user interface that includes a user interface object that, when selected, causes the wrist-wearable device to begin monitoring the user's performance of the activity.

14. The non-transitory, computer-readable storage medium of claim 13, wherein the instructions, when executed by the wrist-wearable device, further cause the wrist-wearable device to perform:

after monitoring the user's performance of the activity:
monitoring, via the one or more sensors that are in communication with the wrist-wearable device, new values for the plurality of physiological parameters for the user wearing the wrist-wearable device;
comparing the new values for the plurality of physiological parameters to the baseline values for the physiological parameters;
based on the comparing of the new values to the baseline values, determining a new qualitative descriptor of the user's physiological state from among the set of three or more predefined qualitative descriptors; and
presenting, on the display that is in communication with the wrist-wearable device, the new qualitative descriptor of the user's physiological state without displaying a numeric score representing the user's physiological state.

15. The non-transitory, computer-readable storage medium of claim 11, wherein the instructions, when executed by the wrist-wearable device, further cause the wrist-wearable device to perform:

before determining the qualitative descriptor, providing a description about values for physiological parameters that will be collected in conjunction with determinations of qualitative descriptors of the user's physiological state by the wrist-wearable device.

16. A wrist-wearable device for providing a qualitative descriptor of a user's physiological state, the wrist-wearable device including:

one or more sensors configured to:
monitor values for a plurality of physiological parameters for a user wearing the wrist-wearable device;
one or more processors in communication with the one or more sensors, the one or more processors configured to:
compare the values for the plurality of physiological parameters to baseline values for the physiological parameters, the baseline values being determined based on values for the plurality of physiological parameters that were measured over a predetermined period of time while the user was in a state of deep sleep;
based on the comparing, determining a qualitative descriptor of the user's physiological state from among a set of three or more predefined qualitative descriptors; and a display that is in communication with the one or more sensors and the one or more processors, the display configured to:
present a description of how the set of three or more qualitative descriptors of a user's physiological state will be determined by the wrist-wearable device and an explanation of research behind the use of qualitative descriptors of the user's physiological state;
present the qualitative descriptor of the user's physiological state without displaying a numeric score representing the user's physiological state.

17. The wrist-wearable device of claim 16, wherein the one or more processors are further configured to:

determine an activity for the user to perform in the physical world that is predicted to be suitable for the user based on the qualitative descriptor of the user's physiological state.

18. The wrist-wearable device of claim 17, wherein the qualitative descriptor of the user's physiological state is displayed in a first portion of a user interface on the display, and the one or more processors are further configured to:

detect a user input within the first portion of the user interface; and in response to detecting the user input within the first portion of the user interface, display an additional portion of the user interface that includes a user interface object that, when selected, causes the wrist-wearable device to begin monitoring the user's performance of the activity.

19. The wrist-wearable device of claim 18, wherein the one or more processors are further configured to:

after monitoring the user's performance of the activity:
monitor, via the one or more sensors that are in communication with the wrist-wearable device, new values for the plurality of physiological parameters for the user wearing the wrist-wearable device;
compare the new values for the plurality of physiological parameters to the baseline values for the physiological parameters;
based on the comparing of the new values to the baseline values, determine a new qualitative descriptor of the user's physiological state from among the set of three or more predefined qualitative descriptors; and
present, on the display that is in communication with the wrist-wearable device, the new qualitative descriptor of the user's physiological state without displaying a numeric score representing the user's physiological state.

20. The wrist-wearable device of claim 16, wherein the one or more processors are further configured to:

before determining the qualitative descriptor, provide a description about values for physiological parameters that will be collected in conjunction with determinations of qualitative descriptors of the user's physiological state by the wrist-wearable device.

\* \* \* \* \*